United States Patent
Yun et al.

(10) Patent No.: US 11,235,072 B2
(45) Date of Patent: Feb. 1, 2022

(54) ADENOVIRUS COMPLEX FOR GENE DELIVERY AND GENE IHERAPY

(71) Applicant: INDUSTRY-UNIVERSITY COOPERATION FOUNDATION HANYANG UNIVERSITY, Seoul (KR)

(72) Inventors: Chae Ok Yun, Seoul (KR); Youjin Na, Seoul (KR)

(73) Assignee: GENEMEDICINE CO., LTD.

( * ) Notice: Subject to any disclaimer, the term of this patent is extended or adjusted under 35 U.S.C. 154(b) by 385 days.

(21) Appl. No.: 15/952,191

(22) Filed: Apr. 12, 2018

(65) Prior Publication Data

US 2018/0296701 A1 Oct. 18, 2018

Related U.S. Application Data

(63) Continuation-in-part of application No. PCT/KR2016/011437, filed on Oct. 12, 2016.

(30) Foreign Application Priority Data

Oct. 12, 2015 (KR) .......................... 10-2015-0142434

(51) Int. Cl.
| | |
|---|---|
| *A61K 35/761* | (2015.01) |
| *A61K 38/00* | (2006.01) |
| *A61K 38/10* | (2006.01) |
| *A61K 47/60* | (2017.01) |
| *A61P 35/00* | (2006.01) |
| *C12N 15/861* | (2006.01) |
| *A61K 48/00* | (2006.01) |

(52) U.S. Cl.
CPC ........ *A61K 48/0041* (2013.01); *A61K 35/761* (2013.01); *A61K 38/00* (2013.01); *A61K 47/60* (2017.08); *A61P 35/00* (2018.01)

(58) Field of Classification Search
None
See application file for complete search history.

(56) References Cited

FOREIGN PATENT DOCUMENTS

| EP | 2896402 | * | 2/2015 |
| EP | 2896402 | A1 | 7/2015 |

OTHER PUBLICATIONS

Xu et al, The systemic delivery of an oncolytic adenovirus expressing decorin inhibits bone metastasis in a mouse model of human prostate cancer, Gene Ther. Mar. 2015 ; 22(3): 247-256.*

Dreier et al, Her2-specific Multivalent Adapters Confer Designed Tropism to Adenovirus for Gene Targeting, Mol Biol. Jan. 14, 2011; 405(2): 410-426.*

Kim et al, Bioreducible polymer-conjugated oncolytic adenovirus for hepatoma-specific therapy via systemic administration, Biomaterials 32 (2011) 9328-9342.*

Dupouy, Sandra et al., "The potential use of the neurotensin high affinity receptor 1 as a biomarker for cancer progression and as a component of personalized medicine in selective cancers", Biochimie 93 (2011) 1369-1378.

Eto, Yusuke et al., "PEGylated adenovirus vectors containing RGD peptides on the tip of PEG show high transduction efficiency and antibody evasion ability", The Journal of Gene Medicine, 2005; 7:604-612.

Na, Youjin et al., "113. Potent Therapeutic Efficacy of Neurotensin Receptor-Targeting and Extracellular Matrix-Degrading Oncolytic Adenovirus in an Orthotopic Pancreatic Tumor Model", Molecular Therapy, vol. 24, Supplement 1, May 2016, S47-S48.

Reubi, J.C., "Neurotensin receptors: a new marker for human ductal pancreatic adenocarcinoma", Gut 1998; 42:546-550.

Chiara Falciani et al., "Modular Branched Neurotensin Peptides for Tumor Target Tracing and Recptor-Mediated Therapy: A Proof-of-Concept", Current Cancer Drug Targets, 2010, 10, 695-704.

Yukyung Jung et al., "Retargeting of adenoviral gene delivery via Herceptin-PEG-adenovirus conjugates to breast cancer cells", Journal of Controlled Release 123 (2007) 164-171.

Jung-Sun Lee et al., "A Novel sLRP6E1E2 Inhibits Canonical Wnt Signaling, Epithelial-to-Mesenchymal Transition, and Induces Mitochondria-Dependent Apoptosis in Lung Cancer", PLoS ONE, May 2012, vol. 7, Issue 5, 14 pages.

Youjin Na et al., "Potent antitumor effect of neurotensin receptor-targeted oncolytic adenovirus co-expressing decorin and Wnt antagonist in an orthotopic pancreatic tumor model", Journal of Controlled Release 220 (2015) 766-782.

Office Action for Application 201680068461.X, dated Nov. 20, 2020, with English translation, 28 pages.

Tralhão JG, Schaefer L, Micegova M, et al. In vivo selective and distant killing of cancer cells using adenovirus-mediated decorin gene transfer. FASEB J. 2003;17(3):464-466.

* cited by examiner

*Primary Examiner* — Maria Marvich
(74) *Attorney, Agent, or Firm* — Adsero IP

(57) ABSTRACT

The present invention relates to an adenovirus complex which can be utilized for gene delivery and gene therapy by targeting neurotensin receptors. The complex of the present invention has an excellent antitumor effect because of a high intracellular gene transfer efficiency and target specificity by neurotensin receptor-specific binding, has little hepatotoxicity and immunogenicity, forms a stable complex, has low immunogenicity, and thus has a low loss in blood even in an in vivo environment. Therefore, the complex of the present invention can be effectively used for gene therapy.

8 Claims, 35 Drawing Sheets

Specification includes a Sequence Listing.

[FIG. 1]
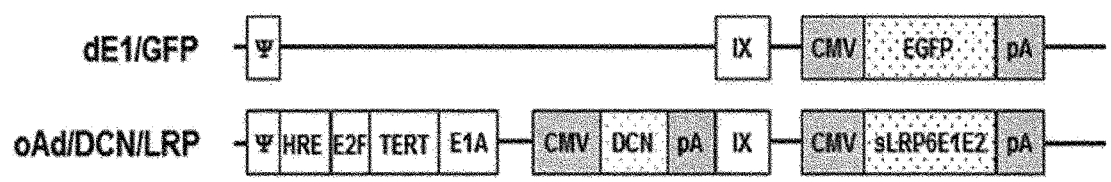
[FIG. 2]
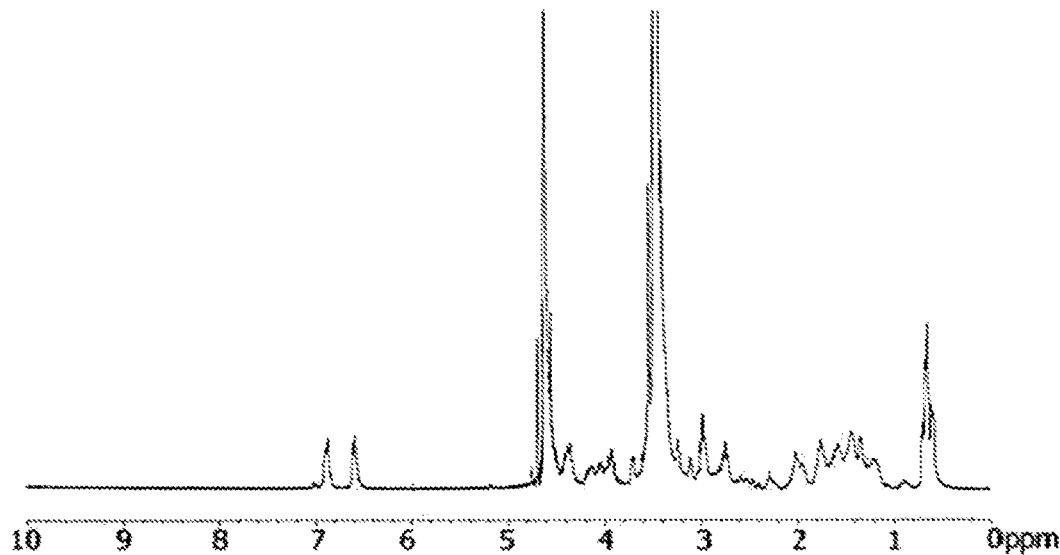

[FIG. 3]
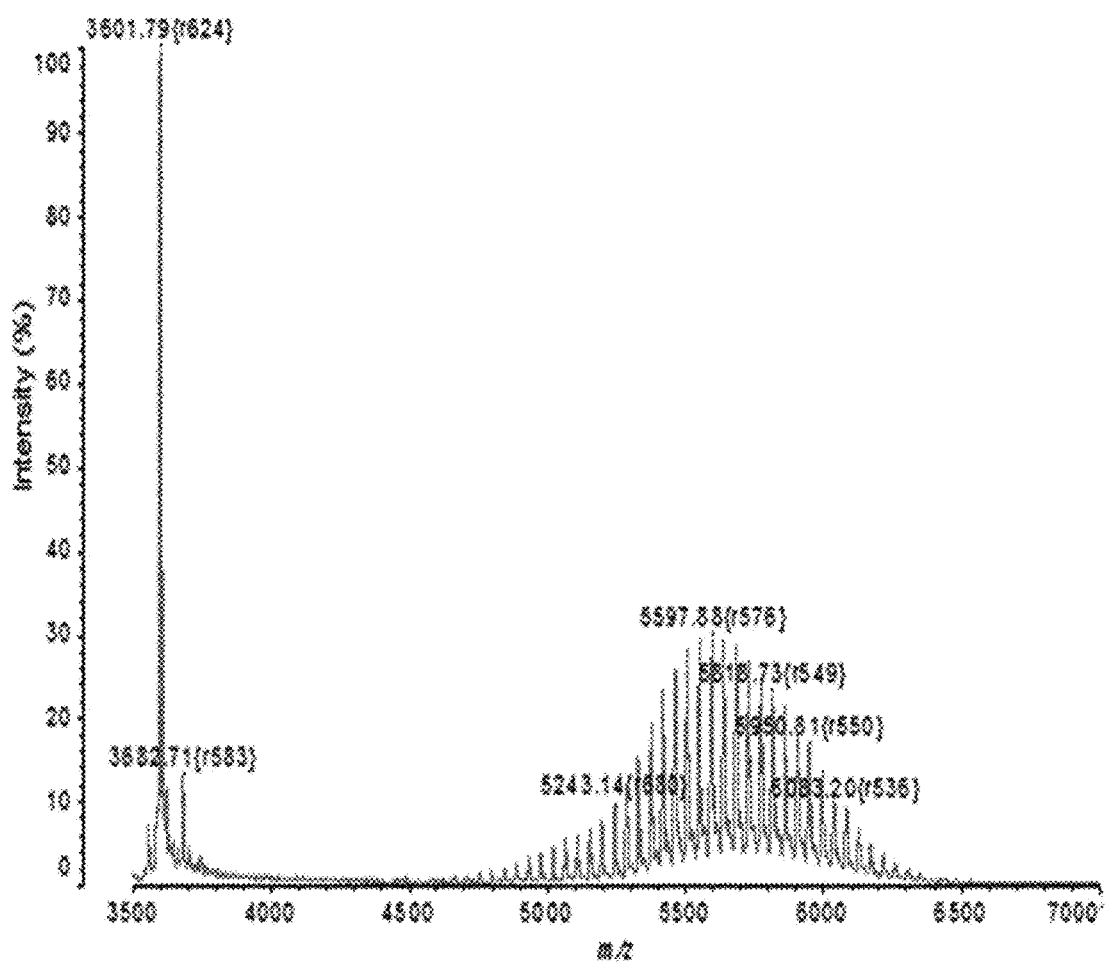

[FIG. 4A]
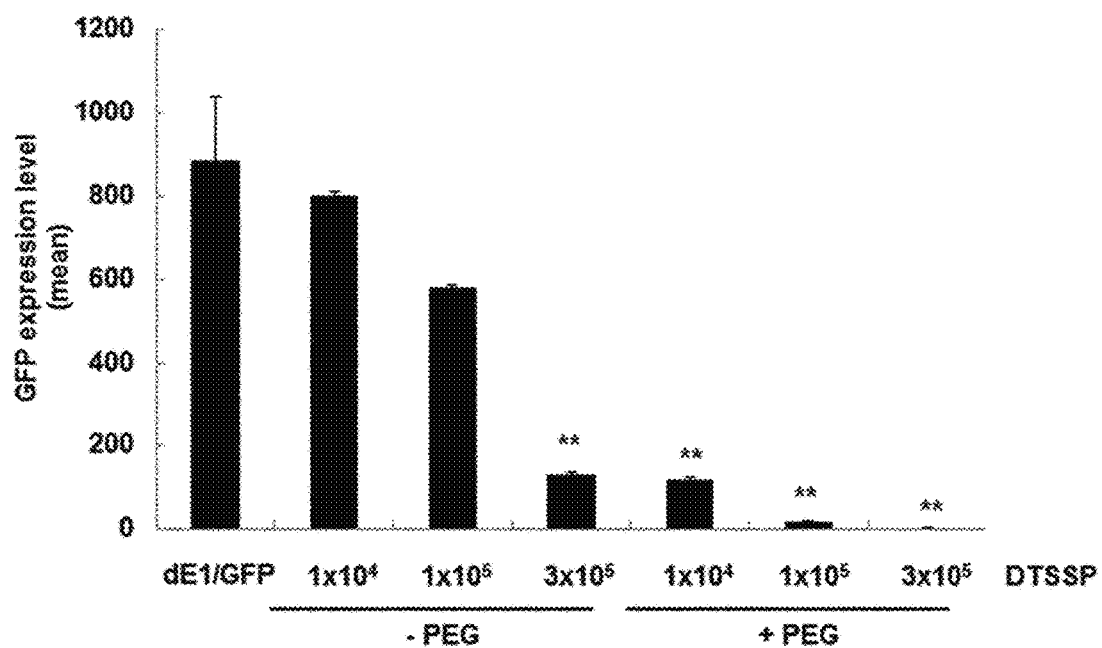
[FIG. 4B]
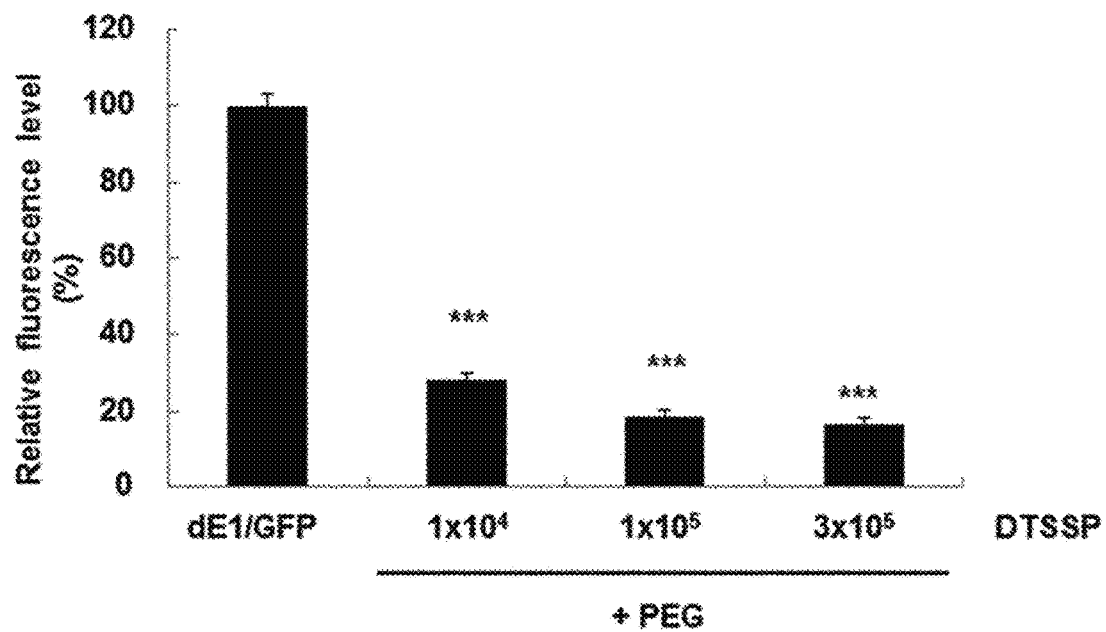

[FIG. 5A]
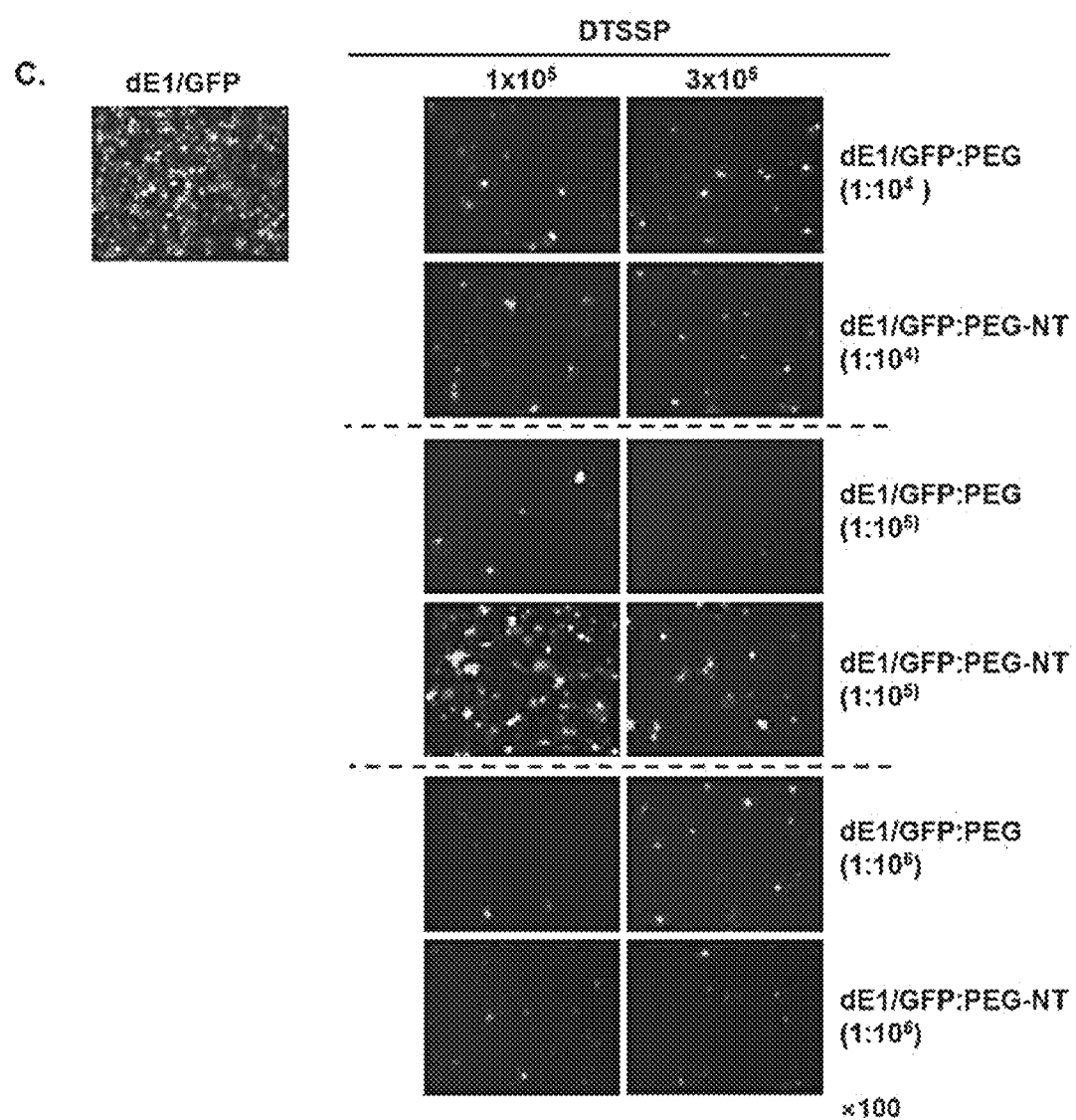

[FIG. 5B]
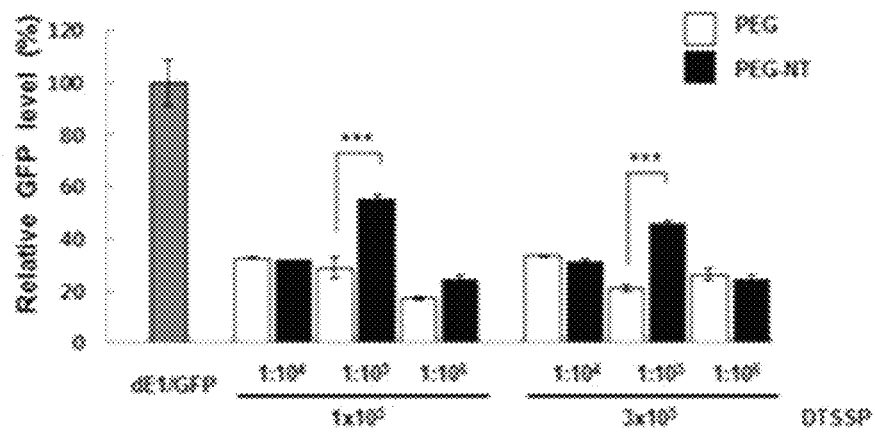
[FIG. 6A]
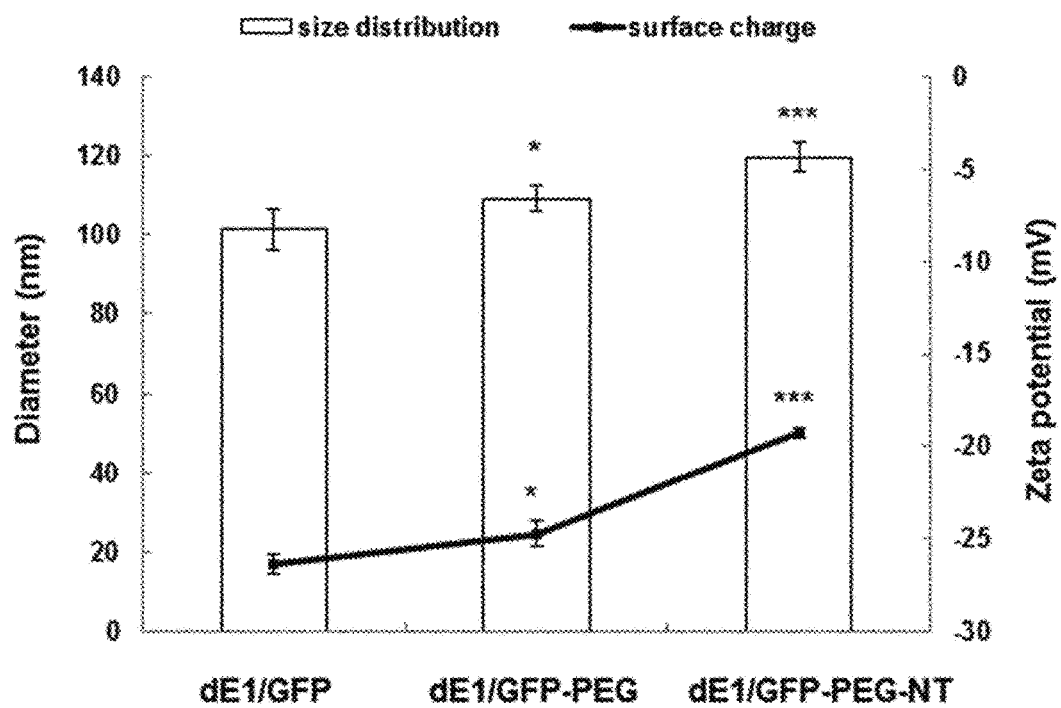

[FIG. 6B]
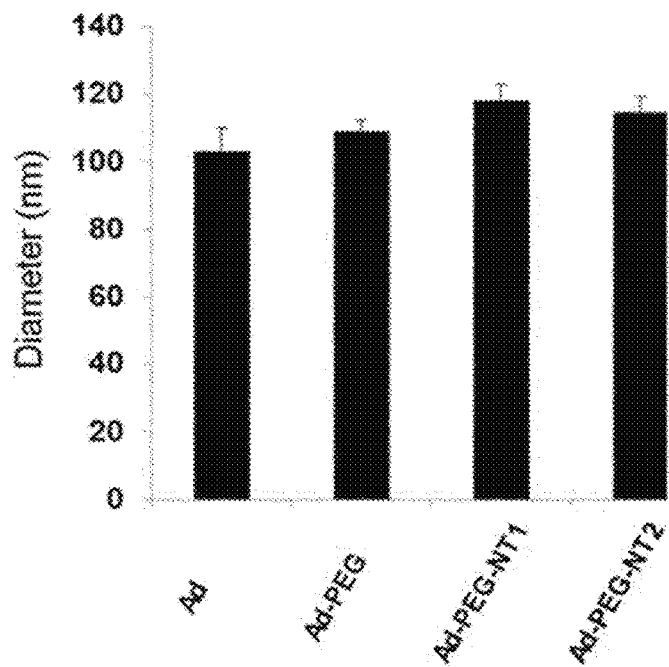
[FIG. 6C]
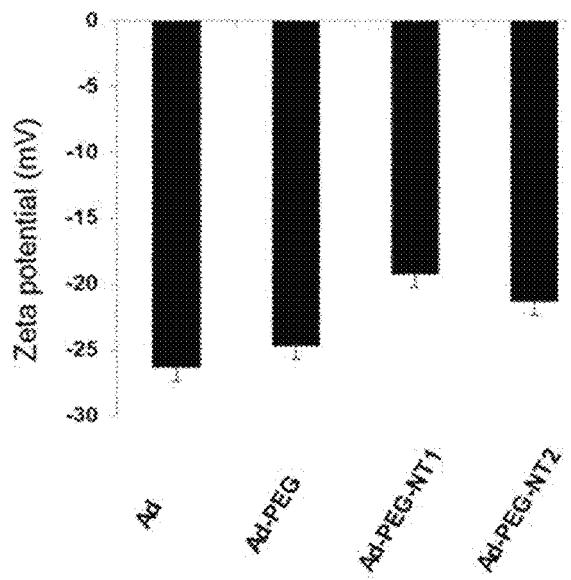

[FIG. 7A]
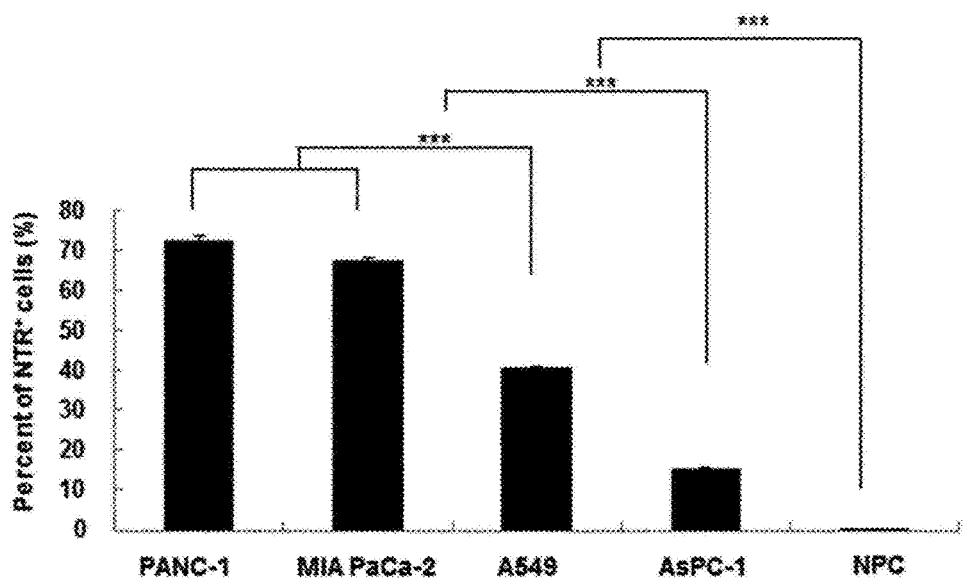
[FIG. 7B]
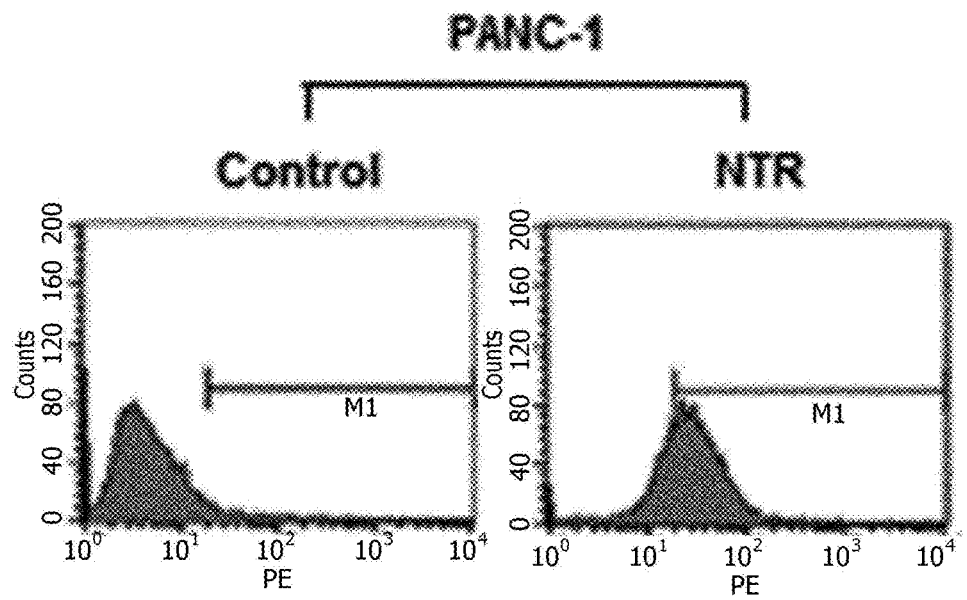

[FIG. 7C]
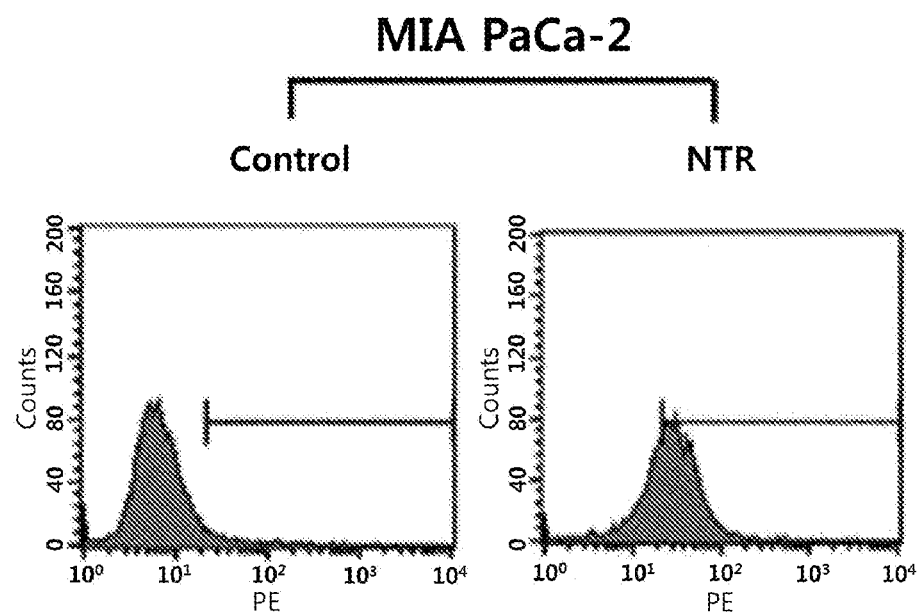
[FIG. 7D]
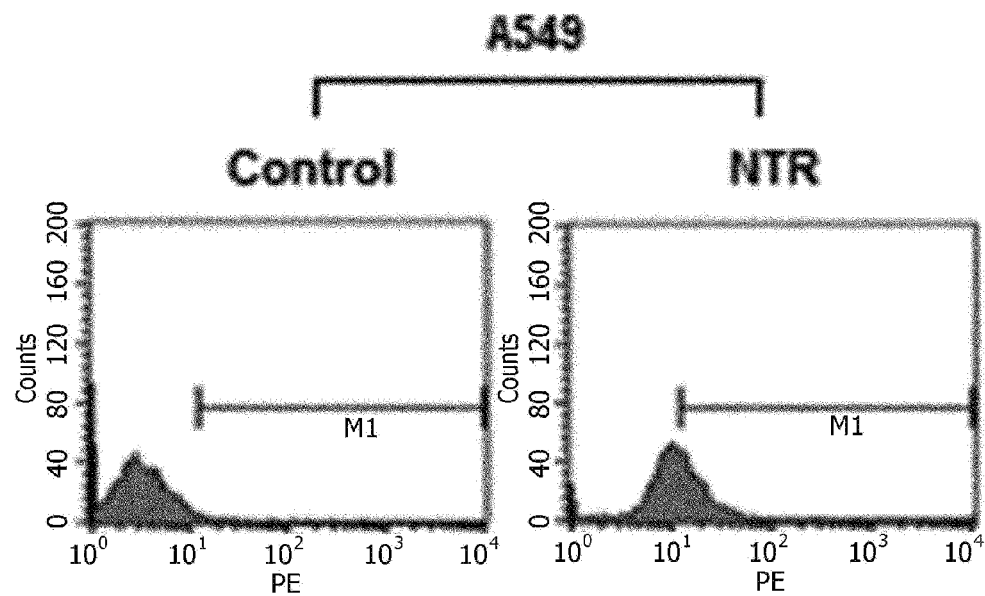

【FIG. 7E】
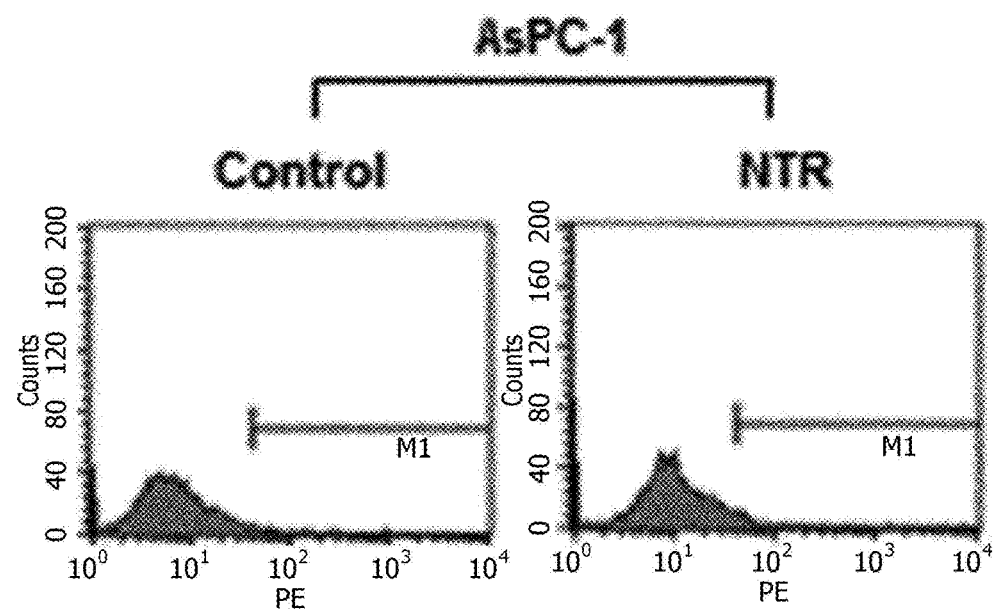
【FIG. 7F】
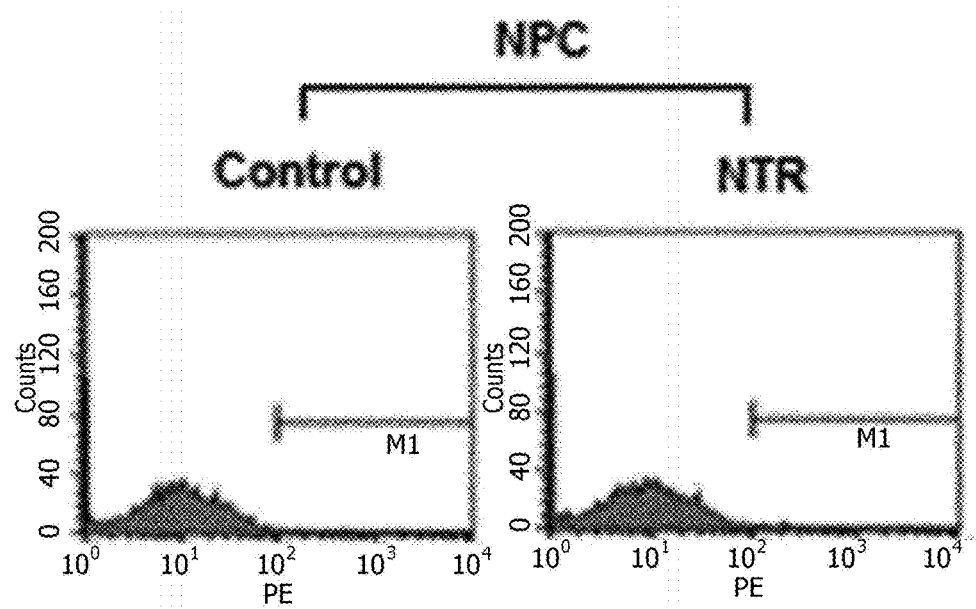

[FIG. 7G]
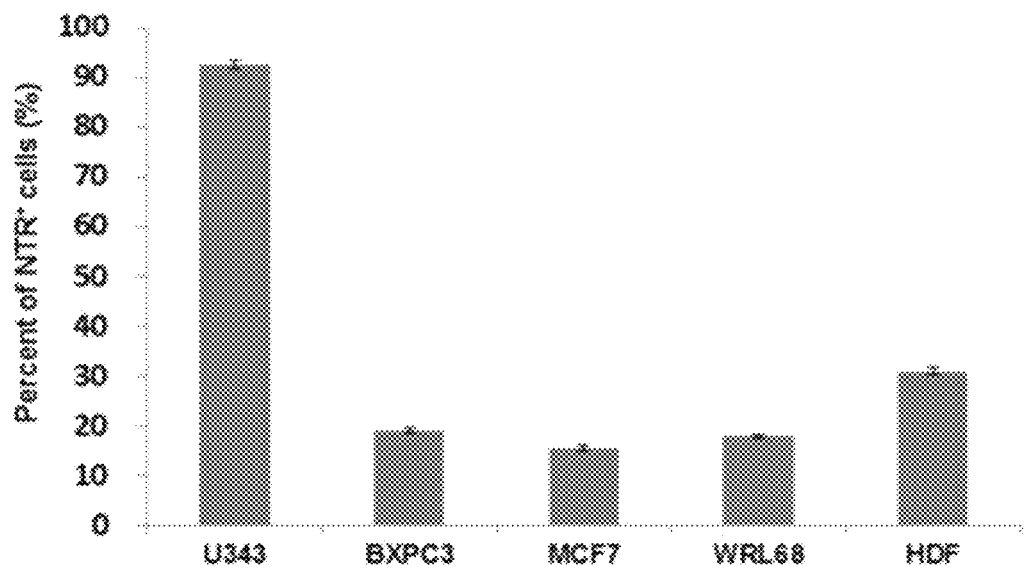
[FIG. 8A]
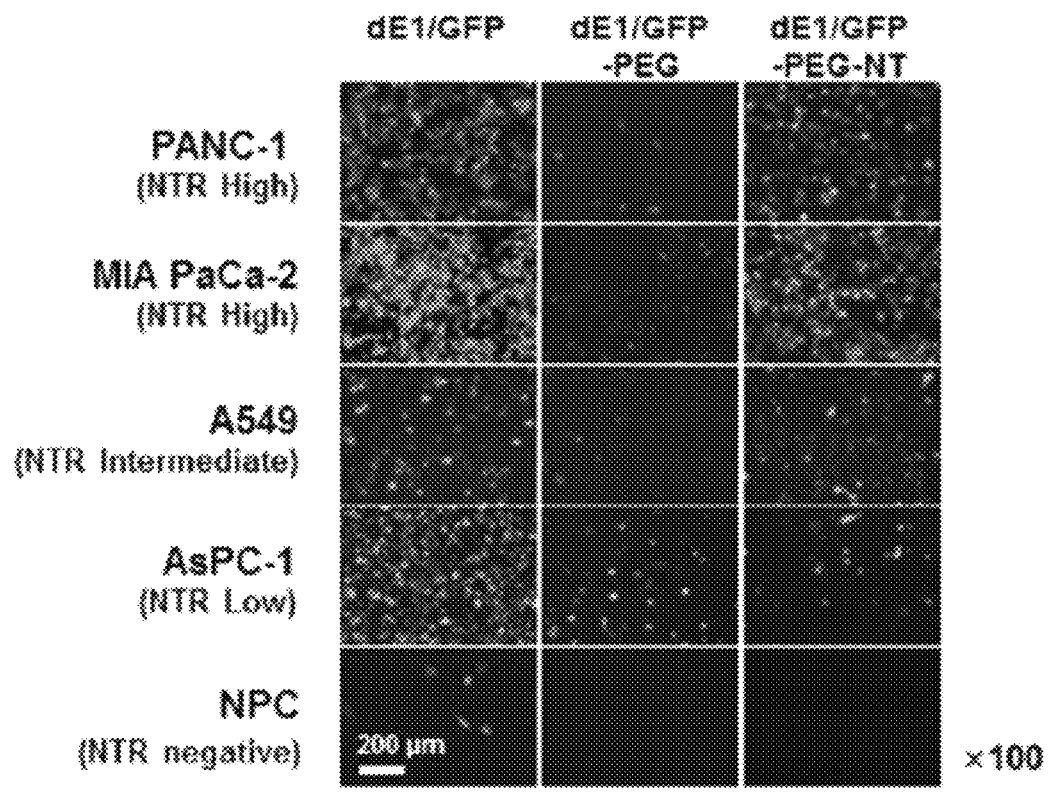

[FIG. 8B]
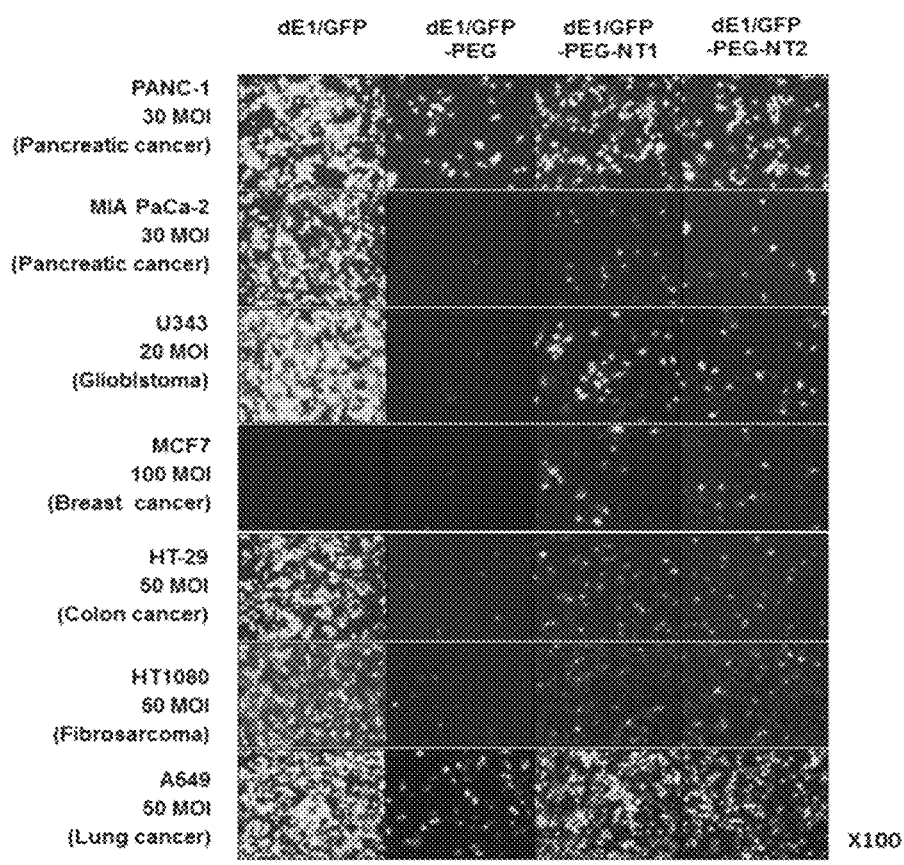

[FIG. 9]
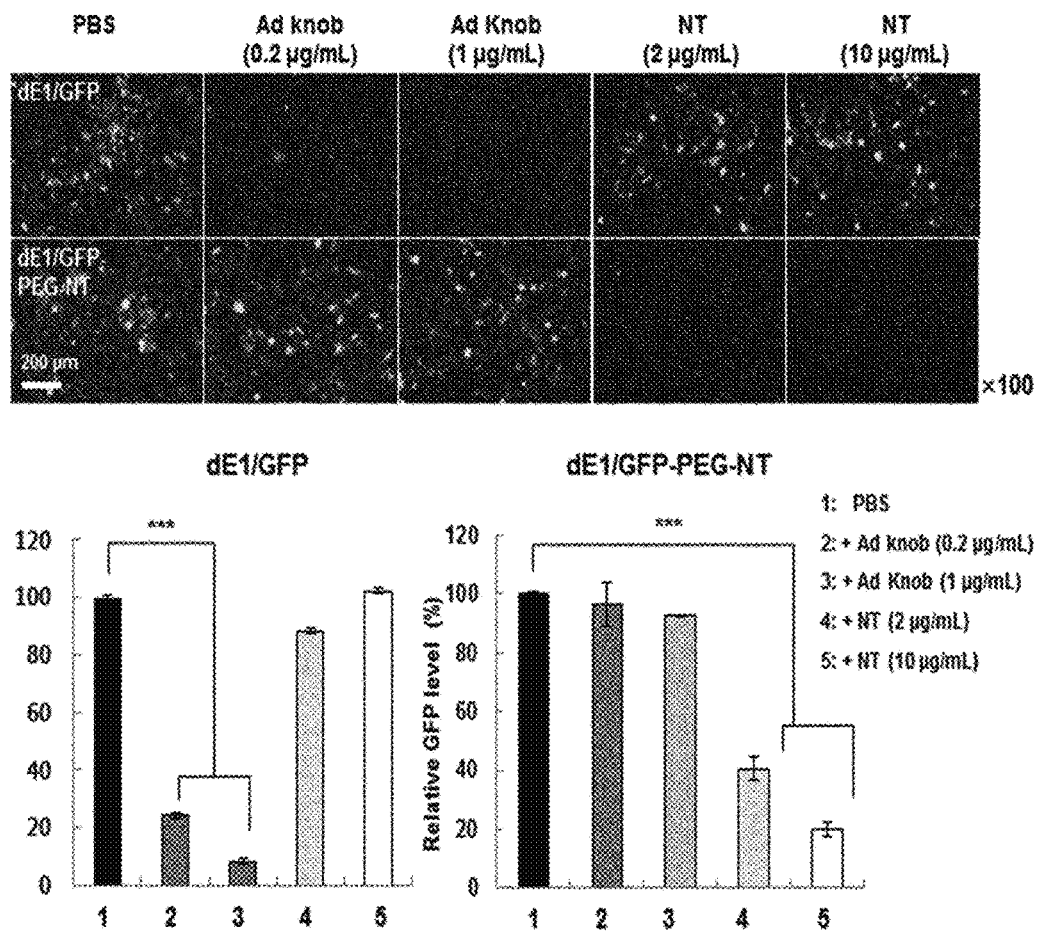
[FIG. 10A]
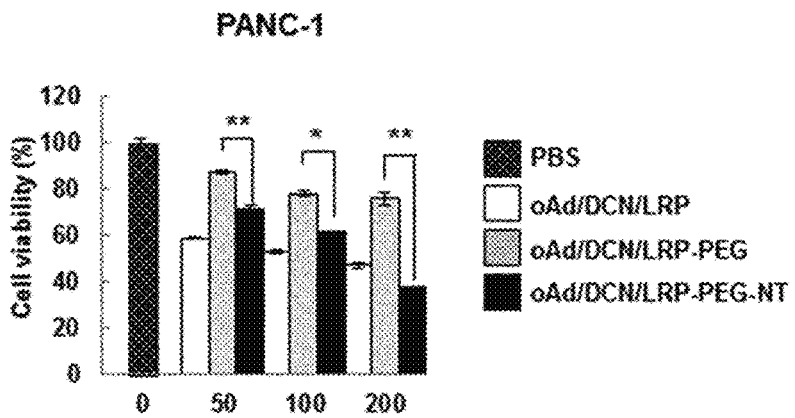

[FIG. 10B]
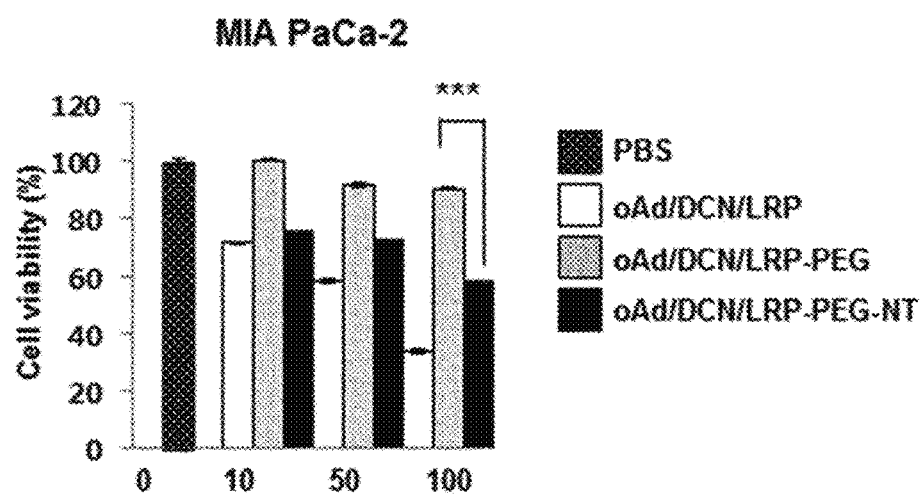
[FIG. 10C]
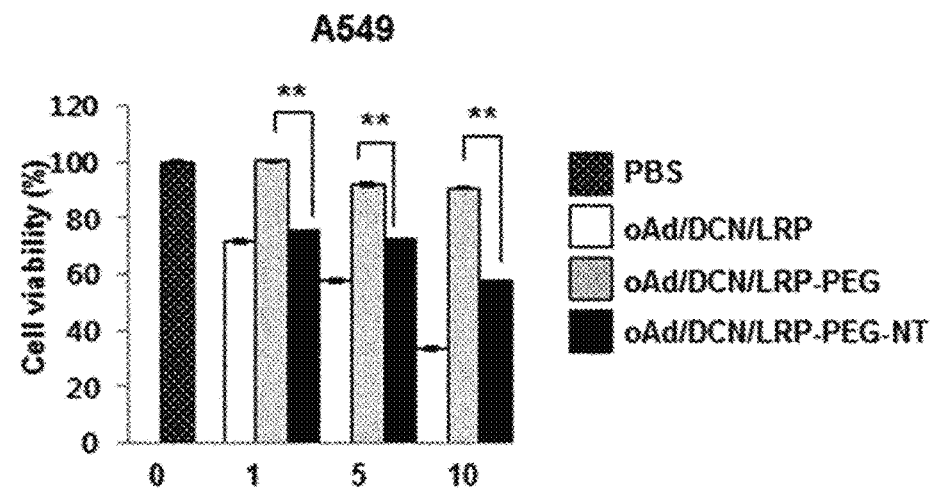

[FIG. 10D]
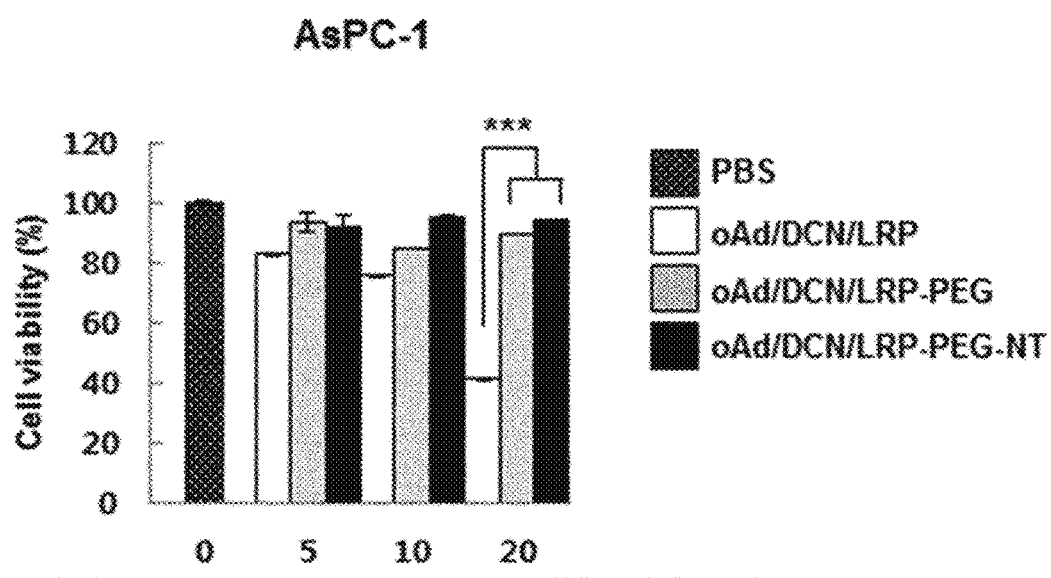
[FIG. 10E]
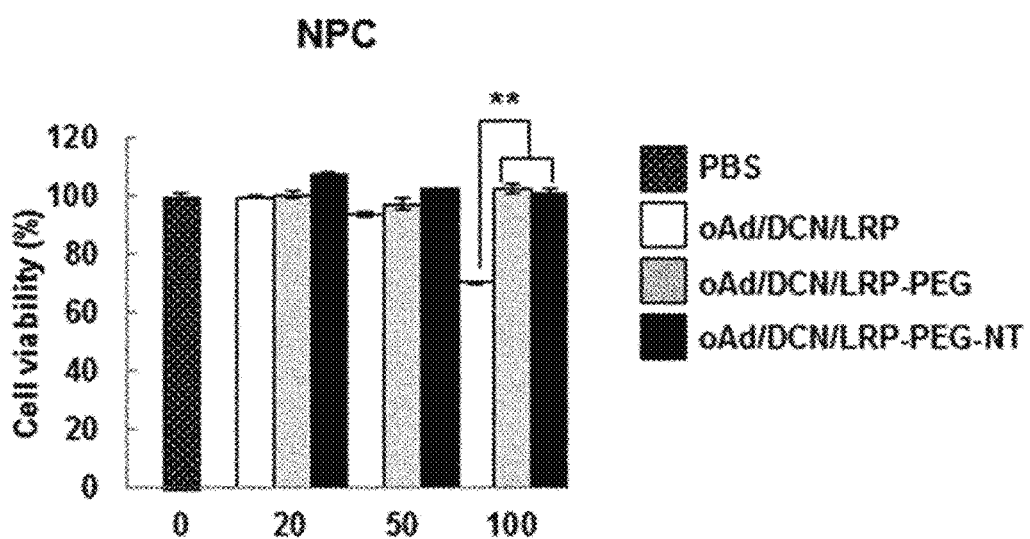

【FIG. 11A】
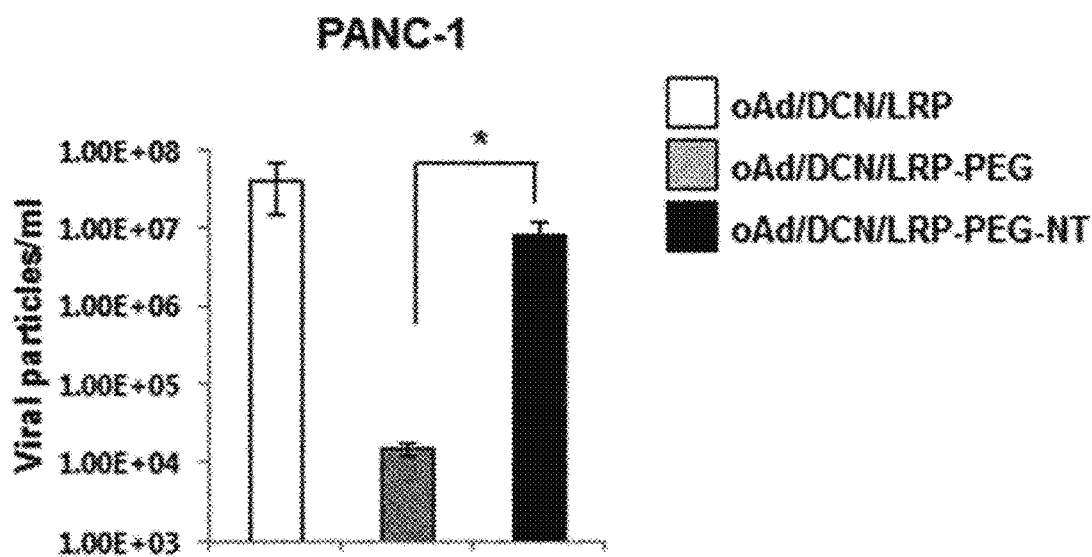
【FIG. 11B】
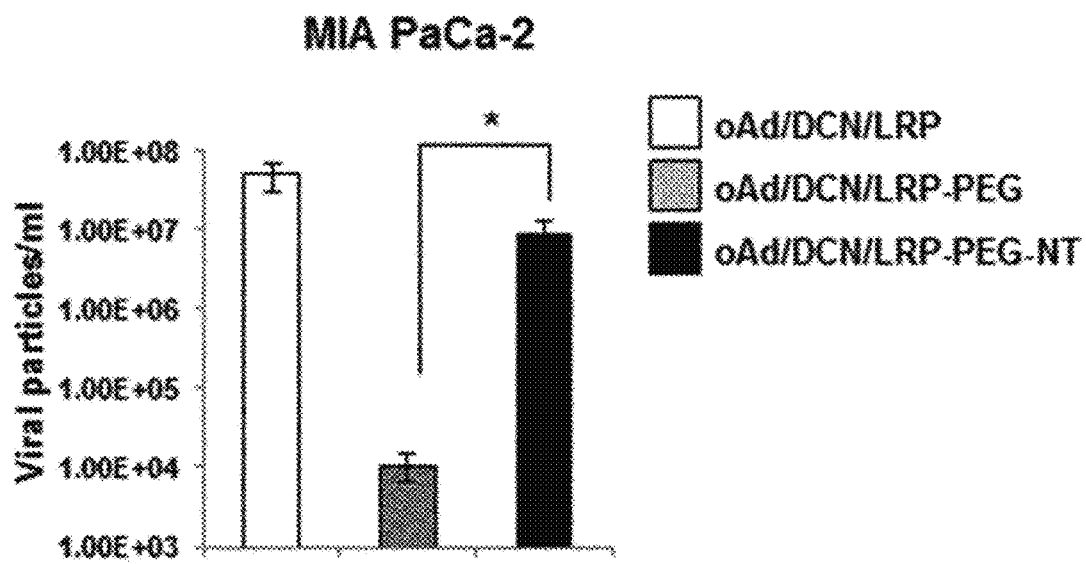

[FIG. 11C]
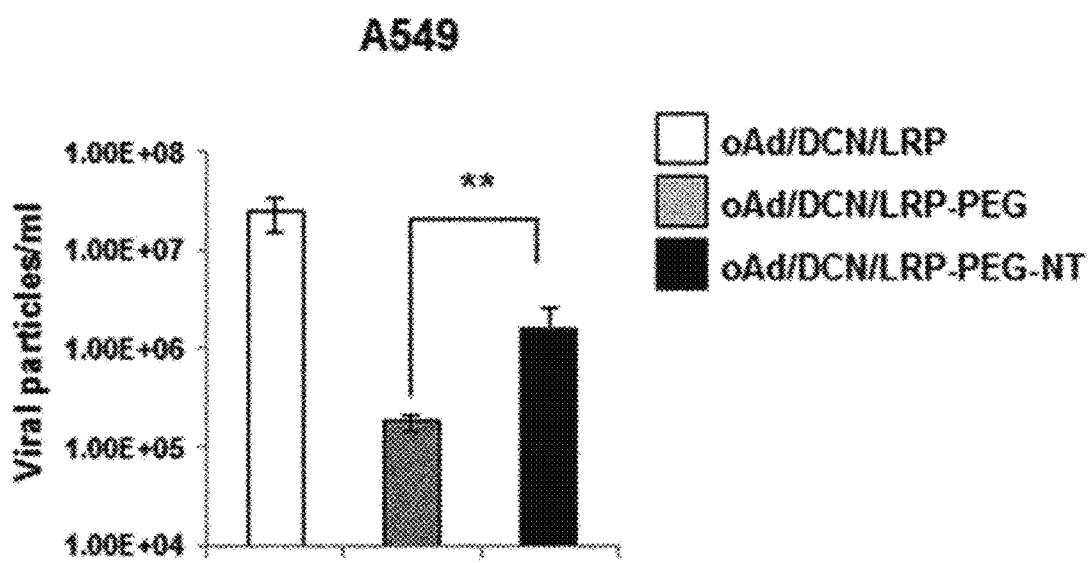
[FIG. 11D]
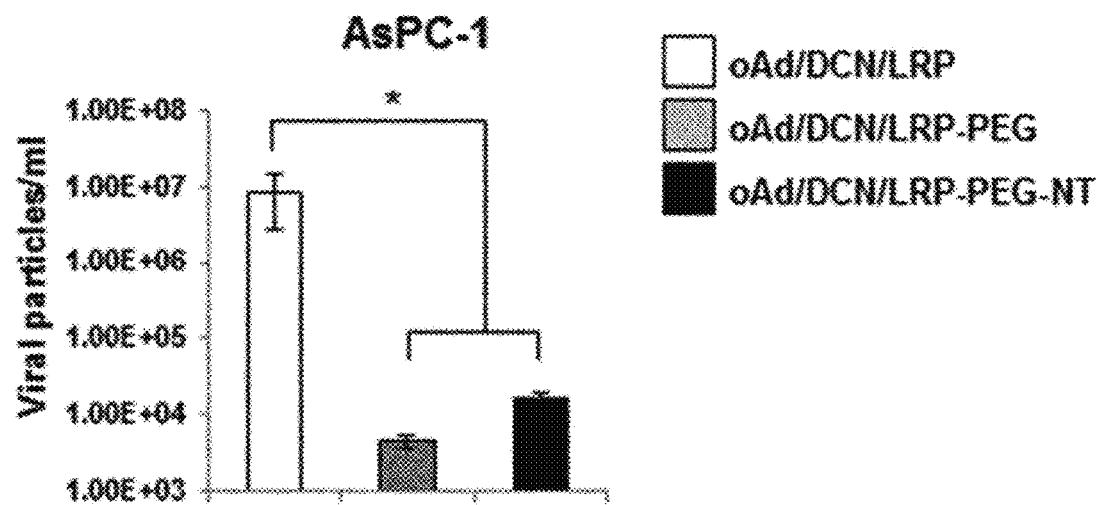

[FIG. 11E]
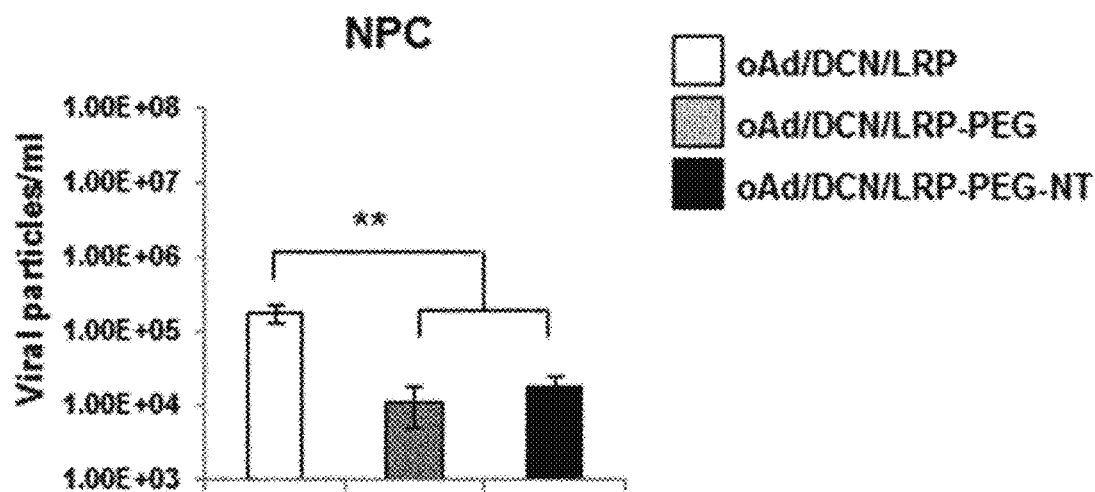
[FIG. 12A]
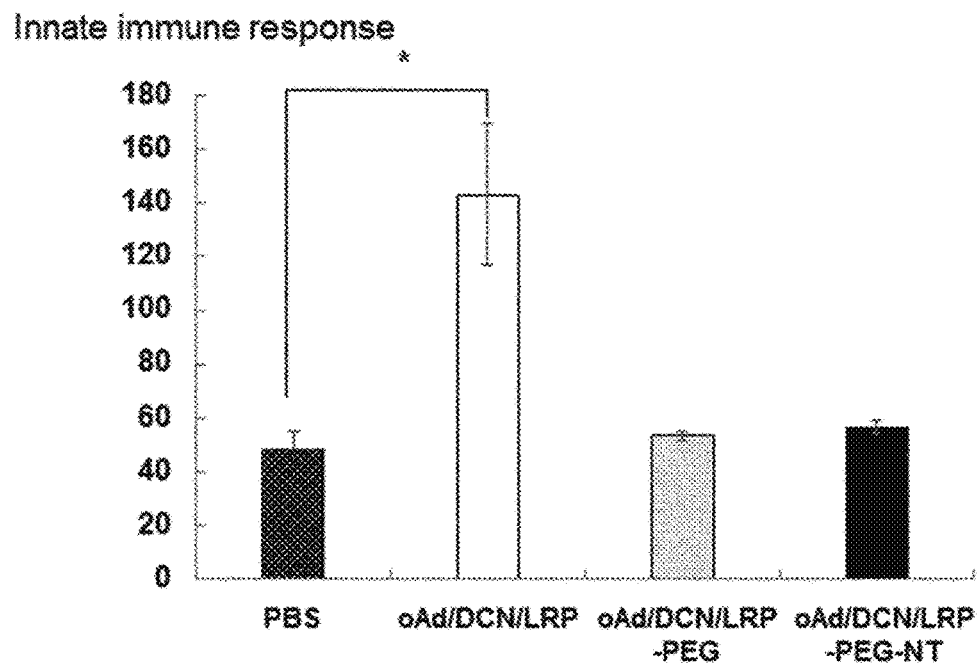

[FIG. 12B]
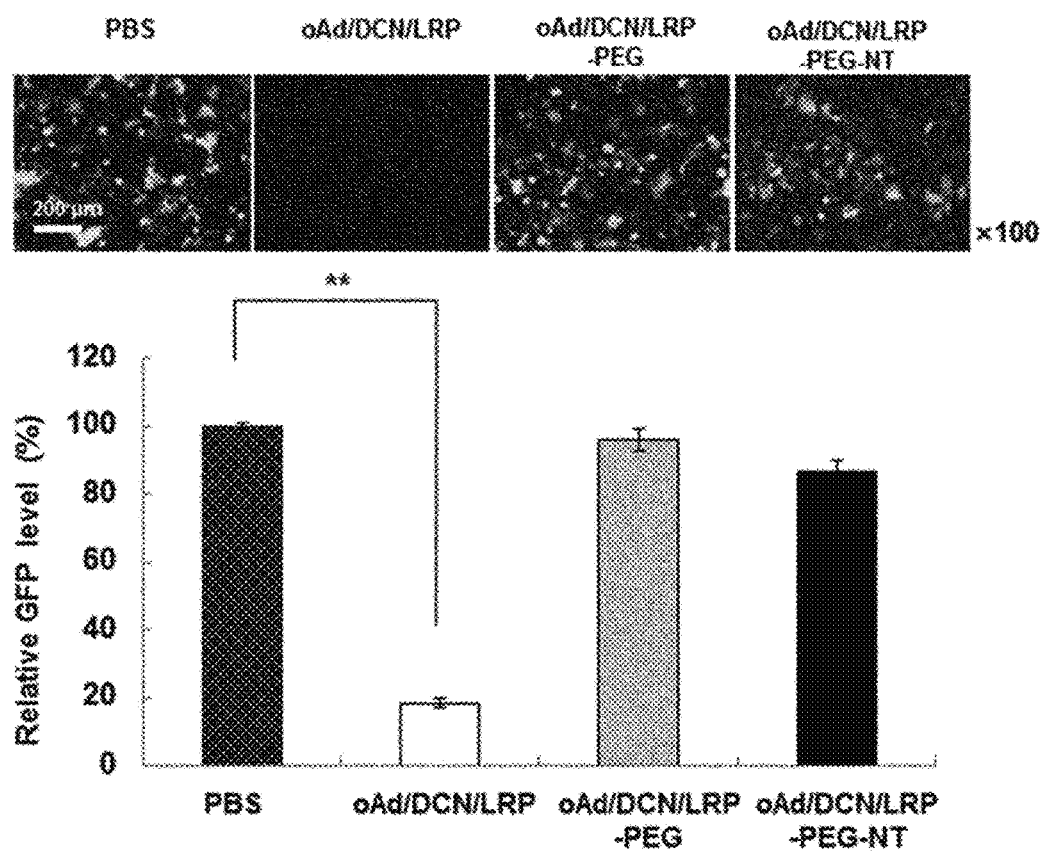

[FIG. 13]
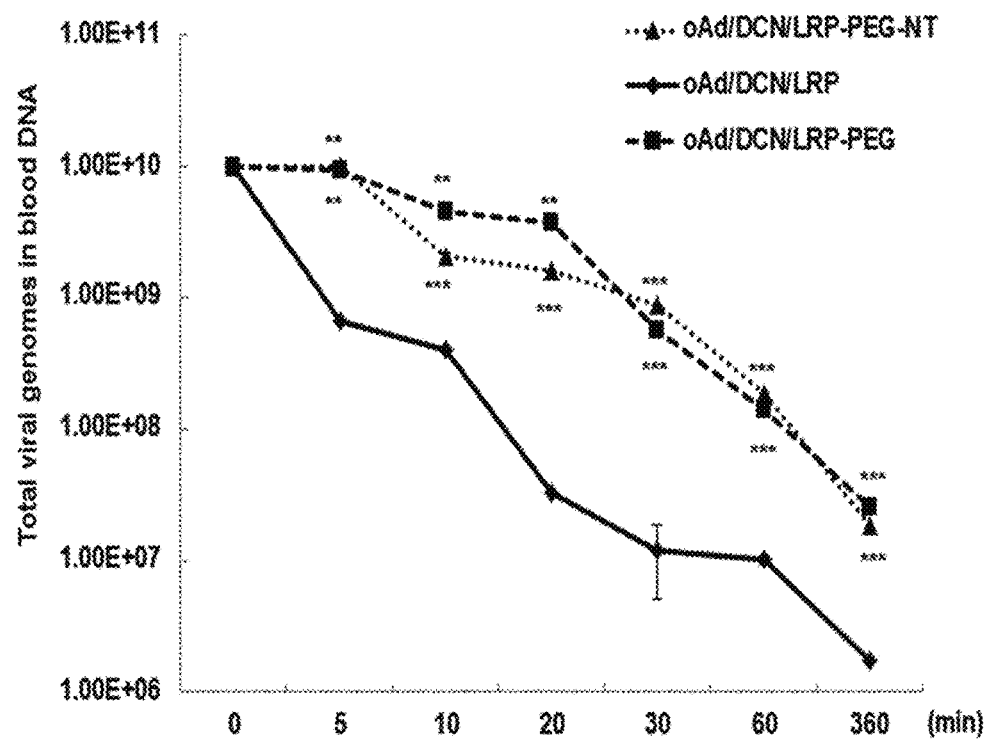

[FIG. 14A]
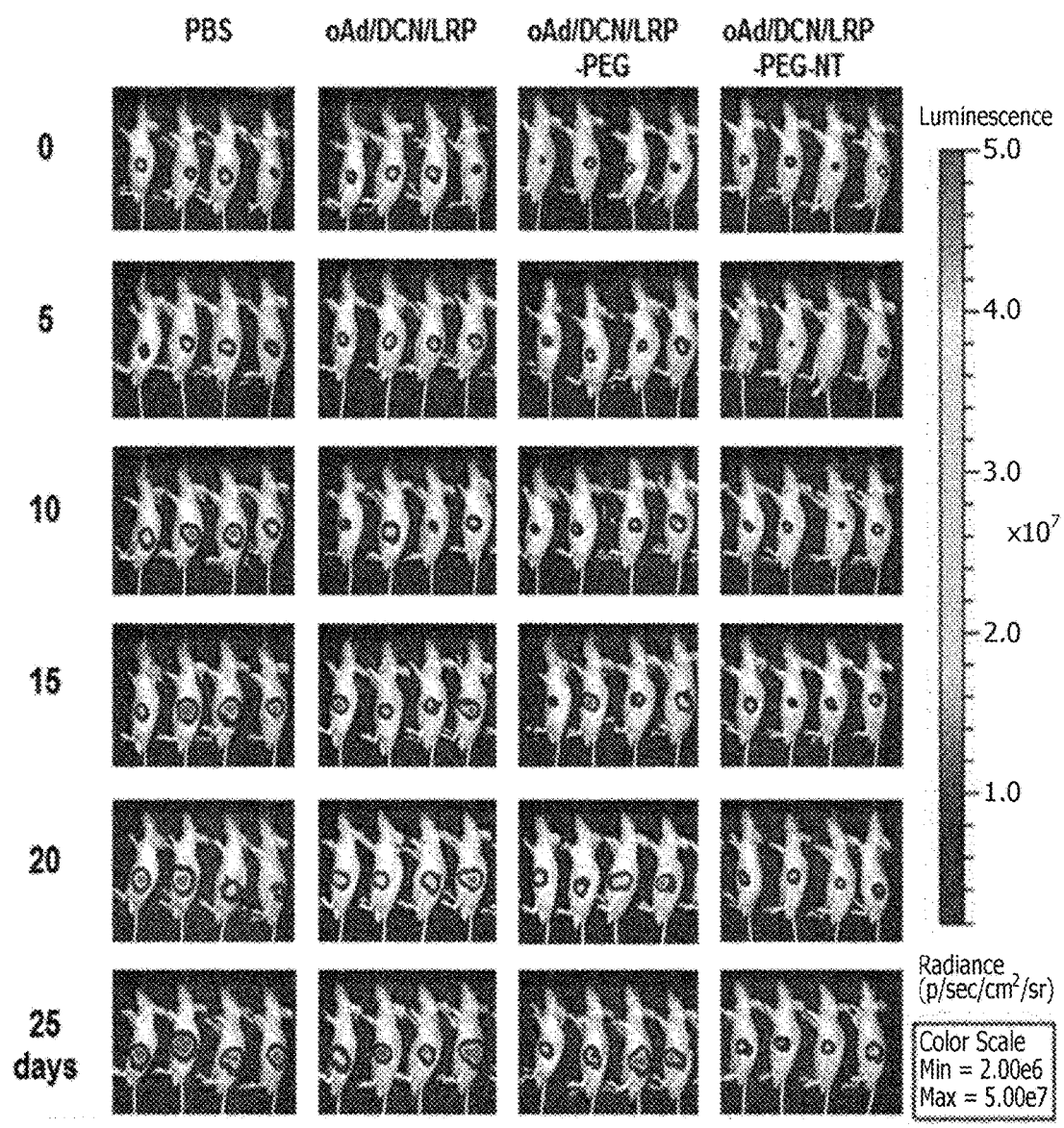

[FIG. 14B]
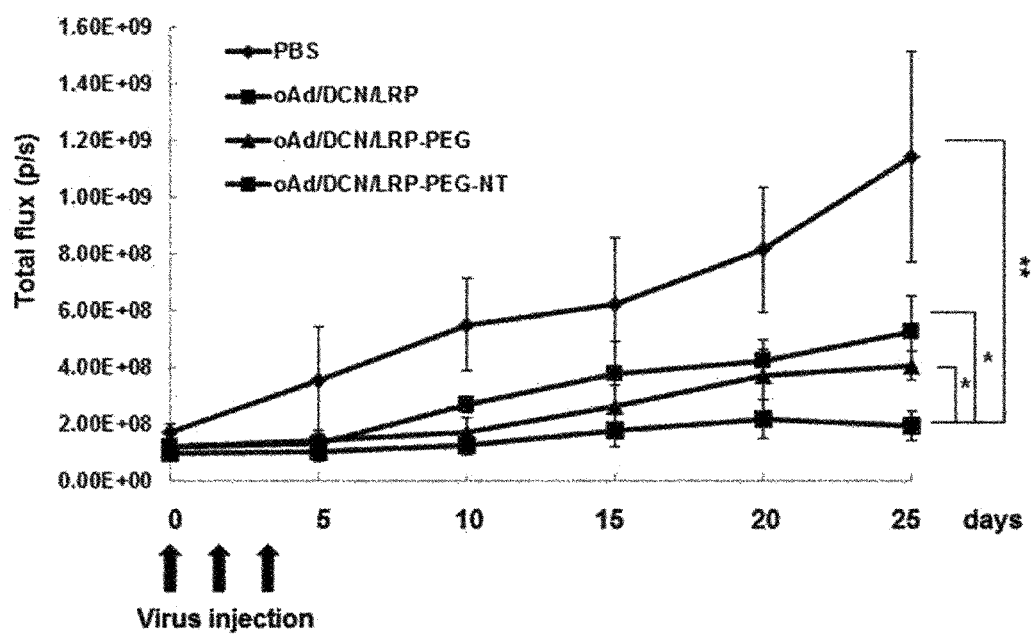
[FIG. 14C]
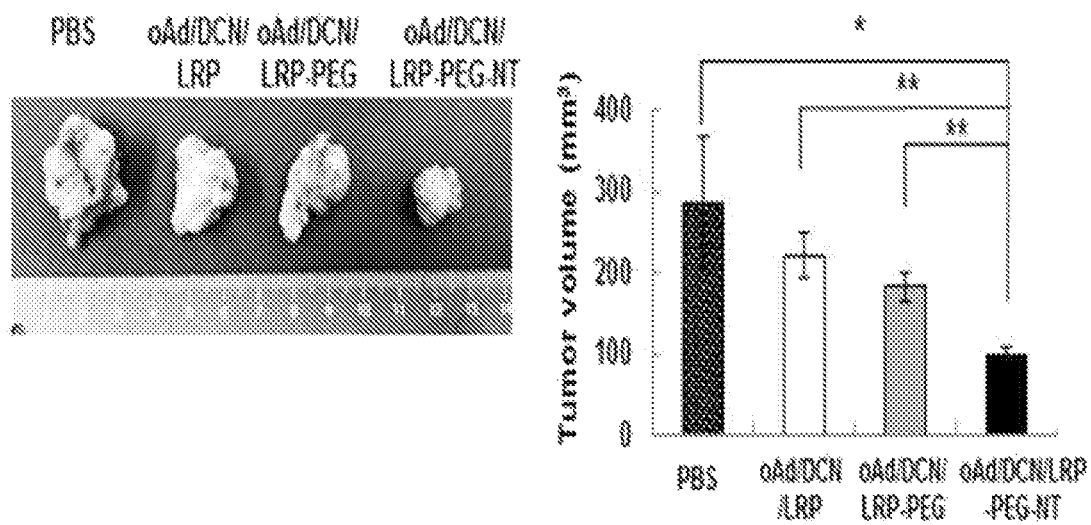

[FIG. 15A]
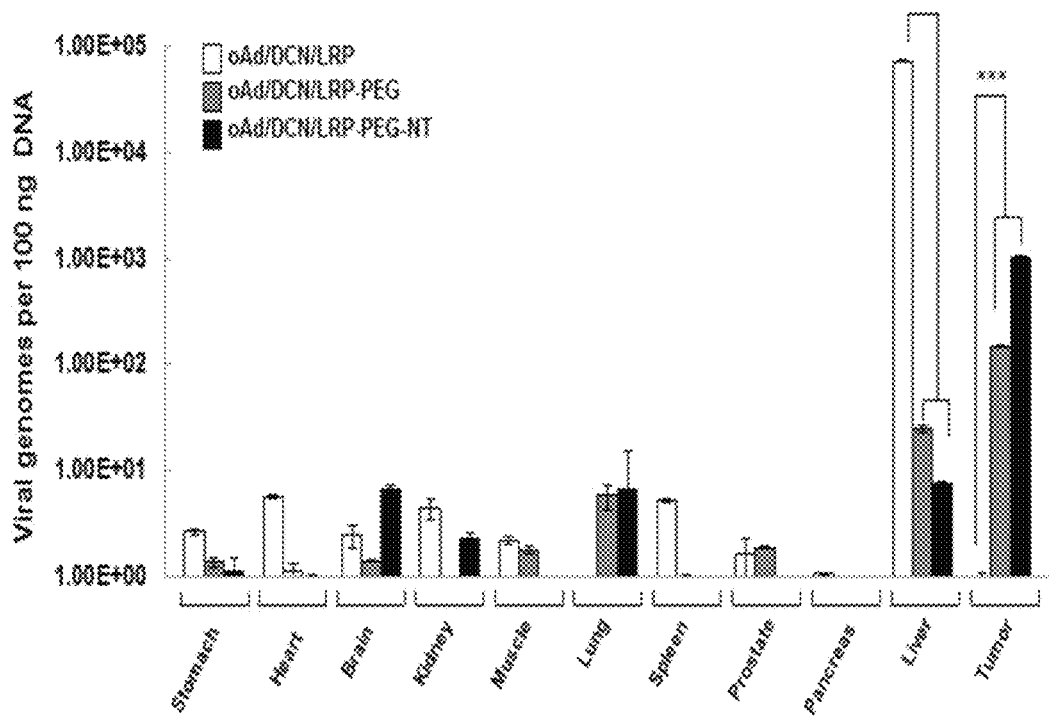
[FIG. 15B]
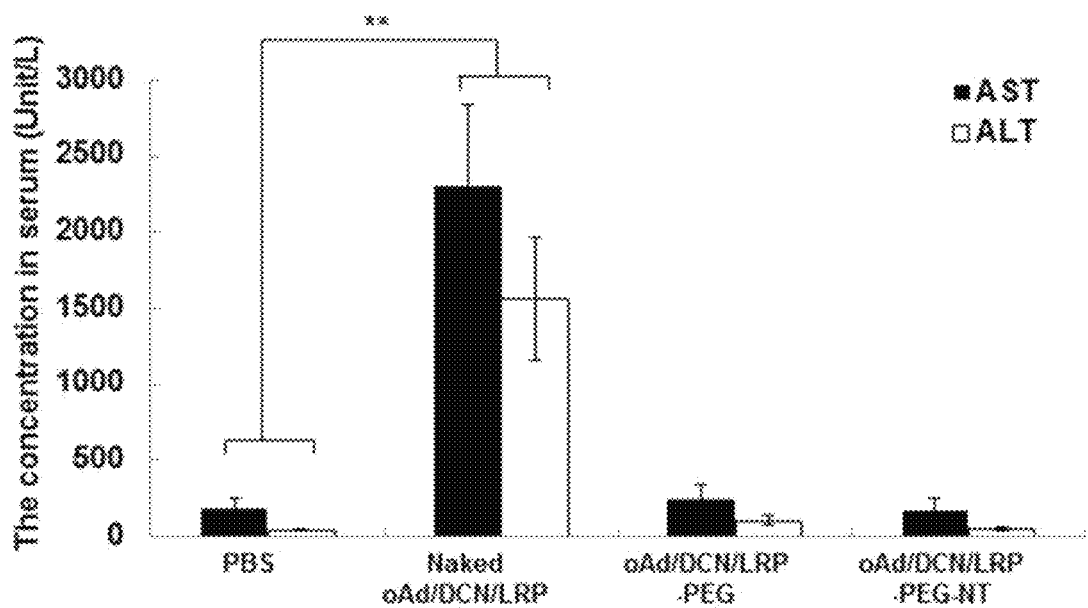

[FIG. 15C]
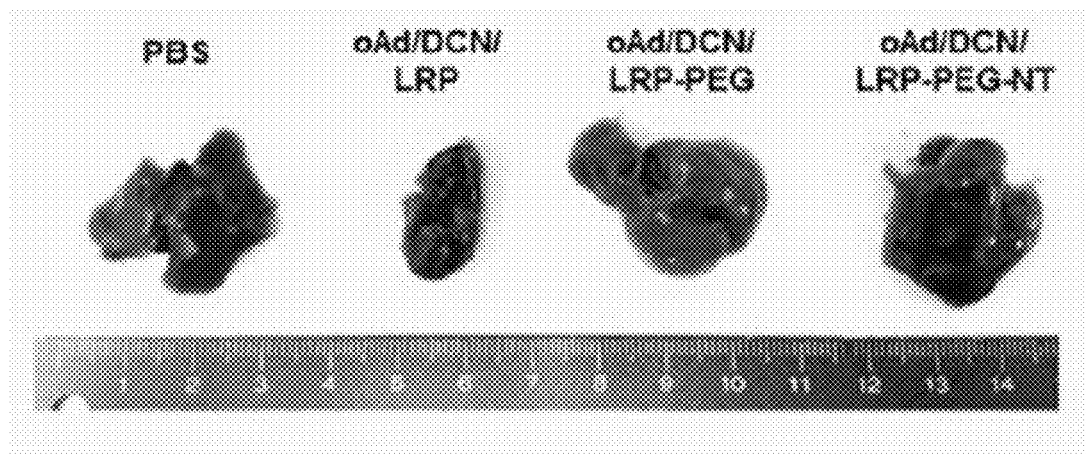
[FIG. 15D]
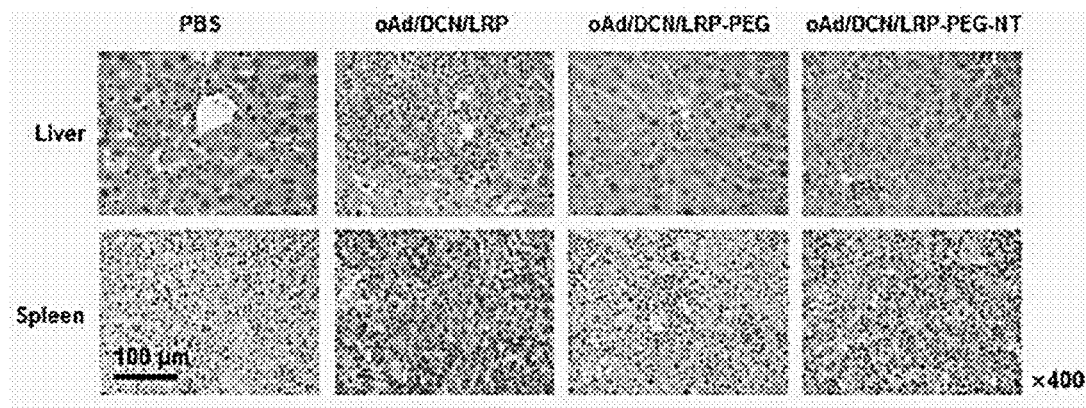

[FIG. 15E]
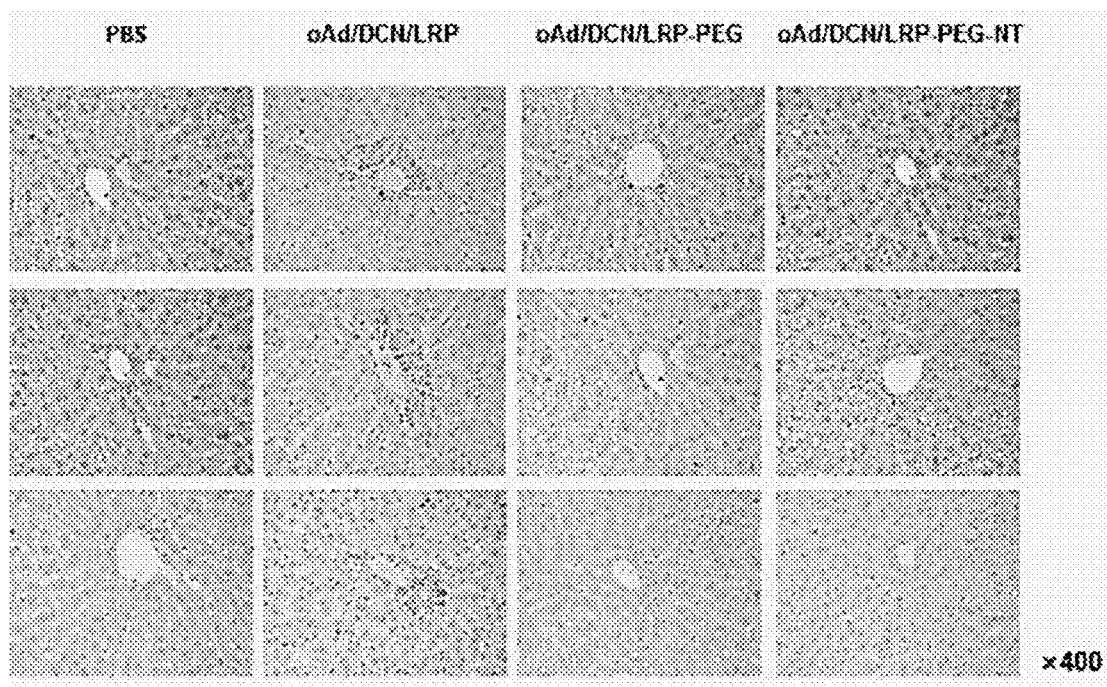
[FIG. 16]
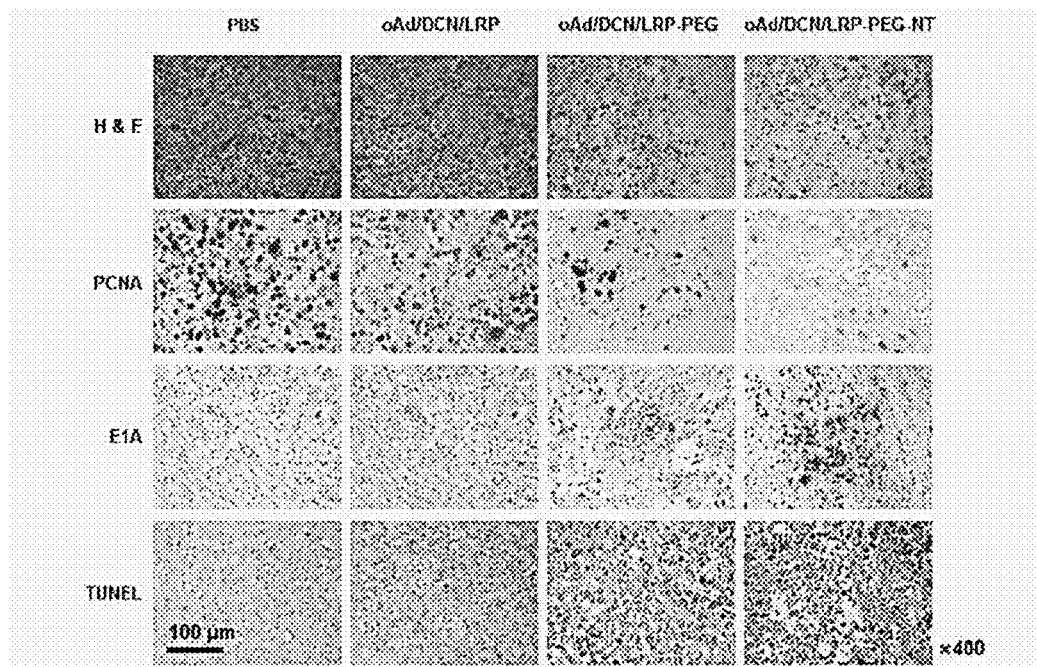

[FIG. 17]
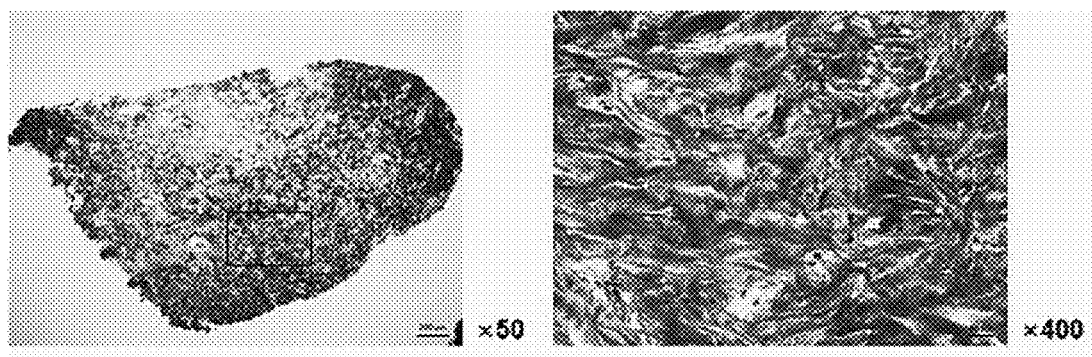
[FIG. 18]
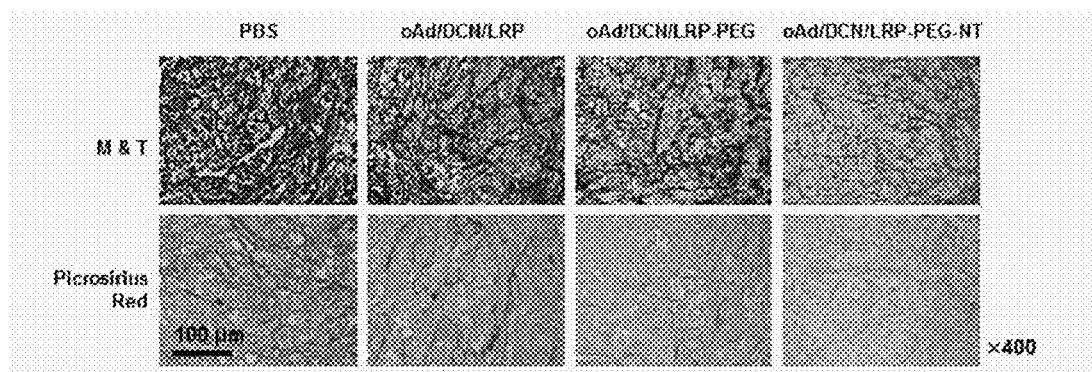

[FIG. 21A]
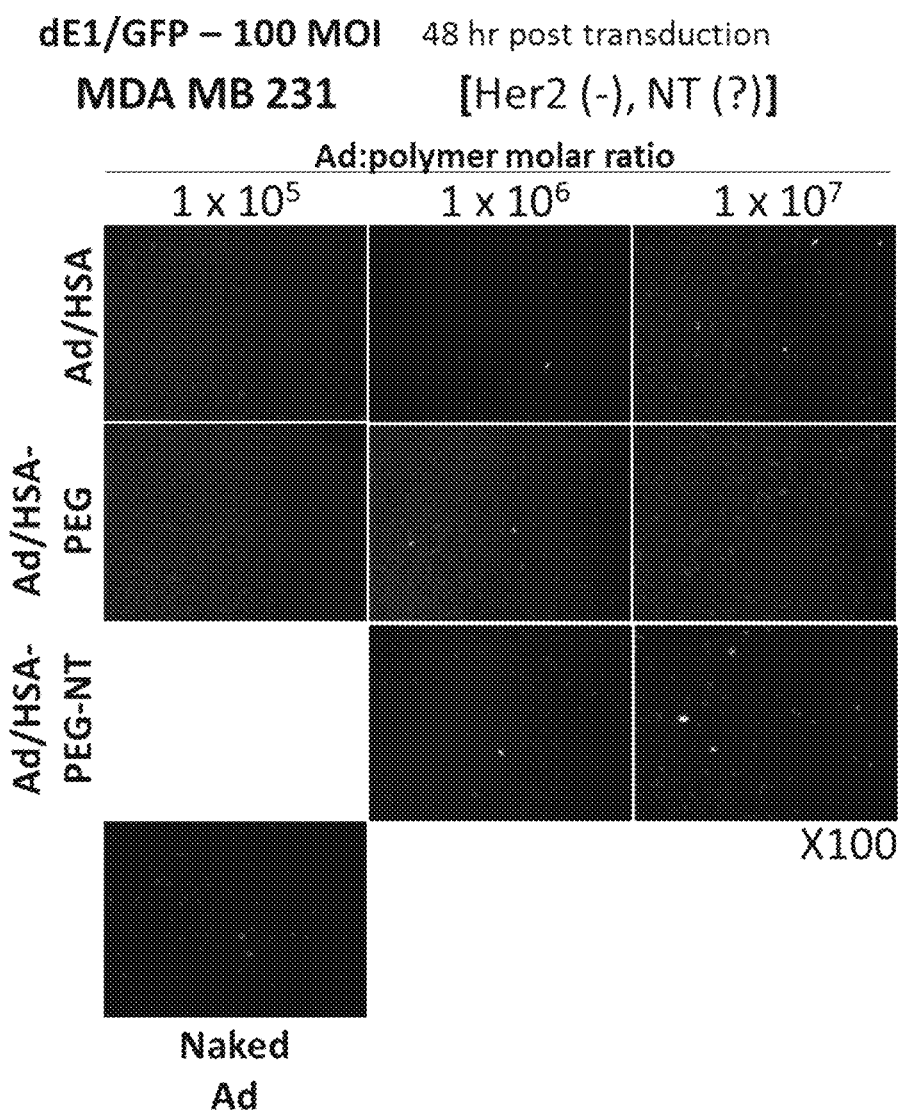

[FIG. 21B]
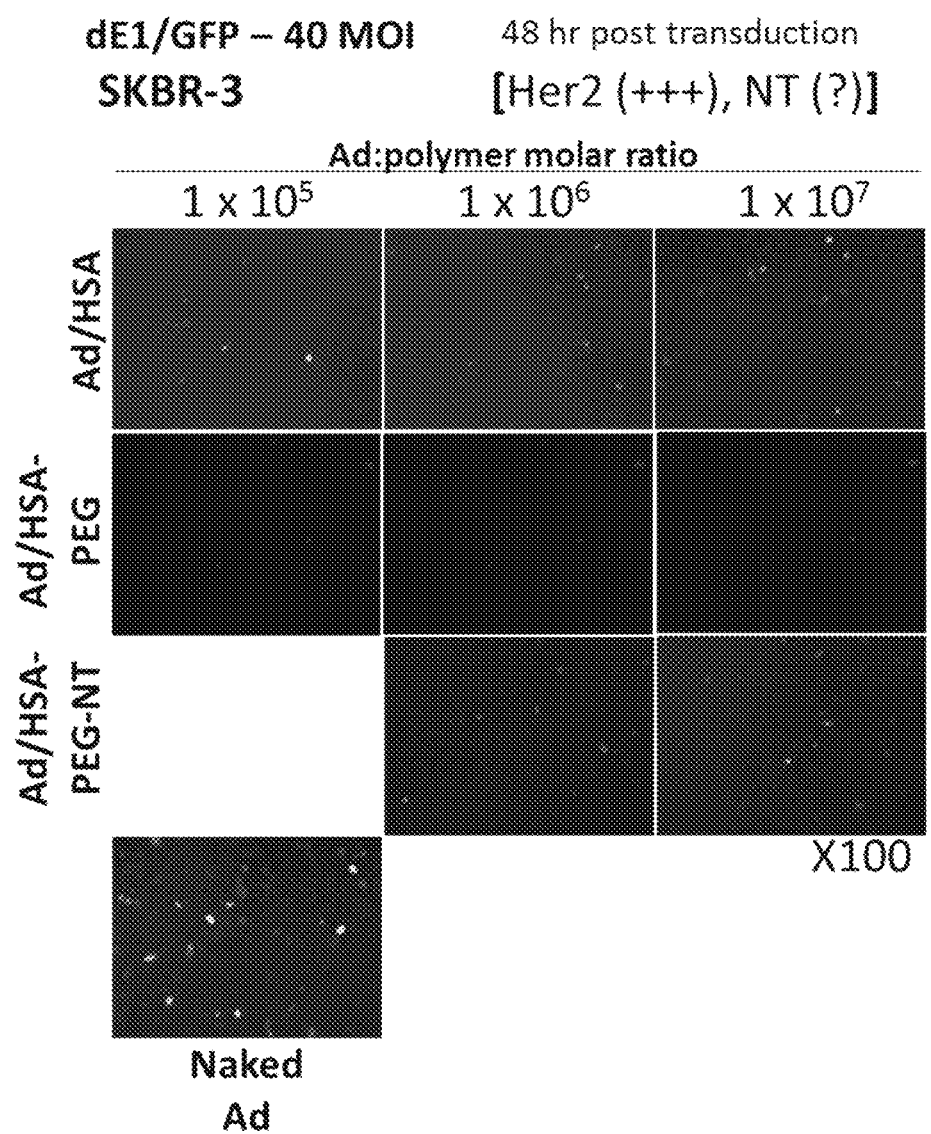

[FIG. 21C]
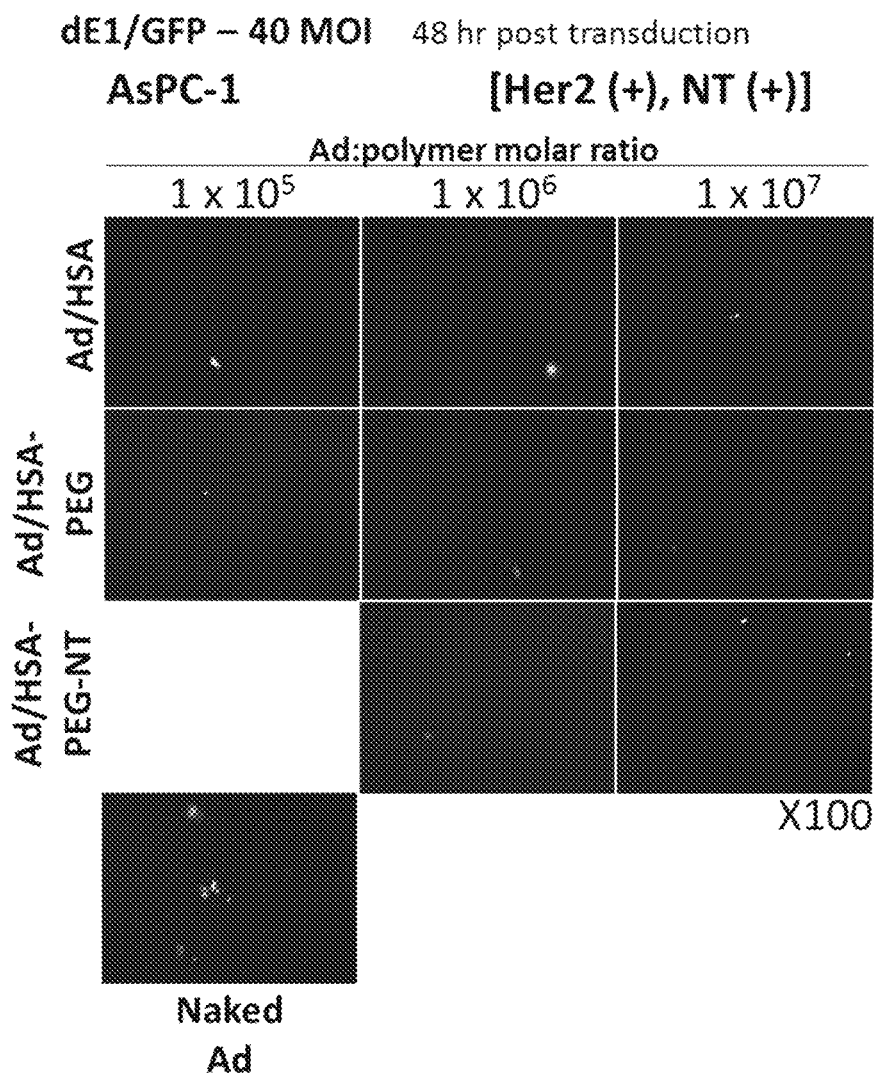

[FIG. 21D]
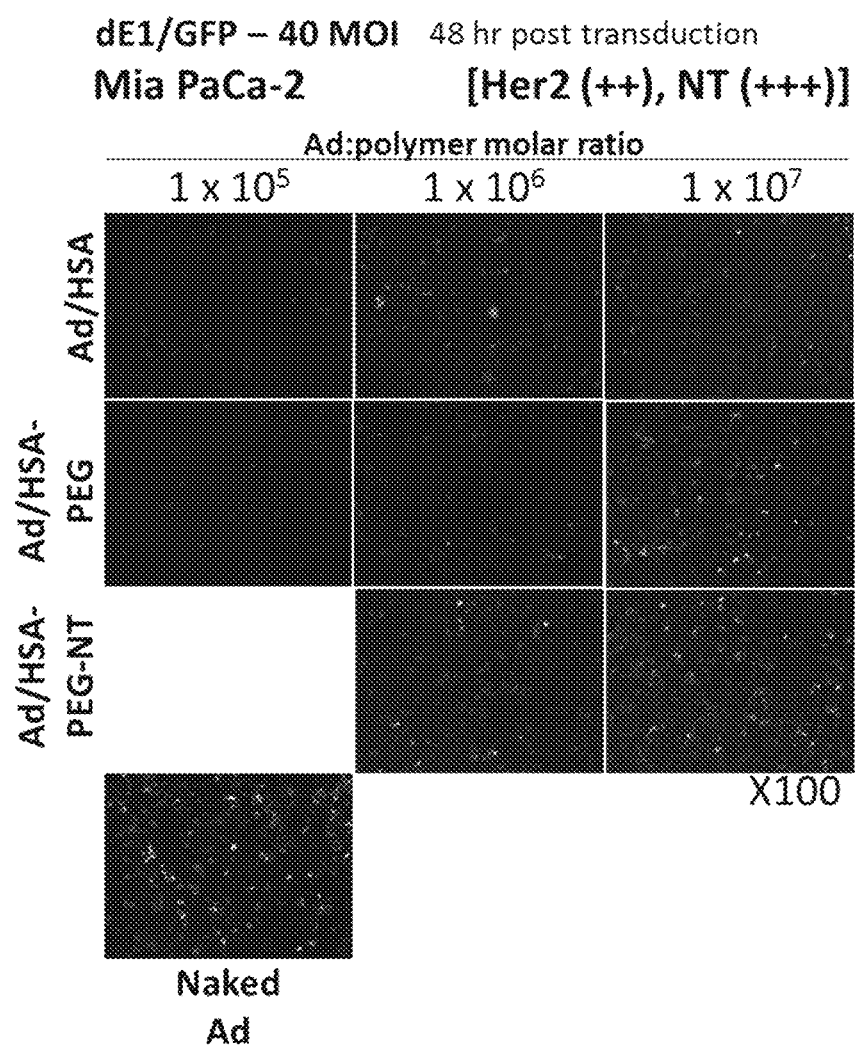

[FIG. 21E]
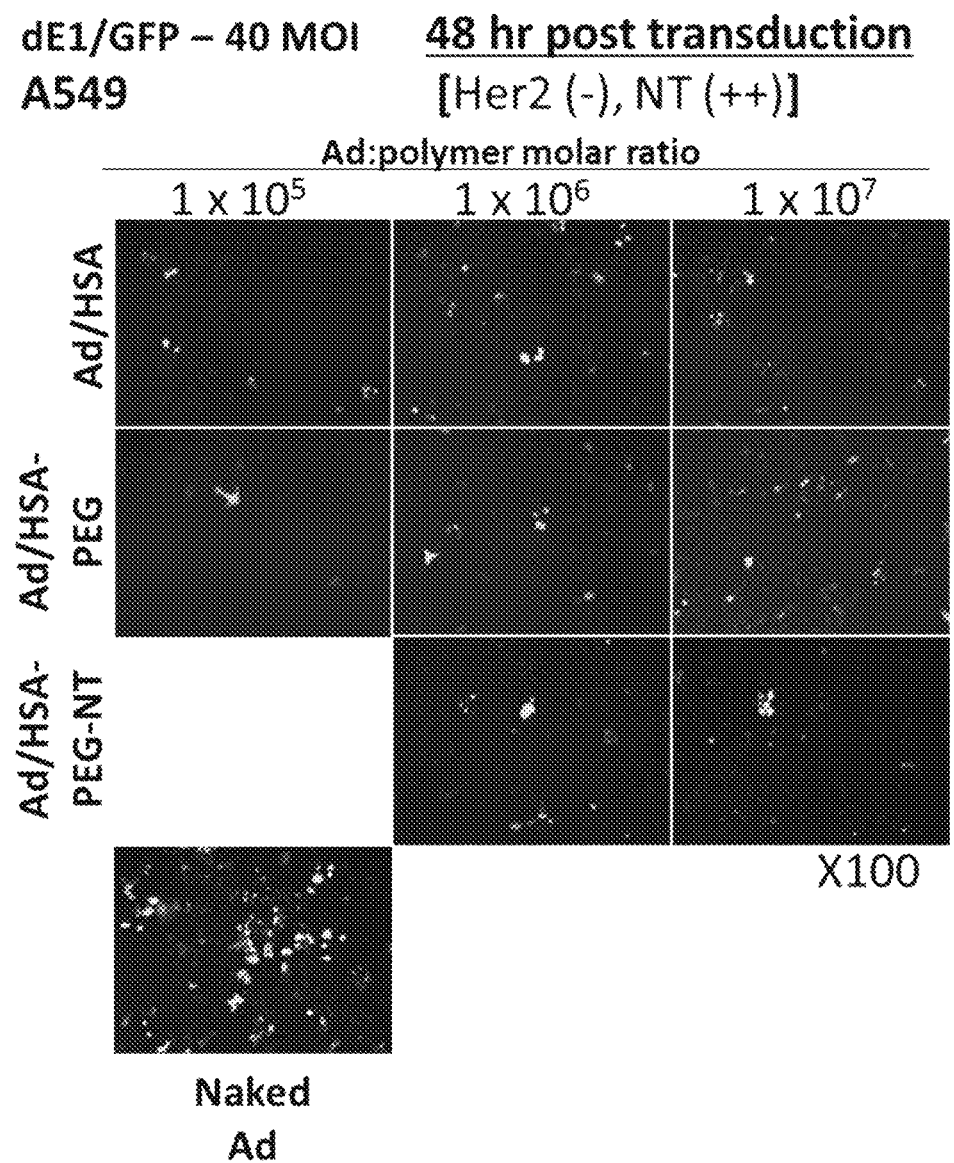

[FIG. 22A]
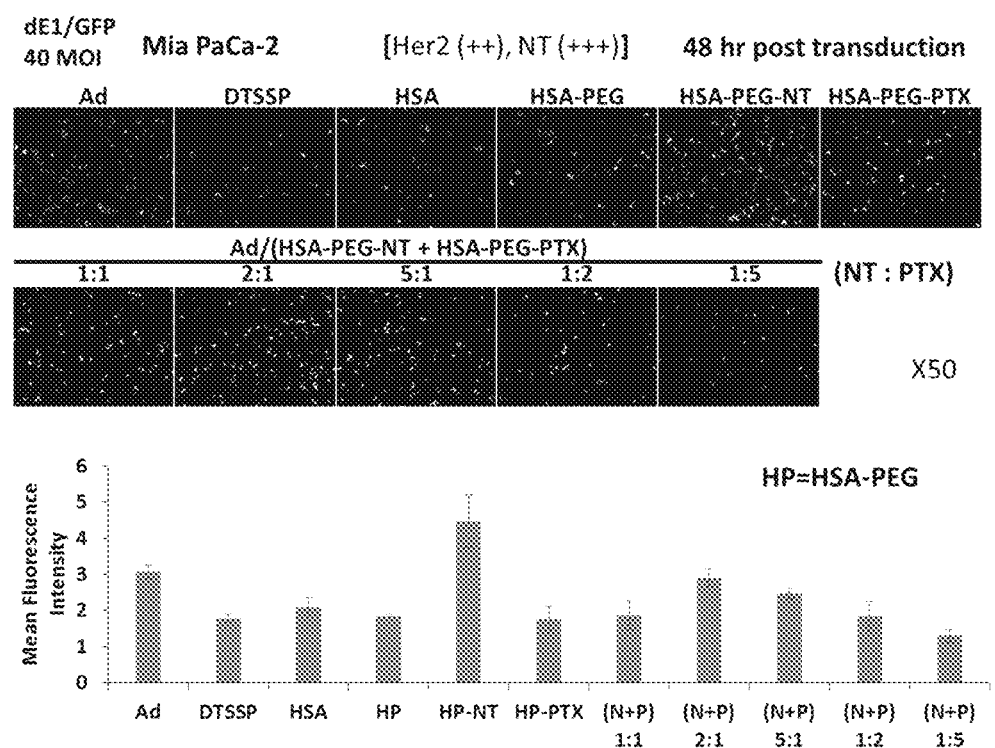

[FIG. 22B]
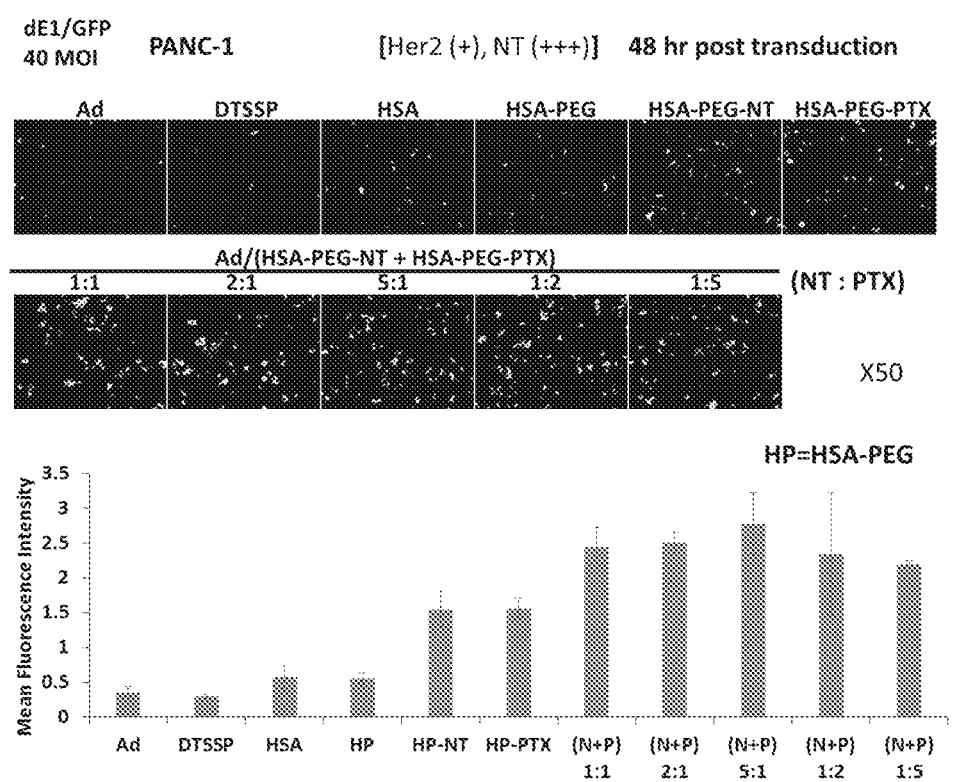

[FIG. 22C]
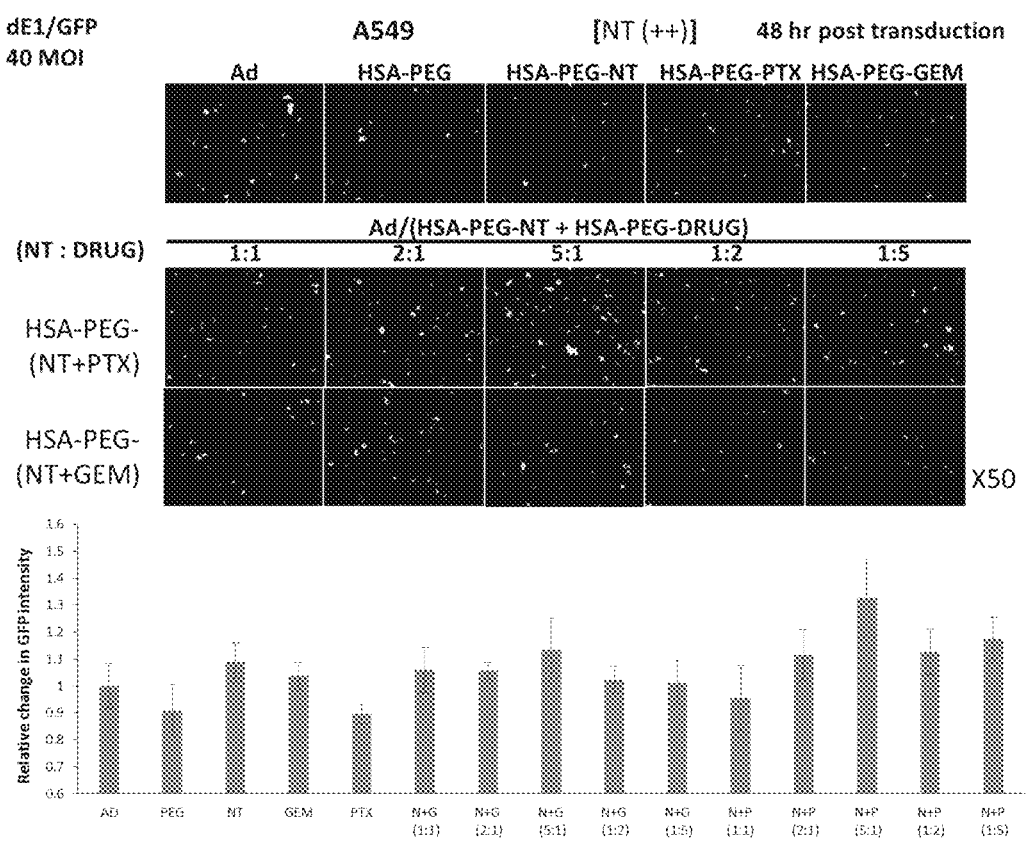
[FIG. 22D]
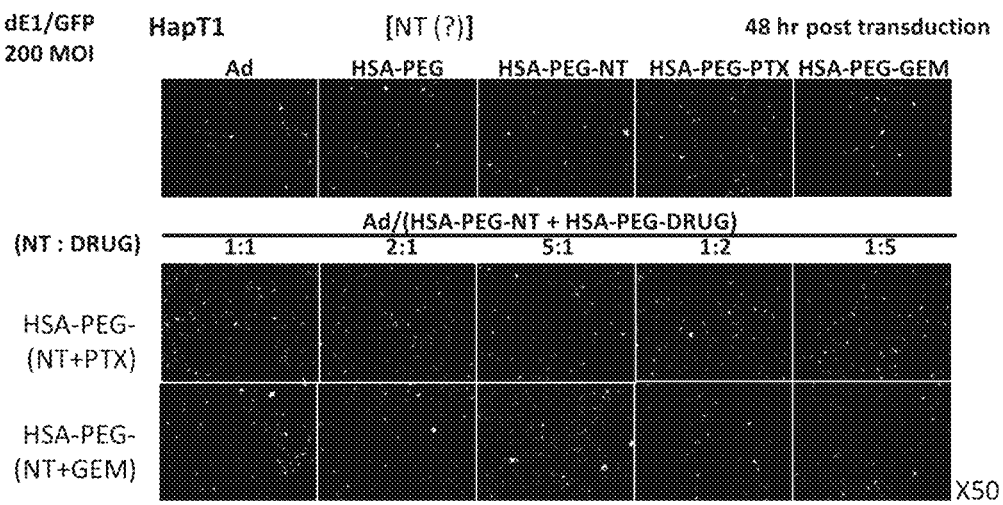

SEQUENCE LISTING

```
<160> NUMBER OF SEQ ID NOS: 3

<210> SEQ ID NO 1
<211> LENGTH: 14
<212> TYPE: PRT
<213> ORGANISM: Artificial
<220> FEATURE:
<223> OTHER INFORMATION: synthetic

<400> SEQUENCE: 1

Cys Glu Leu Tyr Glu Asn Lys Pro Arg Arg Pro Tyr Ile Leu
1               5                   10

<210> SEQ ID NO 2
<211> LENGTH: 7
<212> TYPE: PRT
<213> ORGANISM: Artificial
<220> FEATURE:
```

<223> OTHER INFORMATION: synthetic

<400> SEQUENCE: 2

Cys Arg Arg Pro Tyr Ile Leu
1               5

<210> SEQ ID NO 3
<211> LENGTH: 1905
<212> TYPE: DNA
<213> ORGANISM: Artificial
<220> FEATURE:
<223> OTHER INFORMATION: synthetic

<400> SEQUENCE: 3

| | |
|---|---|
| atgtctgcac ttctgatcct agctcttgtt ggagctgcag ttgctgacta caaagacgat | 60 |
| gacgacaagg gatccatggc tacgattgta gttggaggct ggaggatgc agctgcggtg | 120 |
| gactttgtgt ttagtcatgg cttgatatac tggagtgatg tcagcgaaga agccattaaa | 180 |
| cgaacagaat ttaacaaaac tgagagtgtg cagaatgttg ttgtttctgg attattgtcc | 240 |
| cccgatgggc tggcatgtga ttggcttgga gaaaaattgt actggacaga ttctgaaact | 300 |
| aatcggattg aagtttctaa tttagatgga tctttacgaa aagttttatt ttggcaagag | 360 |
| ttggatcaac ccagagctat tgccttagat ccttcaagtg ggttcatgta ctggacagac | 420 |
| tggggagaag tgccaaagat agaacgtgct ggaatggatg gttcaagtcg cttcattata | 480 |
| ataaacagtg aaattactg gccaaatgga ctgactttgg attatgaaga caaaagctt | 540 |
| tattgggcag atgcaaaact taatttcatc cacaaatcaa atctgatgg aacaaatcgg | 600 |
| caggcagtgg ttaaaggttc ccttccacat ccttttgcct tgacgttatt tgaggacata | 660 |
| ttgtactgga ctgactggag cacacactcc attttggctt gcaacaagta tactggtgag | 720 |
| ggtctgcgtg aaatccattc tgacatcttc tctcccatgg atatacatgc cttcagccaa | 780 |
| cagaggcagc caaatgccac aaatccatgt ggaattgaca atggggttg ttcccatttg | 840 |
| tgtttgatgt ctccagtcaa gccttttat cagtgtgctt gccccactgg ggtcaaactc | 900 |
| ctggagaatg gaaaaacctg caaagatggt gccacagaat tattgctttt agctcgaagg | 960 |
| acagacttga gacgcatttc tttggataca ccagatttta gacattgt tctgcagtta | 1020 |
| gaagacatcc gtcatgccat tgccatagat tacgatcctg tggaaggcta catctactgg | 1080 |
| actgatgatg aagtgagggc catacgccgt tcatttatag atggatctgg cagtcagttt | 1140 |
| gtggtcactg ctcaaattgc ccatcctgat ggtattgctg tggactgggt tgcacgaaat | 1200 |
| ctttattgga cagacactgg cactgatcga atagaagtga caaggctcaa tgggaccatg | 1260 |
| aggaagatct tgatttcaga ggacttagag aaccccggg ctattgtgtt agatcccatg | 1320 |
| gttgggtaca tgtattggac tgactgggga gaaattccga aaattgagcg agcagctctg | 1380 |
| gatggttctg accgtgtagt attggttaac acttctcttg gttggccaaa tggtttagcc | 1440 |
| ttggattatg atgaaggcaa atatactgg ggagatgcca aaacagacaa gattgaggtt | 1500 |
| atgaatactg atggcactgg gagacgagta ctagtggaag acaaaattcc tcacatattt | 1560 |
| ggatttactt tgttgggtga ctatgtttac tggactgact ggcagaggcg tagcattgaa | 1620 |
| agagttcata aacgaagtgc agagagggaa gtgatcatag atcagctgcc tgacctcatg | 1680 |
| ggcctaaagg ctacaaatgt tcatcgagtg attggttcca accctgtgc tgaggaaaac | 1740 |
| gggggatgta gccatctctg cctctataga cctcagggcc ttcgctgtgc ttgccctatt | 1800 |

```
ggctttgaac tcatcagtga catgaagacc tgcattgtcc cagaggcttt ccttttgttt    1860
tcacggagag cagatatcag acgaatttct ctggaaacaa acaat                    1905
```

ADENOVIRUS COMPLEX FOR GENE DELIVERY AND GENE IHERAPY

CROSS-REFERENCE TO RELATED APPLICATIONS

This application claims priority to and is a Continuation-In-Part of PCT/KR2016/011437 (WO2017/065497), filed on Oct. 12, 2016 entitled "ADENOVIRUS COMPLEX FOR GENE TRANSFER AND GENE THERAPY", which application claims priority to and the benefit of Korean Patent Application No. 10-2015-0142434, filed on Oct. 12, 2015, the disclosures of which are incorporated herein by reference in their entirety. Any disclaimer that may have occurred during the prosecution of the above-referenced applications is hereby expressly rescinded, and reconsideration of all relevant art is respectfully requested.

SEQUENCE STATEMENT

Incorporated by reference herein in its entirety is the Sequence Listing entitled "0338_131CIP," created Apr. 12, 2018, size of 4 kilobytes.

TECHNICAL FIELD

The present invention relates to an adenovirus complex which can be utilized for gene delivery and gene therapy by targeting neurotensin receptors.

BACKGROUND

Pancreatic cancer has been known to be very aggressive, malignant and difficult to cure. Although the incidence of pancreatic cancer is lower than those of other carcinomas, the pancreatic cancer is the fourth most common cause of death by cancer[1]. Since the pancreatic cancer is non-specific, has early symptoms that appear later and metastasizes early, according to the report by the U.S. National Cancer Institute, the 5-year survival rate of all patients diagnosed with pancreatic cancer during 2002 to 2008 is 5.8%, and 90% of almost all patients die within a year after the diagnosis. Thus, the prognosis of the patients with pancreatic cancer is very poor[2, 3].

The poor prognosis of conventional methods for treating pancreatic cancer including immunotherapy, chemotherapy and radiation therapy is due to the abnormal and excessive formation of the extracellular matrix (ECM) that induces very high connective tissue formation around the tumor cells[4-7]. In pancreatic cancer, almost 90% of the entire tumor volume consists of the pancreatic matrix and ECM, and serves as the first obstacle to efficient dispersion of therapeutic agents into tumor tissue[8]. Further, recent studies have revealed that ECM-promoting components such as collagen type I become promoting factors for tumor growth, drug resistance and metastasis[9, 10]. Because of such a disorder and limit of conventional therapies in treatment of pancreatic cancer, a new therapeutic modality for reducing pancreatic cancer by targeting ECM to improve the clinical result of the treatment of pancreatic cancer.

Adenovirus (Ad)-mediated gene therapy is a promising cancer treatment strategy, which is well-proven by articles, due to excellent and potent in vivo gene delivery. Particularly, oncolytic adenoviruses (oAds) have advantageous features for cancer gene therapy such as auto-proliferation in tumors, lysis of infected cancer cells and secondary infection of adjacent cells. An oAd expressing-gene therapy has been widely researched because it is able to induce cancer-selective expression and amplification of a specific gene and secondary infection of cancer cells through viral replication in a target site. However, with wild-type Ads (naked Ads) alone, there are significant limitations in the treatment of late-stage metastatic cancer that extensively spreads. To completely remove cancer that widely spreads in a host, systemic Ad administration is required, but such an approach faces major obstacles. Particularly, naked Ads have high immunogenicity and induce considerable antiviral immune responses, thereby rapidly removing Ads from blood using Ad-specific neutralizing antibodies (Abs), and other blood components such as platelets and red blood cells[13]. In addition, $\alpha V\beta 5$- and coagulation factor X-mediated Ad uptake into both Kupffer cells and hepatic cells leads to non-specifically absorption of Ads in the liver, low tumor target efficiency and severe hepatotoxicity[14, 15]. To overcome the limitations of oAd for clinical treatment, a specifically-designed Ad hybrid system in which viral and non-viral vectors are combined is required[18, 19].

The combination of the viral and non-viral vectors may be divided into two types of methods involving either a physical action or chemical conjugation. Both methods can be used to reduce immunogenicity and hide Ad native tropism, which is advantageous in vivo[20]. However, a physically-binding Ad nanocomplex is not ideal for systemic administration due to a non-specific charge interaction between a cationic polymer and an anionic serum protein, which may cause rapid degradation and structural instability in blood, thereby promoting coagulation[21]. Chemically-conjugated Ads may form a more stable nanocomplex which can endure blood circulation, hide the native tropism of an Ad for liver tissue, and thus can reduce an antiviral immune response.

PEGylation of Ads, as a notable example, has been used to protect Ads from protein hydrolysis and host-immune responses since the late 1990s[23-26]. However, such a protection method by PEG may block effective internalization of Ads into host cells due to the masking of endogenous fibers that can inhibit interactions with CAR, thereby reducing Ad entry efficiency[18, 21].

Therefore, since there are still many limits in clinical application of gene delivery and gene therapy using chemically-modified Ads, the development of an Ad complex in which Ads are present for a long time in vivo while maintaining a therapeutic capability, and which does not disappear in a blood circulation environment and has a therapeutic effect due to excellent intracellular intake of Ads without immune responses and side effects such as hepatotoxicity, still remains a challenge in this field.

SUMMARY OF THE INVENTION

Therefore, the inventors of the present invention designed targeting moiety-conjugated PEG for inducing the tissue-specific delivery of Ads to overcome the limitations of gene therapies using Ads, caused by instability of Ads, high immunogenicity and low gene delivery efficiency in vivo. The inventors of the present invention provide a PEGylated Ad complex in which an Ad capsid is coated with the targeting moiety-conjugated PEG to reduce the immunogenicity of Ads and increase tissue specificity. The inventors of the present invention confirmed that the complex can obtain excellent efficiency in introducing a gene in cells and an increase in therapeutic effect due to improved stability and target specificity of the complex, and at the same time, solve the problem of side effects by decreasing the immunogenicity of Ads and the induction of hepatotoxicity, and thus the present invention was completed.

The present invention provides a gene delivery system, which comprises an Ad, polyethylene glycol (PEG) and a neurotensin receptor-specific binding peptide (NT), and a composition for gene delivery, which comprises the same.

In addition, the present invention provides a complex for gene therapy, which comprises an Ad, PEG and a neurotensin receptor-specific binding peptide (NT).

In addition, the present invention provides a pharmaceutical composition, which comprises a therapeutically effective amount of the complex for gene therapy.

In addition, the present invention provides a method for treating a subject, which comprises administering a pharmaceutically effective amount of a gene delivery system, a complex for gene therapy, a composition for gene delivery or a pharmaceutical composition to a subject in need of treatment.

In addition, the present invention provides a method for preparing a gene delivery system or a complex for gene therapy, which comprises conjugating an Ad with PEG.

An Ad complex of the present invention can have an excellent antitumor effect due to high intracellular gene delivery efficiency and target specificity caused by neurotensin receptor-specific binding, almost no hepatotoxicity and immunogenicity, and stability, and low loss in blood even in an in vivo environment due to low immunogenicity. Therefore, the complex of the present invention can be effectively used for gene therapy.

DESCRIPTION OF DRAWINGS

FIG. 1 is a diagram of the Ad structure used in an exemplary embodiment of the present invention.

FIG. 2 is a graph showing the result of the $^1$HNMR analysis for a PEG-neurotensin peptide (NT) conjugate prepared according to an exemplary embodiment of the present invention.

FIG. 3 is a graph showing the result of MLDI-TOF analysis for a PEG-neurotensin peptide (NT) conjugate prepared according to an exemplary embodiment of the present invention.

FIGS. 4A and 4B are graphs showing the results of confirming the gene delivery efficiency of a DTSSP crosslinker by concentration to establish the optimal conditions for preparing an Ad-PEG-NT complex.

FIG. 5A is a fluorescence microscope image showing GFP expression and FIG. 5B are graphs showing the gene delivery efficiency of the complex according to concentrations of a DTSSP crosslinker and PEG to establish the optimal conditions for preparing the Ad-PEG-NT complex.

FIGS. 6A, 6B and 6C are graphs confirming the size distribution and surface charge of the Ad-PEG-NT complex prepared according to an exemplary embodiment of the present invention.

FIGS. 7A, 7B, 7C, 7D, 7E, 7F and 7G are graphs showing the results of confirming the expression levels of neurotensin receptors in various cell lines.

FIGS. 8A and 8B are images showing the results of confirming neurotensin receptor-specific intracellular introduction efficiency of the Ad complex prepared according to an exemplary embodiment of the present invention.

FIG. 9 is a graph and image showing the result of confirming whether the intracellular delivery of the Ad complex prepared according to an exemplary embodiment of the present invention is due to neurotensin receptor-specific binding.

FIGS. 10A, 10B, 10C, 10D and 10E are the graphs showing results of confirming the cancer cell killing ability of the Ad complex prepared according to an exemplary embodiment of the present invention.

FIGS. 11A, 11B, 11C, 11D and 11E are the graphs showing the results of confirming a virus production ability of the Ad complex prepared according to an exemplary embodiment of the present invention.

FIGS. 12A and 12B show immune responses induced by the Ad complex prepared according to an exemplary embodiment of the present invention, in which FIG. 12A is a graph showing the result of confirming an innate immune response, and FIG. 12B is a graph showing the result of confirming an adaptive immune response.

FIG. 13 is a graph showing the result of analyzing a pharmacokinetic characteristic of the Ad complex prepared according to an exemplary embodiment of the present invention.

FIGS. 14A, 14B and 14C show the results of confirming antitumor effects in pancreatic cancer orthotopic models, caused by the Ad complex prepared according to an exemplary embodiment of the present invention.

FIGS. 15A, 15B, 15C and 15D show the results of confirming in vivo distribution and hepatotoxicity per organ of the Ad complex prepared according to an exemplary embodiment of the present invention.

FIG. 15E shows the result of confirming whether the Ad complex prepared according to an exemplary embodiment of the present invention remains in liver tissue.

FIG. 16 shows the result of confirming an antitumor effect of the Ad complex prepared according to an exemplary embodiment of the present invention.

FIG. 17 is an image showing the distribution of collagen overexpressed in human pancreatic cancer tissue.

FIG. 18 shows the result of confirming a change in distribution of collagen in tumor tissue according to administration of the Ad complex prepared according to an exemplary embodiment of the present invention.

FIGS. 21A, 21B, 21C, 21D and 21E show the result of transduction efficacy of Ad/HSA-PEG-neurotensin receptor-specific binding peptides (NT) conjugates. In the NT and HER2 indications, the symbol "−" and "+" indicate the level of expression of receptors, such as Neurotensin (NT) and HER2, in the corresponding cell lines. The symbol "+" indicates low expression of the corresponding receptor, "++" indicates higher expression of the corresponding receptor than average, and "+++" indicates the highest overexpression of the corresponding receptor in cell lines. The symbol "−" means that the corresponding receptor is not expressed in the cell line. The symbol "?" means that the expression of the corresponding receptor was not known in the cell line.

FIGS. 22A, 22B, 22C and 22D show the result of transduction efficacy of Ad/(HSA-PEG-NTs+HSA-PEG-DRUGs). In the NT and HER2 indications, the symbol "−" and "+" indicate the level of expression of receptors, such as Neurotensin (NT) and HER2, in the corresponding cell lines. The symbol "+" indicates low expression of the corresponding receptor, "++" indicates higher expression of the corresponding receptor than average, and "+++" indicates the highest overexpression of the corresponding receptor in cell lines. The symbol "−" means that the corresponding receptor is not expressed in the cell line. The symbol "?" means that the expression of the corresponding receptor was not known in the cell line.

DETAILED DESCRIPTION OF THE INVENTION

Figure 19:
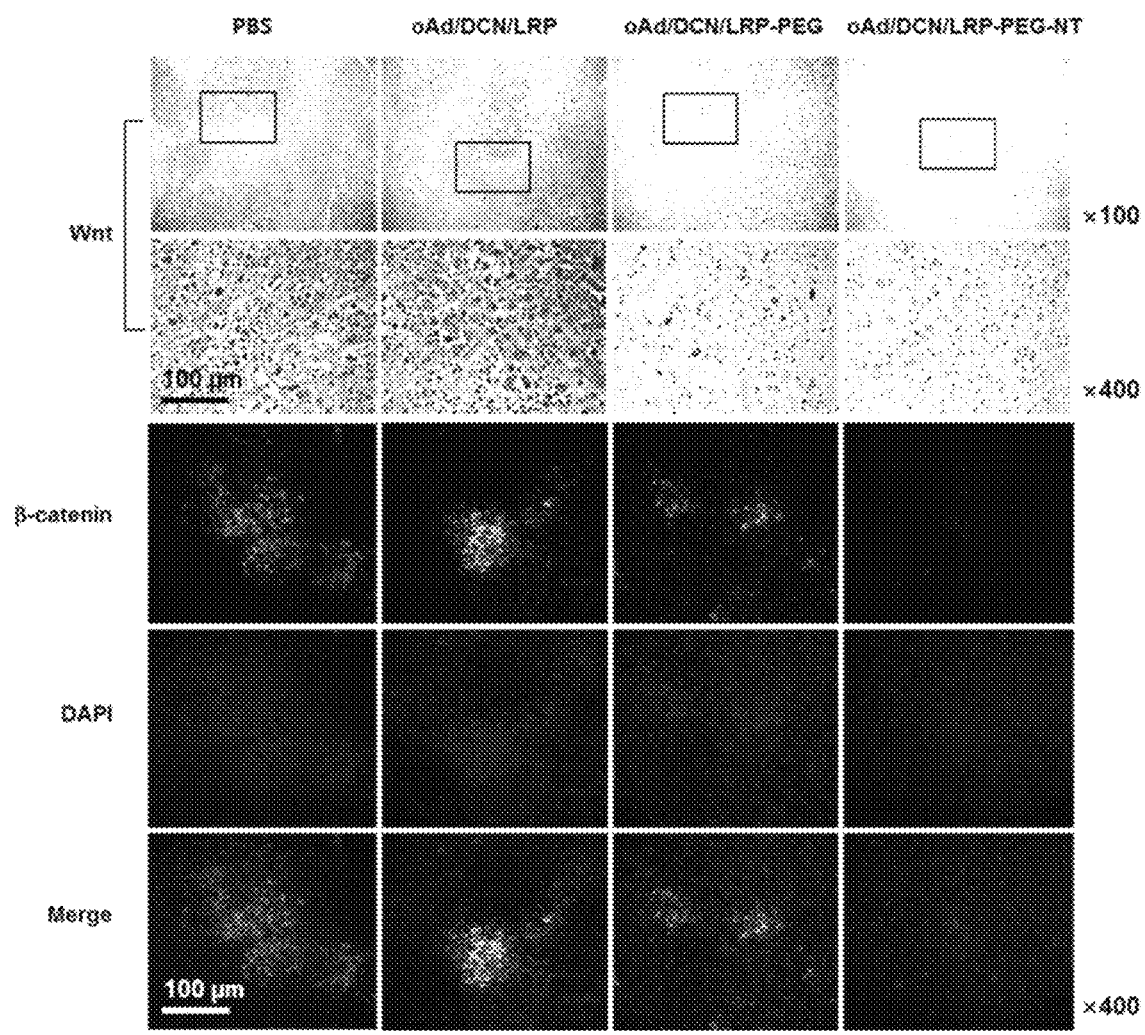
FIG. 19 shows the result of confirming changes in Wnt and β-catenin expression in tumor tissue according to administration of the Ad complex prepared according to an exemplary embodiment of the present invention.

The present invention relates to an Ad complex which comprises a biocompatible polymer and a ligand specifically binding to a neurotensin receptor, and more specifically, an Ad complex including an Ad, PEG and a neurotensin receptor-specific binding peptide (NT).

In addition, the present invention provides a method for preparing the Ad complex.

The Ad complex may be a gene delivery system in order to deliver a target gene in cells.

The Ad complex may be a complex for gene therapy, which comprises a target gene to express a gene in cells.

Hereinafter, the present invention will be described in further detail.

The present invention provides an Ad complex, which comprises an Ad, PEG and a neurotensin receptor-specific binding peptide (NT).

The term "Ad complex" used herein refers to binding between an Ad used as a gene delivery vector and components which are chemically or physically different from the Ad The "adeno virus (Ad)" is used as a gene delivery vector due to a moderate genome size, easy manipulation, a high titer, a wide range of target cells and high infectibility. Each of both ends of the genome comprises a 100 to 200 bp inverted terminal repeat (ITR), which is a cis-element necessary for DNA replication and packaging. E1 regions (E1A and E1B) of the genome encode proteins regulating transcription and the transcription of a host cell gene. The E2 regions (E2A and E2B) encode proteins involved in viral DNA replication.

Among currently-developed Ad vectors, an E1 region-deleted replication-deficient Ad is widely used. Meanwhile, an E3 region is removed from a conventional Ad vector and thus provides a foreign gene-insertion site (Thimmappaya, B. et al., *Cell*, 31:543-551(1982); and Riordan, J. R. et al., *Science*, 245:1066-1073(1989)). Meanwhile, a target nucleotide sequence to be delivered into cells is specifically inserted into the deleted E1 region (the E1A region and/or the E1B region, and preferably the E1B region) or E3 region, and more specifically, into the deleted E1 region.

The meaning of the term "deletion" used herein with respect to a genomic sequence comprises not only partially deletion of the corresponding sequence but also complete deletion of the corresponding sequence.

In addition, since an Ad may package approximately 105% of a wild-type genome, approximately 2 kb of genetic information may be additionally packaged (Ghosh-Choudhury et al., *EMBO J.*, 6:1733-1739(1987)). Therefore, the above-mentioned foreign sequence inserted into the Ad may be additionally bound to the Ad genome. The Ads have 42 different serotypes and A-F subgroups. Among these, Ad type 5 comprised in Subgroup C is the most suitable starting material to obtain an Ad vector of the present invention. Biochemical and genetic information on the Ad type 5 is well known. The foreign gene delivered by the Ad is replicated in the same manner as an episome and has very low genetic toxicity with respect to a host cell.

The term "neurotensin receptor-specific binding peptide (NT)" refers to a ligand that can specifically bind to neurotensin receptor 1 (NTR). Neurotensin receptor 1 is one of the receptors overexpressed in cancer cells, and particularly, a highly cancer-selective marker which is significantly overexpressed in pancreatic cancer, breast cancer, and head & neck cancer cells, and not present or rarely expressed in normal pancreatic cells[33].

The peptide (NT) is not limited in type and may comprise a base sequence of SEQ ID NO: 1 or 2, and more specifically consists of the base sequence. As the Ad complex of the present invention comprises a neurotensin peptide (NT) specifically binding to a neurotensin receptor, the Ad complex has high targetability for cancer cells, and particularly, tumor cells overexpressing a neurotensin receptor (NTR), low non-specific uptake of viruses into the liver, and excellent gene delivery efficiency to a target site.

The NTR-specific binding peptide may be a PEG-binding (conjugated) peptide. Specifically, the NTR-specific binding peptide may be conjugated to the end of PEG and thus may be present on the outermost surface of the complex of the present invention. When the NTR-specific binding peptide is present on the surface of the complex according to the present invention, it has excellent delivery efficiency to target cells or tissues.

According to an exemplary embodiment of the present invention, it was experimentally confirmed that the complex including the NTR-specific binding peptide has higher gene delivery efficiency with respect to neurotensin receptor-expressing cells than that of a complex that does not contain the peptide.

Therefore, the Ad complex of the present invention may be specific to overexpression of a neurotensin receptor.

The "polyethylene glycol (PEG)" may be one of the biocompatible polymers, and the PEG may be conjugated with an Ad. Specifically, the PEG may be bound (conjugated) to an Ad capsid surface, and such binding may be formed by PEGylation. More preferably, the PEG may be bound with the NTR-specific binding peptide at one end and may be bound with the Ad at the other end.

The binding may be performed using a crosslinker, and the crosslinker used in the present invention may be any one that can bring about binding between an amine group present in an Ad capsid and PEG without limitation. In one example, the crosslinker may be, but is not limited to, 3,3'-dithiobis(sulfosuccinimidyl propionate) (DTSSP) or dithiobis(succinimidyl propionate) (DSP).

According to an exemplary embodiment of the present invention, the crosslinker may be DTSSP. When DTSSP is used as a crosslinker, for binding between PEG and an Ad, $1 \times 10^5$ mol or more of PEG and $1 \times 10^5$ mol or more of a DTSSP crosslinker may be comprised with respect to 1 mol of the Ad. In the Ad complex prepared by satisfying the above-mentioned range, since a capsid region is entirely masked by binding 80% or more of amine groups of the virus capsid with PEG, immunogenicity may be significantly reduced, the average particle size of the complex may be maintained at 100 to 200 nm, and therefore the intracellular uptake efficiency of the complex is further improved.

The complex of the present invention may further comprise a target gene which is delivered into cells by the Ad.

The term "target gene" used herein refers to all and a part of a gene, and may be delivered into cells for treatment, prevention or diagnosis of a disease. The target gene is preferably a therapeutic gene (polynucleotide sequence) exhibiting a therapeutic or preventive effect in expression in cells. The type of the gene is not limited to the type of target disease as long as the gene may be comprised in the complex of the present invention. The complex of the present invention may comprise a separate promoter for the expression of a gene. In addition, the complex of the present invention may comprise one or more target genes.

Preferably, the gene is a cancer therapeutic gene that induces the death of cancer cells and ultimately degrades tumors, and comprises a tumor suppressor gene, an immune-related gene, an antigenic gene, a suicide gene, a cytotoxic gene, a cytostatic gene, a pro-apoptotic gene and an anti-angiogenic gene, but the present invention is not limited thereto.

The term "tumor suppressor gene" used herein refers to a nucleotide sequence which is expressed in target cells to suppress a tumor phenotype or to induce cell death. The tumor suppressor gene useful for the implement of the present invention comprises a p53 gene, an APC gene, a DPC-4/Smad4 gene, a BRCA-1 gene, a BRCA-2 gene, a WT-1 gene, a retinoblastoma gene (Lee et al., Nature, 1987, 329,642), an MMAC-1 gene, an adenomatous polyposis coil protein (U.S. Pat. No. 5,783,666), a deleted colon cancer (DCC) gene, an MMSC-2 gene, an NF-1 gene, a nasopharyngeal carcinoma suppressor gene located at chromosome 3p21.3 (Cheng et al. Proc. Nat. Acad. Sci, 95:3042-3047 (1998)), an MTS1 gene, a CDK4 gene, an NF-1 gene, an NF-2 gene and a VHL gene.

The term "immune-related gene" used herein refers to all genes regulating the expression of immune-related factors, for example, genes encoding cytokines (e.g., interferon-$\alpha$, -$\beta$, -$\delta$ and -$\gamma$), interleukins (e.g., IL-1, IL-2, IL-4, IL-6, IL-7, IL-10, IL-12, IL-17, IL-18, IL-19, IL-20 and IL-23) and colony stimulating factors (e.g., GM-CSF and G-CSF); chemokine groups (monocyte chemotactic protein 1 (MCP-1), MCP-2, MCP-3, MCP-4, macrophage inflammatory protein 1$\alpha$ (MIP-1$\alpha$), MIP-1$\beta$, MIP-1$\gamma$, MIP-3$\alpha$, MIP-3$\beta$, a chemokine (ELC), macrophage inflammatory protein 4 (MIP-4), macrophage inflammatory protein 5 (MIP-5), LD78$\beta$, RANTES, SIS-$\epsilon$ (p500), thymus and activation-regulated chemokine (TARC), eotaxin, 1-309, human protein HCC-1/NCC-2, human protein HCC-3, murine protein C10, etc.); and costimulatory factors (costimulatory factors: accessory molecules required for T cell activation such as B7.1 and B7.2).

The term "antigenic gene" used herein refers to a nucleotide sequence which expressed in target cells to produce a cell surface antigenic protein capable of being recognized in an immune system. Examples of such antigenic genes comprise a carcinoembryonic antigen (CEA), HER-2, a prostate specific antigen (PSA) and p53 (Levine, A., International Patent Application Publication No. WO94/02167). To facilitate recognition by the immune system, the antigenic gene may be bound to an MHC type I antigen.

The term "cytotoxic gene" used herein refers to a nucleotide sequence which is expressed in cells and exhibits a toxic effect. Examples of such cytotoxic genes comprise nucleotide sequences encoding *Pseudomonas* exotoxin, Ricin toxin, *Diphtheriae* toxin, etc.

The term "cytostatic gene" refers to a nucleotide sequence which is expressed in cells to suspend a cell cycle during the cell cycle. Examples of such cytostatic genes may comprise p21, a retinoblastoma gene, an E2F-Rb fusion protein gene, genes encoding cyclin-dependent kinase inhibitors (e.g., p16, p15, p18 and p19), and growth arrest specific homeobox (GAX) genes (WO 97/16459 and WO 96/30385), but the present invention is not limited thereto.

The term "pro-apoptotic gene" used herein refers to a nucleotide sequence which is expressed to induce programmed cell death. Examples of such pro-apoptotic genes comprise p53, Ad E3-11.6K (derived from Ad2 and Ad5) or Ad E3-10.5K (derived from Ads), Ad E4 gene, Fas ligand, TNF, TRAIL, a p53 gene, and a gene encoding a caspase.

The term "anti-angiogenic gene" used herein refers to a nucleotide sequence which is expressed to release an anti-angiogenic factor from a cell. Examples of the anti-angiogenic factors comprise angiostatin, a repressor of a vascular endothelial growth factor (VEGF) such as Tie 2 (PNAS, 1998, 95, 8795-800), and endostatin.

In addition, since many therapeutic genes that can be useful for treatment of various types of diseases are means for assisting an antitumor effect, they may be delivered by the Ad of the present invention, for example, a relaxin gene has been defined to be suitable for Ad gene therapy by the inventors, a nucleotide sequence encoding a Wnt3a/$\beta$-catenin signaling inhibitor (Wnt decoy protein) or a decorin gene is also a gene that can be delivered into cells by a gene delivery system.

The nucleotide sequence described above may be obtained from a DNA sequence databank such as GenBank.

According to an exemplary embodiment of the present invention, the gene may be a base sequence encoding a decorin gene and sLRP6E1E2, which is an agonist for blocking Wnt3a/$\beta$-catenin signaling. A complex for expressing the decorin gene and the Wnt3a/$\beta$-catenin signaling inhibitory protein (sLRP6E1E2) has excellent targetability with respect to pancreatic cancer cells overexpressing a neurotensin receptor in a peptide on the complex surface, the extracellular matrix overexpressed in pancreatic cancer is significantly reduced by the decorin gene comprised in the complex, and therefore an excellent cancer cell killing ability is exhibited.

In such an aspect, the complex of the present invention may be an oncolytic Ad complex, which expresses a decorin gene and a Wnt3a/$\beta$-catenin signaling inhibitory protein and is used for NTR-overexpressing and ECM-overexpressing tumor cell therapy, and the complex may further comprise a nucleotide sequence of another target gene as well as nucleotides encoding the decorin gene and the Wnt3a/$\beta$-catenin signaling inhibitory protein. The oncolytic Ad complex for expressing the decorin gene and the Wnt inhibitory protein may reduce ECMs such as a collagen present in pancreatic cancer at an abnormally excessive amount and may be particularly effective in treatment of NTR-overexpressing and ECM-overexpressing tumor cells due to an excellent replication ability in tumors. Particularly, due to abnormally-existing ECMs, other therapeutic components are not properly diffused, and thus it is difficult to treat tumor cells. Therefore, it is more significant that the complex of the present invention has an excellent therapeutic effect for the treatment of such carcinoma.

In one aspect of the present invention, the Ad complex may deliver a target gene derived from a foreign organism into cells, and in such an aspect, the complex of the present invention may be a gene delivery system.

The term "gene delivery system" used herein refers to a means for delivering a foreign gene to a part such as a target cell or tissue. The gene delivery system may be used while a target gene to be delivered is operably linked to the above-mentioned gene expression regulatory sequence. The term "operatively linked" used herein refers to functional binding between a gene expression regulatory sequence (e.g., a promoter, a signal sequence, or an array of transcription regulatory factor-binding sites) and a different nucleic acid sequence, and therefore, the regulatory sequence regulates the transcription and/or translation of the other nucleic acid sequence. A target gene operably linked to the gene expression regulatory sequence of the present invention is not particularly limited.

In another aspect of the present invention, the gene delivery system may be used along with a pharmaceutically acceptable adjuvant for gene therapy or treatment, and according to such an aspect, the present invention may provide a composition for gene delivery, which comprises the gene delivery system.

The composition for gene delivery may further comprise a component conventionally comprised in the art of the present invention for gene delivery.

In still another aspect of the present invention, the Ad complex is delivered into cancer cells, thereby having a direct cancer cell killing effect by the expression of a gene comprised in the Ad, and in such an aspect, the Ad complex of the present invention may be a complex for gene therapy.

The complex for gene therapy may further comprise a therapeutic gene.

According to an exemplary embodiment of the present invention, to measure target and therapeutic efficiency with respect to NTR-expressing pancreatic cancer cells in vitro and in vivo, the inventors prepared both PEG-NT cross-linked with non-replicating and cancer cell-specific replicating Ads, and proved that the Ads exhibit higher gene introduction efficiency in NTR-expressing pancreatic cancer cells. In addition, a complex capable of expressing both a decorin gene and a soluble Wnt decoy receptor (sLRP6E1E2) for maximizing a desired therapeutic effect in treatment of pancreatic cancer by degrading abnormal ECM and suppressing Wnt/β-catenin and TGF-β1 signaling was prepared, and it was experimentally confirmed that the complex is able to down-regulate ECM synthesis, chemical resistance and the epithelial-to-mesenchymal transition (EMT) in pancreatic cancer, and has an excellent pancreatic cancer treating effect.

The complex for gene therapy may further comprise chemical therapeutic drugs which are conjugated with PEG. The drugs may be included in the complex for gene therapy in a form conjugated with PEGs bound to the surface of the adenovirus, particularly the capsid of the adenovirus. The complex for gene therapy may comprise a neurotensin receptor-specific binding peptide (NT) and anti-cancer drugs at NT:PTX molar ratio from 0.1:1 to 10:1, preferably 1:1 to 6:1. When the complex of the present invention further comprises the chemical therapeutic drugs, the effect of gene therapy can be further improved.

The "chemical therapeutic drugs" may comprise all the drugs used in chemical therapeutics in the field of the present invention. Specifically, the anti-cancer drugs can be selected from the group consisting of comprise cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol (paclitaxel), transplatinum, 5-fluorouracil, vincristin, vinblastin, methotrexate, gemcitabine and the combination thereof, but the present invention is not limited thereto.

In yet another aspect of the present invention, the Ad complex may be used along with a pharmaceutically acceptable adjuvant for delivery for gene therapy or treatment, and according to such an aspect, the present invention may provide a pharmaceutical composition including the Ad complex.

The pharmaceutical composition may further comprise a therapeutic gene.

A pharmaceutical composition including the Ad complex of the present invention at a therapeutically effective amount may be applied regardless of the type of disease. Specifically, since the pharmaceutical composition including the complex of the present invention may be applied to various diseases according to a variety of pharmaceutically active ingredients additionally comprised, the pharmaceutical composition including the complex may be applied for various uses without limitation to the type of disease. The pharmaceutically active ingredient is not limited in type, and may be comprised in the composition along with the complex of the present invention or comprised in the composition while being comprised in the complex of the present invention. For example, the pharmaceutically active ingredient may be a therapeutic gene. Therefore, any type of pharmaceutical composition including a therapeutically effective amount of the complex of the present invention is comprised in the present invention regardless of the type of disease.

As described above, while the pharmaceutical composition of the present invention is not limited to the type of disease, the complex of the present invention has a characteristic specific to neurotensin-overexpressing tumor cells, and according to such an aspect, the pharmaceutical composition is preferably used in anticancer treatment. In this aspect, the pharmaceutical composition may be an anticancer (antitumor) pharmaceutical composition.

In addition, the composition may further comprise an active ingredient with anticancer or anti-inflammatory activity, in addition to the complex of the present invention.

The term "therapeutically effective amount" used herein refers to an amount sufficient for achieving the pharmaceutical effect.

A pharmaceutically acceptable carrier comprised in the composition of the present invention is conventionally used in formulation, and may be, but is not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate or mineral oil. The pharmaceutical composition of the present invention may further comprise a lubricant, a wetting agent, a sweetening agent, a flavoring agent, an emulsifier, a suspension and a preservative in addition to the above-mentioned components.

In yet another aspect of the present invention, the present invention provides a method for treating a subject, which comprises administering a pharmaceutically effective amount of the Ad complex or pharmaceutical composition to a subject in need of treatment.

The pharmaceutical composition of the present invention may be administered parenterally, for example, intravenously, intraperitoneally, intramuscularly, subcutaneously or locally. The pharmaceutical composition of the present invention may be administered intraperitoneally to treat ovarian cancer, and administered into a portal vein to treat liver cancer. The pharmaceutical composition may be directly injected into a tumor mass to treat breast cancer, and directly injected through an enema to treat colon cancer.

The term "pharmaceutically effective amount" used herein refers to an amount sufficient to treat the disease at a reasonable benefit/risk ratio applicable for medical treatment. A suitable dose of the pharmaceutical composition of the present invention may vary depending on factors such as a preparation method, an administration method, a patient's age, weight and sex, severity of disease symptoms, diet, administration time, an administration route, an excretion rate, and response sensitivity, and an effective dose for desired treatment may be easily determined and prescribed by an ordinarily skilled doctor. The pharmaceutical composition of the present invention comprises the Ad complex at $1\times10^1$ to $1\times10^{50}$ VP/ml, and typically, may be injected every other day. However, the specific dosage and the number of administrations may be changed in consideration of a patient's age, the severity of a disease, etc.

The term "subject" used herein comprises animals such as horses, sheep, pigs, goats, camels, antelopes and dogs, or humans, which have a disease whose symptoms can be alleviated by administration of the therapeutic composition according to the present invention. As the pharmaceutical composition of the present invention is administered to the subject, a disease may be effectively prevented and treated. The treating method according to the present invention may be a method of treating an animal except a human, but the present invention is not limited thereto. That is, if a human has a disease whose symptoms can be alleviated by administering the composition according to the present invention, the composition of the present invention may be sufficiently used even to treat a human disease.

The pharmaceutical composition of the present invention may be prepared by unit-dose packaging or multi-dose packaging after being formulated using a pharmaceutically acceptable carrier and/or excipient according to a method that can be easily implemented by those of ordinary skill in the art. Here, a dosage form of the pharmaceutical composition of the present invention may be a solution in an oil or aqueous medium, a suspension or an emulsion, an extract, a powder, a granule, a tablet or a capsule, and the pharmaceutical composition of the present invention may further comprise a dispersant or a stabilizer.

The pharmaceutical composition of the present invention may be used independently or in combination with other conventional chemical or radiation therapies, and such combination therapy may be used more effectively in cancer treatment. Chemical therapeutic drugs that can be used together with the composition of the present invention comprise cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin, and methotrexate. Radiation therapies that can be used together with the composition of the present invention comprise X-ray radiation and γ-ray radiation.

According to yet another aspect of the present invention, the present invention provides a method for preparing an Ad complex.

The preparation method comprises performing conjugation by a reaction of an Ad, PEG and a crosslinker.

In the conjugation step, the PEG reacted with the Ad may be conjugated with a neurotensin receptor-specific peptide at one end.

In the conjugation step, the Ad may be reacted with the PEG at a molar ratio (Ad:PEG) of 1 mol:$1\times10^5$ mol.

In the conjugation step, the Ad may be reacted with the crosslinker at a ratio of 1:$1\times10^5$ mol or more, or at 1:$1\times10^5$ mol or more to 3×$10^5$ mol or less.

Most preferably, based on 1 mol of the Ad, $1\times10^5$ mol or more of PEG and $1\times10^5$ mol or more of the crosslinker may be reacted. When the reaction is performed within the range, an Ad complex may have excellent neurotensin receptor-dependent targetability and may be stable.

Therefore, the present invention provides an Ad complex prepared by the above-described preparation method.

EXAMPLES

Hereinafter, the present invention will be described in further detail with respect to examples. These examples are only provided to more fully describe the present invention, and it is obvious to those of ordinary skill in the art that the scope of the present invention is not limited to these examples, according to the gist of the present invention.

Examples

1. Experimental Preparation and Statistical Analysis
1-1. Cell Culture

Human pancreatic cancer cell lines (PANC-1, MIA PaCa-2 and AsPC-1), a lung adenocarcinoma cell line (A549) and an Ad5 E1-transformed embryonic kidney cell line (HEK293) were purchased from the American Type Culture Collection (ATCC, Manassas, Va.). Human normal pancreatic cells (NPCs) were purchased from Applied Biological Materials Inc. (ABM, Richmond, Canada), and stored in a Prigrow I medium (ABM). The AsPC-1 cells were stored in RPMI-1640 (Gibco BRL, Grand Island, N.Y.), and the other cells were cultured in high concentration glucose Dulbecco's modified Eagle's media (DMEM, Gibco BRL) containing 10% fetal bovine serum (FBS, Gibco BRL) in a 37° C., 5% CO2 incubator. Pancreatic cancer tissues collected from a patient were obtained from the Hanyang University Medical School. The tumor tissues were subjected to immunohistochemistry according to the protocols approved by the Institutional Review Board of Hanyang University. All experiments related to human tissues were carried out in accordance with the principles of the Declaration of Helsinki.

1-2. Statistical Analysis

Results were expressed as mean±SD. Statistical significance was determined by the two-tailed Student T-test (SPSS 13.0 software; SPSS, Chicago, Ill.) and one-way analysis of variance (one-way ANOVA). The difference of *$P<0.05$, $P<0.01$, or *$P<0.001$ indicated statistical significance.

2. Structure of Ad and Preparation of PEG-NT
2-1. Structure of Ad

Neurotensin receptor-dependent delivery efficiency was confirmed using a green fluorescent protein (GFP)-expressing replication-deficient Ad (dE1/GFP). To manufacture oAd (oAd/DCN/LRP) whose proliferation is regulated by an HRE-E2F-mTERT (HEmT) promoter and which expresses a decorin gene (decorin, DCN) and sLRP6E1E2 (LRP) capable of suppressing Wnt3a/β-catenin signaling[38-40], a retinoblastoma-binding site-deleted Ad E1 shuttle vector (pDElsp1B/Rd19) with a mutated E1A and E1B 19 kDa site was used as a template plasmid. First, a pDElsp1B/HEmT-Rd19 Ad E1 shuttle vector was manufactured by inserting a HEmT promoter into pDElsp1B/Rd19. To insert a DCN expression cassette, the decorin gene was separated from pCA14/DCN using BglII and ligated with pDElsp1B/HEmT-Rd19, thereby preparing pDElsp1B/HEmT-Rd19/DCN Ad E1. For homologous recombination with linear Ad dE1-k35, a HEmT-Rd19-k35/DCN oAd plasmid was manufactured by transforming E. coli BJ5183 with an XmnI-treated pDElsp1B/HEmT-Rd19/DCN Ad E1 shuttle vector. Afterward, an LRP-expressing Ad E3 shuttle vector (pSP72dE3-LRP) was structured using a pCA14-LRP vector[36]. The newly-structured pSP72dE3-LRP was linearized with a DCN-expressing oAd vector (HEmT-Rd19-k35/DCN) in *E. coli* BJ5183, and was used to transform, thereby manufacturing an oAd/DCN/LRP oncolytic Ad. Suitable homologous recombinant Ad plasmid DNA was lysed with PacI, and transfected into 293 cells to manufacture oAd/DCN/LRP oAd. Replication-deficient dE1/GFP and replication-competent oAd/DCN/LRP were delivered to 293 cells and A549 cells, respectively, and purified using CsCl gradient centrifugation.

The number of viral particles (VPs) was calculated at 260 nm ($OD_{260}$) using a spectrophotometer. Here, the absorbance 1 ($OD_{260}=1$) corresponds to $1.1\times10^{12}$ VP/mL. Purified viruses were stored at $-8°$ C. until use.

2-2. Preparation of NT-Conjugated Polyethylene Glycol (PEG-NT)

A 1 µM solution was prepared by dissolving 3 mg of heterobifunctional PEG (Mal-PEG-$NH_2$, 3.5 kDa; JenKem Technology, Plano, Tex.) in an 1× phosphate-buffered saline (PBS) buffer (1.0 mL), and then 2.33 mg of NT (Anygen, Gwangju, Korea) was added. NT1 consisted of amino acids Cys-Glu-Leu-Tyr-Glu-Asn-Lys-Pro-Arg-Arg-Pro-Tyr-Ile-Leu, and the terminal cysteine was reacted with maleimide of PEG, thereby forming a PEG-NT conjugate. Such a reaction mixture was stirred at room temperature for 24 hours, dialyzed with distilled/deionized water at 4° C. overnight using a Slide-A-Lyzer™ cassette (3.5 kDa molecular weight cut-off; Thermo Scientific, Rockford, Ill.), and then lyophilized to prepare PEG-NT. The PEG-NT conjugation was confirmed by $^1$HNMR and matrix-assisted laser desorption/ionization time-of-flight (MALDI-TOF).

In addition, to confirm an effect according to the type of neurotensin peptide, NT2 (SEQ ID NO:2, Cys-Arg-Arg-Pro-Try-Ile-Leu) was conjugated with PEG by the same method as described above.

Referring to FIGS. 2 and 3, it was confirmed that PEG-NT was well bound according to a $^1$HNMR result and MALDI-TOF analysis.

Hereinafter, unless specifically indicated otherwise, the neurotensin peptide used was NT1, which was designated NT.

3. Conjugation of Ads with PEG-NT

The conjugation of Ads with PEG-NT was performed according to a previously-reported method[13].

Ads ($1\times10^{11}$ VP/mL) and a 3,3-dithiobis(sulfosuccinimidyl propionate) (DTSSP) crosslinker (Thermo Scientific) were pre-activated in 1×PBS buffer at a molar ratio (Ad:DTSSP) of $1:10^5$. After the resulting solution was maintained at room temperature for 30 minutes, $NH_2$—PEG-NT (the molar ratio of Ad:PEG-NT is $1:10^5$) was added. The reaction mixture was incubated at room temperature for 2 hours, and then quenched using an excessive amount of free L-lysine. Finally, to remove an unreacted reagent, the product was purified by ultrafiltration (Amicon Ultra Centrifugal Filter; Millipore, Billerica, Mass.).

4. Establishment of Optimal Conditions of DTSSP for Forming Ad-PEG-NT Conjugate

In PEGylation of Ad, introduction efficiency in PANC-1 cells was compared according to PEGylation per concentration of DTSSP, which is a crosslinker that allows conjugation of PEG with GFP-expressing Ads. GFP expression was observed by flow cytometry (BD Bioscience) 48 hours after the transformation. To further analyze a degree of PEG conjugation with the Ad surface, GFP-expressing replication-deficient Ad (dE1/GFP) was treated with the crosslinker at various concentrations (the molar ratio of DTSSP:Ad; $1\times10^4$, $1\times10^5$, $3\times10^5$), and then conjugated with $1\times10^5$ mol of PEG at room temperature for 30 minutes. Forty-eight hours after transfection into a pancreatic cancer cell line (PANC-1), for quantitative analysis of GFP expression of the virus transferred into the cells, FACS analysis was performed. According to a conventionally known method, a modified lysine residue of the dE1/GFP-PEG nanocomplex was quantified using fluorescamine (Sigma-Aldrich, St. Louis, Mo.)[42]. Fluorescence was measured using a fluorescence spectrophotometer (PerkinElmer, Waltham. Mass.).

As shown in FIGS. 4A and 4B, it was confirmed that, as the concentration of DTSSP was increased, Ad intracellular introduction efficiency was reduced, and it was also confirmed that, when the DTSSP concentration was $1\times10^5$ or more, the PEGylated Ad-intracellular introduction efficiency was reduced by 98% or more. In addition, as a result of quantitative analysis of a degree of binding PEG onto the Ad surface through fluorescamine analysis, it was confirmed that, when the DTSSP concentration was $1\times10^5$ or more, 80% or more amine groups are PEGylated on virus capsids. Although the DTSSP concentration was higher, a difference was not significantly exhibited. Therefore, when the Ad surface was PEGylated, and the molar ratio of the crosslinker and Ad was $1\times10^5$ to $3\times10^5$, it was confirmed that the Ad surface was almost completely masked. Therefore, an experiment was carried out by forming a complex within the above-mentioned range.

5. Establishment of Optimal Conditions for Conjugation of Ad and PEG (PEG-NT) to Form Ad-PEG-NT Conjugate To determine the optimal ratio of DTSSP to PEG-NT to form the final Ad-PEG-NT complex, the complex was fixed with two concentrations of DTSSP ($1\times10^5$ and $3\times10^5$) at which efficiency was verified in the above, dE1/GFP was reacted with various concentrations of PEG or PEG-NT ($1\times10^4$, $1\times10^5$ or $1\times10^6$), and then used to treat human pancreatic cancer cells (PANC-1) in which a neurotensin receptor was overexpressed to compare intracellular introduction efficiencies.

Specifically, the PANC-1 cells were seeded into a 24-well plate at a density of $5\times10^4$ cells/well for 24 hours. Afterward, transformation was performed by treating dE1/GFP, dE1/GFP-PEG or dE1/GFP-PEG-NT at 200 MOI, and 48 hours after culture, a degree of GFP expression was confirmed. The GFP expression was detected using a fluorescence microscope (Olympus IX81; Olympus Optical, Tokyo, Japan), and semi-quantitative analysis was carried out using ImageJ software (version 1.50b; U.S. National Institutes of Health, Bethesda, Md.). A semi-quantitatively analyzed image was expressed as an average optical density of three different digital images expressed as a relative change in GFP levels.

As shown in FIGS. 5A and 5B, when the treatment concentration of DTSSP and PEG-NT was $1\times10^5$, it was confirmed that GFP expression efficiency was high, and particularly, under a condition in which a PEG (or PEG-NT) concentration was $1\times10^5$, it was confirmed that the Ad-PEG-NT complex was formed, and the NTR-dependent target-ability was most highly exhibited.

6. Physicochemical Characteristics of Ad-PEG-NT Complex 6-1. Confirmation of Physicochemical Characteristics of Complex The average particle size and surface charge of naked dE1/GFP, dE1/GFP-PEG, or dE1/GFP-PEG-NT (the molar ratio of dE1/GFP:PEG or PEG-NT was $1:1\times10^5$) were measured using Zetasizer 3000HS (Malvern Instrument Inc., Worcestershire, UK) and a He—Ne laser beam (633 nm, fixed scattering angle: 90°) at room temperature. The final size was calculated as the average value of five independent results.

As shown in FIG. 6A, the average particle size of a wild-type Ad was 101.5±5.1 nm, and when PEG or PEG-NT was bound, it was confirmed that the average particle size was gradually increased to 109.2±3.3 or 119.7±3.9 nm, respectively. As the particle size increased, the surface charge was also increased. Particularly, it was confirmed that the surface charge of the naked Ad was −26.4±0.5 mV, and the surface charge of the PEG or PEG-NT-binding complex was −24.7±0.7 or −19.2±0.3 mV. Therefore, it was confirmed that the Ad-PEG-NT complex of the present invention has a suitable size for delivery to cells, and is stably formed.

6-2. Physicochemical Characteristics of Complex According to Type of Peptide

It was confirmed that physicochemical characteristics of the complex was changed according to the type of neurotensin peptide. Wild-type Ads were used as a control group, and after Ad-PEG-NT1 and Ad-PEG-NT2, in which Ad, Ad-PEG and neurotensin were bound, were prepared, size and surface charge were measured.

SEQ ID NO: 1
NT1: Cys-Glu-Leu-Tyr-Glu-Asn-Lys-Pro-Arg-Arg-Pro-Tyr-Ile-Leu

SEQ ID NO: 2
NT2: Cys-Arg-Arg-Pro-Tyr-Ile-Leu

As shown in FIGS. 6B and 6C, the size of the wild-type Ad was approximately 100 nm, and the size of Ad-PEG in which PEG was attached was increased to approximately 108 nm. In the case of targeting material (NT1 or NT2)-binding complexes, the size of Ad-PEG-NT1 was 118 nm, and the size of Ad-PEG-NT2 was approximately 115 nm. Compared with Ad, when PEG, NT2 or NT1 was bound, it was confirmed that the particle size was sequentially increased. As a result of the measurement of the surface charge, it was confirmed that the naked Ad has a surface charge value of −27 mV, and due to the binding of PEG, a negative charge was slightly decreased to approximately −23 mV. However, when a targeting group was attached, the surface charge of Ad-PEG-NT1 was −19 mV, and the surface charge of Ad-PEG-NT2 was −21 mV, and therefore it was confirmed that the surface charges thereof were higher than those of only PEG-binding or naked Ads.

7. Expression Level of NTR in Human Cancer Cells 7-1. NTR Expression in PANC-1, MIA PaCa-2, A549 and AsPC-1

NTR expression levels on the surfaces of human cancer cells (PANC-1, MIA PaCa-2, A549 and AsPC-1) were confirmed by flow cytometry. The cells were collected by the treatment of trypsin-EDTA, and washed with 1% FBS-containing PBS (pH 7.4). Afterward, the cells (3×10$^5$) were incubated along with an NTR-specific primary antibody (Ab, Abcam, Cambridge, UK) at 4° C. for 1 hour. The cells were washed with PBS/1% FBS twice, and incubated along with a secondary antibody (PE-labeled goat anti-mouse IgG; Santa Cruz Biotechnology, Santa Cruz, Calif.) at 4° C. for 40 minutes. After being washed with PBS/1% FBS twice, for analysis, the stained cells were resuspended in 0.5 ml of 1×PBS. Each type of cell stained with only a secondary antibody was used as a negative control. Flow cytometry was performed using an FACSCalibur analyzer (BD Bioscience, San Jose, Calif.) with Cell Quest software (BD Bioscience). Approximately 10,000 cell events were counted in each sample.

As shown in FIGS. 7A, 7B, 7C, 7D, 7E and 7F, it was confirmed that NTR was expressed at a very high level of approximately 72% and 67% in pancreatic cancer cell lines (PANC-1 and MIA PaCa-2), respectively, and was expressed at a low level of approximately 15% in another pancreatic cancer cell line, such as AsPC-1. It was confirmed that NTR was expressed at approximately 41% in a lung cancer cell line A549, and was hardly expressed in normal pancreatic cells (NPCs). Therefore, from the experimental result, the cell lines were classified into three types (high expression-high, intermediate expression-intermediate, low expression-low, and negative-negative) according to a degree of NTR expression, and then the following experiments were carried out.

7-2. NTR Expression in U343, BXPC3, MCF7, WRL-68 and HDF Cells

In addition, to confirm a degree of the expression of neurotensin receptor 1 (NTR1) in various cancer cells (U343, BXPC3 and MCF7) and normal cells (HDF and WRL-68), FACS analysis was performed. 3×10$^5$ of each type of cells were treated with an NTR1-specific antibody (Abcam) at 4° C. for 1 hour, washed with PBS (1% FBS) twice, and washed with a secondary antibody (PE-labeled goat anti-mouse IgG; Santa Cruz) at 4° C. for 40 minutes. After being washed twice, the cells were treated with a fixative (1% paraformaldehyde), FACS analysis was performed on each cell line to confirm whether NTR1 was expressed. As a negative control, a cell line treated with only a secondary antibody was used.

As shown in FIG. 7G, it was confirmed that, in a brain tumor cell line U343 among various cancer cell lines, the largest number of the cells, that is, 90% or more of the cells expressed NTR1, and in the pancreatic cancer cell line BXPC3, approximately 19% of the cells expressed NTR1. In addition, it was confirmed that, even in a breast cancer cell line MCF7, approximately 15% of the cells expressed NTR1. It was confirmed that, in normal cells such as HDF and WRL-68, approximately 18% and 30% of the cells expressed NTR1, respectively.

8. Confirmation of NTR-Dependent (Specific) Intracellular Introduction Efficiency 8-1. Confirmation of NTR-Specific Gene Delivery Efficiency of Ad-PEG-NT Complex To confirm NTR-specific gene delivery efficiency of the Ad-PEG-NT complex, a GFP-expressing Ad was bound with PEG and PEG-NT, and used to treat various cancer cell lines classified into three types according to NTR expression and a normal pancreatic cell line at 100 MOI and 500 MOI, respectively, and then after 48 hours, a degree of GFP expression was compared.

Specifically, before the delivery, each cell line was seeded into a 24-well plate at a density of 5×10$^4$ cells/well for 24 hours. Afterward, the concentration ratios of dE1/GFP:DTSSP and dE1/GFP:PEG or PEG-NT were fixed at 1:1× 10$^5$. The cells were treated with naked dE1/GFP, dE1/GFP-PEG or dE1/GFP-PEG-NT at 100 MOI (with respect to PANC-1, MIAPaCa-2, A549 and AsPC-1 cells) or 500 MOI (with respect to NPC) for transformation. The virus-treated cells were incubated in a fresh medium containing 5% FB S. Twenty-four hours after the transformation at 37° C., the cells were observed using a fluorescence microscope (Olympus Optical).

As shown in FIG. 8A, it was confirmed that, when Ad-PEG conjugated with PEG was commonly treated, intracellular introduction efficiency was significantly reduced, but due to binding of a targeting group, GFP expression efficiency was NTR-dependently increased. It was confirmed that NTR-high expression cell lines such as PANC-1 and MIA PaCa-2 exhibit the highest targetability caused by a targeting group, and there was almost no difference in targetability in an NTR low-expression cell line and an NTR-negative cell line, compared with an Ad-PEG-treated group. Therefore, it was confirmed that the Ad-PEG-NT complex manufactured in this experiment has targetability for NTR, and has higher intracellular uptake efficiency simply than a PEGylated Ad.

8-2. Confirmation of NTR-Dependent Intracellular Introduction Efficiency According to NT1 and NT2

To compare the neurotensin receptor-specific gene delivery efficiency of Ad-PEG-NT and delivery efficiency according to the type (NT1 or NT2) of neurotensin peptide in various cancer cell lines, various types of cancer cell lines were treated with a GFP-expressing replication-deficient Ad (dE1/GFP), a PEGylated Ad (dE1/GFP-PEG), and dE1/GFP-PEG-NT1 and dE1/GFP-PEG-NT2 nanocomplexes. $8 \times 10^4$ cells of each cancer cell line (PANC-1, MIA PaCa-2, U343, MCF7, HT-29, HT1080, or A549) were seeded in a 24-well plate, and after 24 hours, viral treatment was performed at a concentration suitable for each cell line (30 MOI for PANC-1 and MIA PaCa-2; 20 MOI for U343; 100 MOI for MCF7; 50 MOI for HT-29, HT1080 and A549). Forty-eight hours after the treatment, a degree of GFP expression was comparatively analyzed using a fluorescence microscope.

As shown in FIG. 8B, compared with the GFP expression in a wild-type Ad, it was confirmed that the degree of fluorescence expression in a cancer cell line treated with the PEGylated Ad complex was very significantly decreased by inhibiting non-specific intracellular infection due to the masking of the Ad surface. However, when cancer cells were treated with the Ad-PEG-NT nanocomplex, compared with the treatment of Ad-PEG, it can be observed that a degree of GFP fluorescence expression was increased in all cancer cells. In addition, as a result of confirming the difference in gene delivery efficiency according to the NT1 or NT2 type, in the pancreatic cancer cell lines (PANC-1 and MIA PaCa-2) and the brain tumor cell line (U343), it was confirmed that NT1 has slightly higher GFP expression than NT2. Therefore, according to this study, it was confirmed that reduced Ad-mediated gene delivery efficiency caused due to PEGylation of Ads can be restored through neurotensin receptor targeting.

8-3. Competition Assay

In addition, to confirm whether improved intracellular introduction efficiency of the Ad-PEG-NT complex is caused by direct binding with NTR regardless of CAR, a competition assay was performed.

Specifically, MIAPACA-2 cells were seeded in a 24-well plate at $1 \times 10^5$ cells per well. On the next day, before being transformed with naked dE1/GFP or dE1/GFP-PEG-NT, an Ad knob protein (0.2 or 1 µg/mL) and a neurotensin peptide (2 or 10 µg/mL), which were comprised in serum-free DMEM, was added to block each receptor present on a cell surface, and the cells were incubated at 4° C. for 1 hour. The NTR high-expression cell line MIA PaCa-2 was treated with 100 MOI of an Ad or Ad-PEG-NT complex at 37° C. for 48 hours, and then observed using a fluorescence microscope (Olympus Optical). GFP expression was quantified by flow cytometry and analyzed using Cell Quest software (BD Bioscience).

As shown in FIG. 9, as a result of treatment of a knob protein specific to a receptor of the wild-type Ad, that is, CAR, the intracellular introduction efficiency of the wild-type Ads was significantly decreased in a concentration-dependent manner (0.2 µg/mL-76%, 1 µg/mL-92%), whereas it was confirmed that, when the Ad-PEG-NT complex was treated, the intracellular introduction efficiency was hardly decreased. Likewise, as a result of treatment of a NTR-specific neurotensin peptide (NT), the degree of GFP expression of the wild-type Ad was hardly decreased, whereas, as a result of treatment of Ad-PEG-NT, it was confirmed that the degree of GFP expression was decreased in a NT concentration-dependent manner (2 µg/mL-60%, 10 µg/mL-89%). Therefore, from the results, it was confirmed that the Ad-PEG-NT complex was introduced into cells through direct binding between a neurotensin peptide and a neurotensin receptor (NTR) of the cell.

9. Verification of NTR-Specific Cancer Cell Killing Ability of oAd-PEG-NT Complex and Virus Production Ability 9-1. Confirmation of Cancer Cell Killing Ability After an oAd-PEG-NT complex was manufactured using a replication-competent Ad (oAd/DCN/LRP), to confirm an NTR-specific cancer cell killing ability, PANC-1 (high NTR expression), MIA PaCa-2 (intermediate NTR expression), A549 (low NTR expression) and normal NPC (negative) grown until 70% confluence in 24-well plates were infected with naked oAd/DCN/LRP, oAd/DCN/LRP-PEG or oAd/DCN/LRP-PEG-NT nanocomplexes at various MOIs, followed by MTT analyses. Specifically, two days after the infection, 200 µl MTT solution (2 mg/ml 3-(4,5-dimethyl-thiazol-2-yl)-2,5-diphenyl-tetrazolium bromide in PBS; Sigma-Aldrich) was added to each well, and the cells were incubated at 37° C. for 4 hours. Afterward, a supernatant was removed, and the pellet was dissolved in 1.0 mL of dimethyl sulfoxide. The plate was examined at 540 nm using a microplate reader. The cell viability of a PBS-treated cell group was analyzed by the same method as described above as a negative control.

As shown in FIGS. 10A, 10B, 10C, 10D and 10E, the wild-type Ad exhibited a potent cancer cell killing ability in proportion to a virus concentration in all cancer cell lines (PANC-1 200 MOI: 53% MIA PaCa-2 100 MOI: 87%, A549 10 MOI: 66%, AsPC-1 20 MOI: 59%). As a result of PEGylation, it was observed that non-specific intracellular infection was suppressed by blocking an Ad surface, and thus a cancer cell killing ability was greatly reduced (PANC-1 200 MOI: 24% MIA PaCa-2 100 MOI: 28%, A549 10 MOI: 9%, AsPC-1 20 MOI: 11%). However, as a result of binding together with a target group (NT) of a neurotensin receptor, it was confirmed that the cancer cell killing ability reduced by PEG binding was restored. Specifically, it was confirmed that there is no difference in cell lines with low or negative NTR expression, but as a degree in NTR expression is increased, the cancer cell killing ability was also restored (PANC-1 200 MOI: 62%, MIA PaCa-2 100 MOI: 74%, A549 10 MOI: 42%).

9-2. Analysis of Virus Production

In addition, 36 hours after the treatment of a replication-competent Ad, real time Q-PCR was carried out to quantitatively analyze an amount of viruses generated in each cell line.

Cancer cells (PANC-1, MIA PaCa-2, A549, and AsPC-1) or normal pancreatic cells (NPCs) were seeded in a 12-well plate and grown to approximately 60 to 70% confluence. 24 hours before infection, the medium in each well was exchanged with fresh serum-free DMEM, and then the cells were treated with naked oAd/DCN/LRP, oAd/DCN/LRP- PEG, or oAd/DCN/LRP-PEG-NT (PANC-1: 100 MOI, MIA PaCa-2: 100 MOI, A549: 10 MOI, AsPC-1: 20 MOI, and NPC: 100 MOI). Thirty-six hours after the infection, supernatants and cells were all collected, and the mixture underwent three cycles of freezing and thawing. The copy number of the Ad genome was measured by real-time quantitative PCR (TaqMan PCR detection; Applied Biosystems, Foster City, Calif.)[43]. Each sample was amplified in an ABI 7500 sequence detection system (Applied Biosystems) for 40 cycles, together with continuous fluorescence monitoring. All samples were analyzed three times, and data was processed using a SDS 19.1 software package (Applied Biosystems).

As shown in FIGS. 11A, 11B, 11C, 11D and 11E, as a result of comparing the number of generated viruses between cell lines with high NTR expression (PANC-1 and MIA PaCa-2), which were treated with oAd-PEG-NT, and those treated with an oAd-PEG complex, it was confirmed that a virus production ability was increased 550- and 842-fold, respectively. In the cell line with intermediate NTR expression, that is, A549, when oAd/DCN/LRP-PEG-NT was treated, it was confirmed that the virus production ability was increased 9-fold, compared with oAd/DCN/LRP-PEG. However, in a cell line with low or almost no NTR expression, it was confirmed that there was almost no difference in virus production ability. Therefore, as a result of this study, it was confirmed that the virus complex of the present invention had excellent intracellular gene delivery efficiency and cancer cell killing ability, which were specific for the cancer cell lines with high NTR expression, and an excellent virus production ability, and therefore it was confirmed that the complex is more suitable for the treatment of cancer.

10. Confirmation of Whether Immune Response is Induced by oAd-PEG-NT Complex 10-1. Analysis for Interleukin-6 (IL-6) and Neutralizing Antibody When Ads are administered systemically, the Ads are rapidly inactivated and disappear in a body due to an immune response occurring in the body. Since a viral surface is blocked, the PEGylated Ads used in this study may greatly reduce the induction of an immune response. Therefore, it was confirmed whether an innate or adaptive immune response against wild-type Ads, which is induced in a body, is reduced when an Ad-PEG-NT complex was administered systemically.

First, to confirm an effect of each type of Ad on an acute innate response, serum IL-6 obtained from mice (n=3) intravenously injected with naked oAd/DCN/LRP, oAd/DCN/LRP-PEG or oAd/DCN/LRP-PEG-NT at $1 \times 10^{10}$ VP/mouse was measured. A serum sample was collected 6 hours after the injection, a level of proinflammatory cytokine IL-6, which was generated in the serum was quantitatively analyzed by an enzyme-linked immunosorbent assay (ELISA; R&D Systems, Minneapolis, Minn.).

As shown in FIG. 12A, as a result of treatment of PBS (control), 48.5 pg/mL of IL-6 was generated, whereas as a result of treatment of a non-PEGylated Ad (oAd/DCN/LRP), the IL-6 level was measured at 143.2 pg/mL, which was increased three-fold, compared with the result of the treatment of PBS. However, when PEGylated oAd/DCN/LRP-PEG or oAd/DCN/LRP-PEG-NT was treated, it was confirmed that IL-6 (53.6 or 57.8 pg/mL, respectively) was generated at a very similar level to that of PBS. Accordingly, the induction of an immune response by viruses may be greatly reduced due to the PEGylated structure of the present invention.

In addition, to confirm whether an adaptive immune response against Ads is avoided, the generation of a neutralizing antibody was detected. Fourteen days after the $1 \times 10^{10}$ VP of naked oAd/DCN/LRP, oAd/DCN/LRP-PEG, or oAd/DCN/LRP-PEG-NT was intravenously injected into male BALB/c mice (Charles River Korea Inc., Seoul, Korea), another injection of the naked oAd/DCN/LRP, oAd/DCN/LRP-PEG, or oAd/DCN/LRP-PEG-NT was performed to generate a neutralizing antibody. Fourteen days after the second injection, whole blood was collected from the retro-orbital plexus of a mouse. Afterward, the mouse serum was treated to inactivate a complement at 56° C. for 45 minutes, and then stored at −20° C. For a neutralization protection assay, heat-inactivated serum of each batch obtained from the mice treated with naked oAd/DCN/LRP, oAd/DCN/LRP-PEG or oAd/DCN/LRP-PEG-NT was treated with serum-free DMEM mixed with dE1/GFP to prepare a 1:50 dilution and was incubated for 20 minutes at 37° C. to allow a reaction. Subsequently, A549 cells were treated with the serum-treated dE1/GFP. The A549 cells were grown in a 24-well plate to 80% confluence at 100 MOI, and incubated at 37° C. for 2 hours. The cells were washed, and incubated with 1 mL serum-free medium containing 5% FBS for 48 h, followed by analyses.

As the amount of neutralizing antibodies generated by the viruses that had been injected into the mice is increased, intracellular uptake is prevented due to suppression of the GFP viral activity, and thus the amount of production of the neutralizing antibodies can be estimated from a degree of GFP expression. Accordingly, the delivery was measured using a fluorescence microscope (Olympus Optical), and the cells were analyzed by flow cytometry and Cell Quest Software (BD Bioscience).

As shown in FIG. 12B, by a reaction with the serum obtained from the naked oAd/DCN/LRP-treated group, GFP expression was reduced by 82%, compared with that of the PBS-treated group (control). However, by a reaction with the serum obtained from the oAd/DCN/LRP-PEG or oAd/DCN/LRP-PEG-NT complex-treated group, it was confirmed that GFP expression was reduced approximately 4% or 13%, respectively, compared with that of the control group. Therefore, it was experimentally confirmed that it is possible to effectively avoid an immune response through systemic administration of the oAd/DCN/LRP-PEG-NT complex of the present invention.

11. Analyses of Pharmacokinetic Profiles

For effective cancer treatment after systemic administration, the injected Ad needs to remain in blood longer without disappearing and to be delivered to target cancer tissue, and for this reason, an experiment was carried out to confirm whether the Ad-PEG-NT complex is present in blood longer than the wild-type Ad.

Five, ten, twenty, thirty, sixty and three hundred or sixty minutes after PBS (control), naked oAd (naked oAd/DCN/LRP), oAd/DCN/LRP-PEG, or oAd/DCN/LRP-PEG-NT was intravenously injected at $1 \times 10^{10}$ VP, 100 pl of the whole blood from the retro-orbital plexus of a BALB/c mouse was collected, a remaining amount of the viruses (n=3) present in the blood over time was confirmed by real-time quantitative PCR (Q-PCR). Total DNA containing Ad DNA was extracted from an aliquot of the whole blood, and resuspended in distilled/deionized water to make a final volume of 50 µl. The extraction of total DNA was performed using the QIAamp DNA Blood Mini Kit (Qiagen, Hilden, Germany) according to the manufacturer's protocol. The copy number of Ad genomes was measured by real-time quantitative PCR (TaqMan PCR detection; Applied Biosystems)[43]. The samples were amplified, and analyzed three times as described above. Data were processed by the SDS 19.1 software package (Applied Biosystems).

As shown in FIG. 13, it was confirmed that, from 5 minutes after the injection of the naked oAd, the viruses rapidly disappeared in the blood, only 6.5% of the amount of the injected virus remained, and 6 hours after the injection, the virus almost disappeared. However, when PEGylated Ads (oAd/DCN/LRP-PEG or oAd/DCN/LRP-PEG-NT) were injected, even 5 minutes after the injection, it was confirmed that 94% of the viruses (oAd/DCN/LRP-PEG) or 99% of the viruses (oAd/DCN/LRP-PEG-NT) of the amount of the first injection remained. Even 6 hours after the injection, it was observed that 15 times (oAd/DCN/LRP-PEG) and 11 times (oAd/DCN/LRP-PEG-NT) more viruses remained in the blood than the naked oAd. Therefore, it can be seen that the virus complex of the present invention remains longer in a body and exhibits a therapeutic effect in cancer treatment.

12. Confirmation of Enhanced Antitumor Effect of oAd-PEG-NT Complex in Pancreatic Orthotopic Models As a result of the systemic administration of the oAd-PEG-NT complex, first, pancreatic cancer orthotopic models were manufactured to confirm an antitumor effect on pancreatic cancer. In the case of orthotopic models, it was difficult to visually observe the antitumor effect, and therefore, it was attempted to confirm the change in a luciferase signal in real time through an optical imaging technique. First, a lentivirus expressing firefly luciferase by a cytomegalovirus promoter was manufactured to infect a pancreatic cancer cell line MIA PaCa-2, resulting in the manufacture of MIA PaCa-2/fluc, which is a stable cell line expressing a luciferase.

The skin and muscles of the left side of the abdomen of each of 5-week old male nude mice (n=5; Charles River Korea Inc.) were disinfected and perforated with sterilized micro scissors to extract the entire pancreas out of the abdominal cavity, along with the spleen, and then $5 \times 10^6/100$ µl of MIA PaCa-2/fluc cells were injected into the pancreas. After 14 days, the mice were anesthetized with 2% isoflurane in oxygen, and for optical imaging, D-luciferin (150 mg/kg, Caliper, Hopkinton, Mass.) was intraperitoneally injected, and 15 minutes after the injection, the generation of a tumor was identified using bioluminescence imaging (IVIS; Xenogen, Alameda, Calif.). An in vivo bioluminescence signal was calculated as the sum of a signal generated from a mouse in a prone position and a mouse in a supine position, after the background of a total flux [photons/second (p/s)] was removed from an entire body part. The mice (approximately $1 \times 10^8$ p/s) were randomly divided into four groups, and administered an intravenous injection of 200 µL of PBS, naked oAd/DCN/LRP ($2 \times 10^{10}$ VP), oAd/DCN/LRP-PEG ($2 \times 10^{10}$ VP), or oAd/DCN/LRP-PEG-NT ($2 \times 10^{10}$ VP) three times every other day. Tumor growth was confirmed through imaging performed once every five days after the first administration. On day 46 after the injection, the tumor was collected, and the length and width of the tumor were measured, thereby measuring its volume. The tumor volume was measured using the following equation:

Volume=0.523L (W)².

As shown in FIGS. 14A, 14B and 14C, from observation until day 25, it was confirmed that the oAd/DCN/LRP-PEG-NT complex shows the lowest luciferase signal intensity, indicating that the oAd/DCN/LRP-PEG-NT complex exhibits a therapeutic effect 5.6 times higher than PBS (control), 2.7 times higher than naked oAd/DCN/LRP, and two times higher than oAd/DCN/LRP-PEG. In addition, 46 days after the first viral injection, as a result of measuring a size by extracting the tumor from the mouse, like the luciferase imaging result, it was confirmed that the size of a tumor treated with the oAd/DCN/LRP-PEG-NT complex is 98±9.2 mm³, which is the smallest value compared to those of the other controls (PBS: 287±78.8 mm³, oAd/DCN/LRP: 221.3±26.9 mm³, and oAd/DCN/LRP-PEG: 182.7±18 mm³), indicating an excellent tumor therapeutic effect.

13. Confirmation of In Vivo Distribution of oAd-PEG-NT Complex 13-1. Confirmation of In Vivo Distribution To examine whether low targetability to a tumor according to the tropism of the wild-type Ad on CAR, non-specific uptake into the liver and hepatotoxicity caused thereby can be overcome through PEGylation and presentation of an NT targeting group, in vivo distribution was confirmed through Q-PCR.

Specifically, $1 \times 10^{10}$ VP of the wild-type oAd/DCN/LRP, oAd/DCN/LRP-PEG or oAd/DCN/LRP-PEG-NT complex was intravenously injected into MIA PaCa-2 tumor-bearing mice three times every day (n=3), and PBS was solely injected as a control group (n=3). Twenty-four hours after the third injection of each complex, each organ (the stomach, the heart, the brain, the kidney, the muscle, the lung, the spleen, the prostate gland, the pancreas, and the liver) and the tumor of the mouse were harvested, and DNA was extracted using the QIAamp DNABlood Mini Kit (Qiagen), and amounts of the viruses present in tumor and organ tissue were quantitatively analyzed through Q-PCR.

As shown in FIG. 15A, it was confirmed that, compared with the naked Ad, the oAd/DCN/LRP-PEG or oAd/DCN/LRP-PEG-NT complex-administered group showed a 2.9× 10⁴- or 9.4×10³-fold reduction in accumulation in the liver, and compared with the naked Ad, the oAd/DCN/LRP-PEG or oAd/DCN/LRP-PEG-NT complex-administered group showed a $1.5 \times 10^2$ or $1.0 \times 10^3$-fold increase in accumulation in the tumor. Particularly, the oAd/DCN/LRP-PEG-NT complex showed 6.7-fold higher tumor targetability than the oAd/DCN/LRP-PEG complex. Such results represented that the efficiency of delivering the complex to a tumor, which was enhanced due to the EPR effect of the PEGylated oAd, was higher than that of the naked oAd/DCN/LRP, and it was confirmed that, due to tumor-specific targeting by NT, non-specific delivery to the liver was reduced, and the delivery efficiency to a tumor was increased, resulting in further improvement in target specificity of a therapeutic gene by the complex of the present invention.

13-2. Confirmation of In Vivo Toxicity

Further, to confirm hepatotoxicity, $1 \times 10^{10}$ VP of the naked, oAd/DCN/LRP, oAd/DCN/LRP-PEG or oAd/DCN/LRP-PEG-NT complex was intravenously injected, and PBS was solely injected as a control group (n=3). Seventy-two hours after the injection, blood was harvested for confirming degrees of the expression of aspartate aminotransferase (ALT) and alanine transaminase (AST), which are present in serum.

As shown in FIG. 15B, it was confirmed that the naked oAd/DCN/LRP-treated group showed a 37.3-fold (ALT) and 12.3-fold (AST) increase in the expression of the hepatotoxic factors, compared with the PBS control group. However, it was confirmed that the oAd/DCN/LRP-PEG or oAd/DCN/LRP-PEG-NT complex-administered group showed the expression of the hepatotoxic factors at similar levels as those of the PBS control group. Therefore, it can be seen that the complex of the present invention has a reduced non-specific delivery rate to the liver to significantly reduce hepatotoxicity, and thus the safety of the complex was highly enhanced.

Such results were confirmed to be consistent with, as shown in FIGS. 15C and 15D, results of an experiment for confirming an antitumor effect in which 35 days after the first viral injection, the liver of a mouse was extracted, and then hepatotoxicity was confirmed from a morphological change through H&E staining. It was confirmed that, in the naked oAd/DCN/LRP-treated group, due to hepatotoxicity, the size of the liver was significantly reduced, and the uptake of immune cells highly increased. However, the oAd/DCN/LRP-PEG or oAd/DCN/LRP-PEG-NT complex-administered group had almost no difference in morphological and histological changes of the liver from the PBS control group.

In addition, to identify the presence of Ads in the liver tissue, 35 days after the first viral injection, the extracted liver was fixed with 10% formalin, subjected to paraffin embedding, and cut into 5-µm sections. Afterward, the sections were immunostained with Ad hexon-specific antibodies (Santa Cruz Biotechnology) for observing histological changes.

As shown in FIG. 15E, the presence of Ads in the liver tissue was not identified in all groups.

14. Confirmation of Antitumor Effect of oAd-PEG-NT Complex Through Histological and Immunohistochemical Analyses 14-1. Confirmation of Antitumor Effect Through H&E, PCNA, E1A or TUNEL Staining To confirm the replication and proliferation of Ads and their therapeutic effect, histological staining (H&E or M&T), immunohistochemical staining (PCNA or E1A), or TUNEL assay was performed.

For analyses, the liver and the spleen were collected. Forty-six days after the final injection, the liver and the spleen were fixed with 10% formalin, subjected to paraffin embedding, and cut into 5-µm sections. Each section was stained by hematoxylin & eosin (H&E).

Seventy-two hours after the PBS, naked oAd/DCN/LRP ($2\times10^{10}$ VP), oAd/DCN/LRP-PEG ($2\times10^{10}$ VP), or oAd/DCN/LRP-PEG-NT ($2\times10^{10}$ VP) was intravenously injected three times, MIA PaCa-2 tumor tissue was harvested from a mouse. The tumor tissue was fixed with 10% formalin, subjected to paraffin embedding, and cut into 5-µm sections. The tumor tissue was stained with H&E (the cytoplasm and the nucleus) and Masson's trichrome/Picrosirius red, and was observed using a microscope.

The tumor sections were immunostained with a proliferated cell nuclear antigen (PCNA)-specific antibody (Dako, Glostrup, Denmark), and an effect on tumor cell proliferation was confirmed. Terminal deoxynucleotidyl transferase dUTP nick end labeling (TUNEL) analysis was carried out according to the manufacturer's protocol (Merck, Darmstadt, Germany). The tumor sections were also immunostained with an Ad E1A-specific antibody (Santa Cruz Biotechnology, Santa Cruz, Calif.), and were used to confirm viral proliferation. In addition, the tumor sections were stained with a Wnt-specific antibody (Cell Signaling Technology, Danvers, Mass.), a β-catenin-specific antibody (Cell Signaling Technology), and a vimentin-specific antibody (Cell Signaling Technology), respectively, and were analyzed to confirm the therapeutic effect of the Ad complex in tumors.

As shown in FIG. 16, first, according to the H&E staining, it can be confirmed that, in the PBS and naked oAd/DCN/LRP-treated groups, cancer cells were observed in most tissues, but in the oAd/DCN/LRP-PEG and oAd/DCN/LRP-PEG-NT complex-treated groups, most of the cancer cells were killed, and necrosis in tumor tissues was highly exhibited. In addition, as a result of the PCNA staining in tumor tissue to verify a degree of suppressing cell proliferation of tumor tissue and proliferation caused by a virus, it was confirmed that PCNA expression was significantly reduced in the oAd-PEG-NT complex-treated group. Subsequently, as a result of E1A staining performed to confirm the replication of Ads in a tumor, viral replication was not confirmed in the wild-type oAd-treated group, but E1A expression was confirmed in the oAd/DCN/LRP-PEG and oAd/DCN/LRP-PEG-NT complex-treated groups. Particularly, it was confirmed that E1A expression was most highly exhibited in the oAd/DCN/LRP-PEG-NT complex-treated group, which corresponds to the antitumor effect. In addition, to verify cancer cell killing ability caused by viral replication in tumor tissue, from the result of the TUNEL assay, it was confirmed that, corresponding to the antitumor effect, the oAd/DCN/LRP-PEG or oAd/DCN/LRP-PEG-NT complex has a higher cancer cell killing ability than that the naked oAd/DCN/LRP-treated group has. Particularly, in the oAd/DCN/LRP-PEG-NT complex-treated group, the highest cancer cell killing ability according to the viral replication was confirmed.

14-2. Confirmation of Change in Collagen Distribution in Tumor Tissue Through M&T and Picrosirius Staining Human pancreatic cancer is an intractable cancer in which penetration and diffusion of a therapeutic agent are difficult due to abnormally-overexpressed ECM, and as shown in FIG. 17, according to M&T staining, it was confirmed that collagen was overexpressed and distributed in human pancreatic cancer tissue (FIG. 17). Likewise, to maximize the effect of a therapeutic agent by reducing ECM overexpressed in cancer tissue, in this study, an Ad expressing a decorin gene (DCN), known to significantly reduce the ECM expression, was used. For a result of DCN expression according to viral replication and proliferation, two types of collagen staining methods (M&T and Picrosirius) were carried out to confirm whether ECM expression was reduced in a tumor.

As shown in FIG. 18, it was confirmed that a considerable decrease in collagen expression was exhibited in the case of the virus complex of the present invention, prepared to express a decorin gene, due to intensive replication and proliferation in a tumor.

15. Confirmation of Reduction in Wnt3a/β-Catenin Signaling Through Wnt, β-Catenin and Vimentin Staining As a replication-competent virus used in this study, a virus expressing sLRP6E1E2 capable of suppressing Wnt3a/β-catenin signaling involved in cancer proliferation and metastasis was used. Therefore, to confirm whether a strong antitumor effect resulting from viral replication and proliferation is the result obtained by suppressing the Wnt3a/β-catenin signaling in a tumor, the Wnt, (3-catenin and vimentin staining were carried out as described in 14-1, and then observed.

Figure 20:
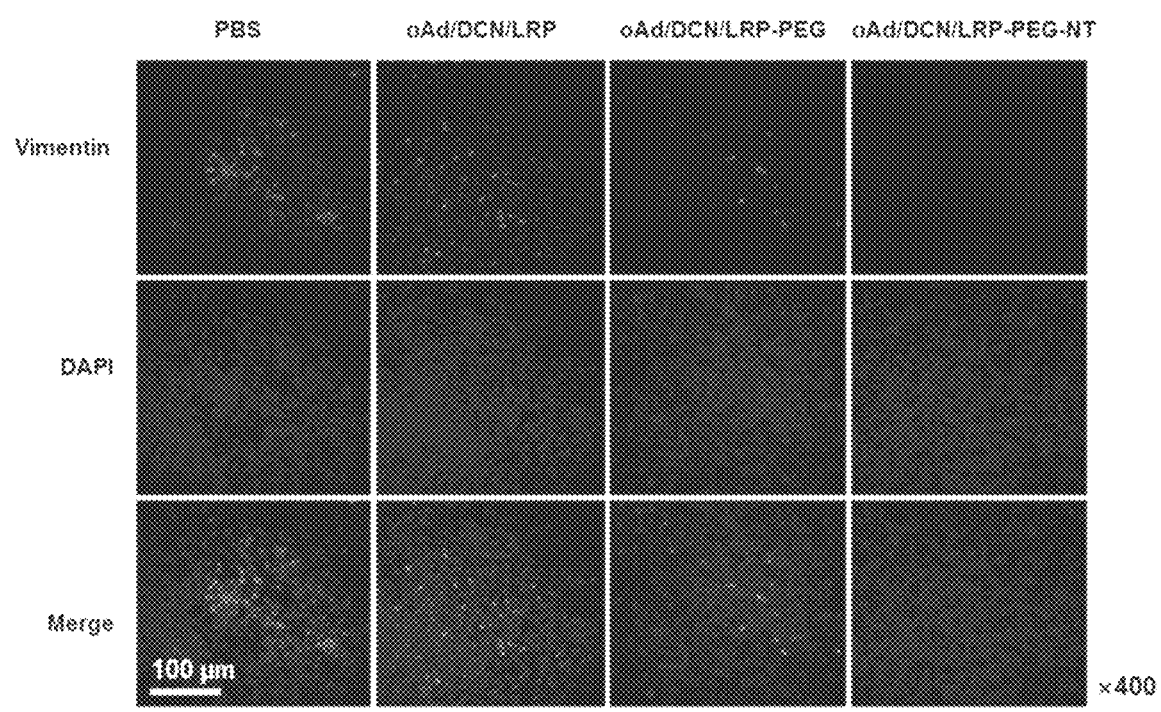
FIG. 20 shows the result of confirming changes in a marker related to Wnt/β-catenin signaling in tumor tissue according to administration of the Ad complex prepared according to an exemplary embodiment of the present invention.

As shown in FIGS. 19 and 20, it was confirmed that, corresponding to the antitumor effect, that Wnt, β-catenin and vimentin expressions were significantly decreased in the oAd-PEG-NT complex-treated group. Therefore, from the result of this study, it can be seen that an excellent antitumor effect in the oAd/DCN/LRP-PEG-NT complex-treated group results from the avoidance of an immune response caused by PEGylation, an increase in delivery efficiency according to an increased remaining amount in blood, enhanced pancreatic cancer targetability caused by NT, and the expression of a therapeutic gene according to the replication and proliferation of an oAd used.

16. Confirmation of Transduction Efficacy of Ad/HSA-PEG+Peptides

For the transduction efficacy assessment of adenovirus (Ad) conjugated with PEGylated and neurotensin receptor-targeted human serum albumin (HSA; HSA-PEG-NT), various types of cancer cells (MDA MB 231, SKBR-3, AsPC-1, Mia PaCa-2, or A549 cells) were transduced with either naked Ad or Ad conjugated with different variations of PEGylated HSAs at 40 or 100 multiplicity of infection (MOI).

For this experiment, replication-incompetent and green fluorescence protein (GFP)-expressing Ad (dE1/GFP) was utilized. HSA was PEGylated by utilizing a maleimide functionalized 3.5 kDa bifunctional PEG, then neurotensin receptor targeting NT peptide (NT 1) was conjugated to one of the remaining functional groups on bifunctional PEG, generating HSA-PEG, and HSA-PEG-NT, respectively. To generate the various complexes for transduction experiment, the capsid of dE1/GFP was conjugated with 3,3'-dithiobis(sulfosuccinimidylpropionate) (DTSSP) chemical cross linker through the excess lysine residues on viral capsid through constant shaking at 650 rpm for 30 min. Subsequently, DTSSP-conjugated dE1/GFP was mixed with HSA, HSA-PEG or HSA-PEG-NT under constant shaking at 650 rpm for 2 hr to generate Ad/HSA, Ad/HSA-PEG, or Ad/HSA-PEG-NT complex, respectively. At 48 hr post transduction, fluorescence microscope images were taken at ×100 magnification. dE1/GFP was conjugated to DTSSP at $1×10^6$ Ad:DTSSP molar ratio and for polymer conjugation to Ad/DTSSP complex Ad:polymer (HSA, HSA-PEG, or HSA-PEG-NT) molar ratios of $1×10^5$, $10^6$, and $10^7$ were examined Primary objective of Example 16 was to assess whether NT peptide conjugated to the surface of PEGylated HSA can endow Ad with neurotensin receptor targeting ability following conjugation through chemical crosslinker DTSSP. Secondary objective was to determine optimal Ad:polymer molar ratio to maximize transduction of Ad into neurotensin receptor-positive cancer cells.

As shown FIGS. 21A, 21B, 21C, 21D and 21E, Ad/HSA and Ad/HSA-PEG complexes lacking NT peptide showed much lower transduction efficacy than naked Ad in all cell lines tested, showing that surface of Ad was masked by the polymer. Importantly, Ad/HSA-PEG-NT complex showed much higher transduction efficiency than Ad/HSA or Ad/HSA-PEG complexes in pancreatic cancer cell lines with high expression level of neurotensin receptor (Mia PaCa-2 and PANC-1). These results illustrate that NT conjugated to HSA-PEG surface can endow Ad with neurotensin receptor targeting ability. There wasn't too much difference between Ad/HSA-PEG-NT complexes formed with Ad:polymer molar ratio of $1×10^6$ and $1×10^7$, thus $1×10^6$ was chosen as optimal Ad:polymer ratio for subsequent experiments.

17. Confirmation of Transduction Efficacy of Ad/(HSA-PEG-NT+HSA-PEG-PTX)

Chemotherapeutic [paclitaxel (PTX) or gemcitabine (GEM)]-conjugated and PEGylated HSA was generated in similar manner as to those mentioned above, generating HSA-PEG-PTX and HSA-PEG-GEM, respectively. HSA-PEG-PTX or HSA-PEG-GEM was mixed with HSA-PEG-NT at various HSA-PEG-PTX- or HSA-PEG-GEM-to-HSA-PEG-NT molar ratios (1:1, 2:1, 5:1, 1:2, or 1:5). The mixture was conjugated with DTSSP-conjugated dE1/GFP to generate Ad/HSA-PEG-(NT+PTX) or Ad/HSA-PEG-(NT+GEM) complexes (noted as N+P or N+G in the FIGS. 22A, 22B, 22C and 22D of the fluorescence microscope images). At all times, dE1/GFP:polymer molar ratio was fixed at $1×10^6$; for example N+G (1:1) complex utilized 1 molar equivalent of dE1/GFP, $5×10^5$ molar equivalent of HSA-PEG-NT, and $5×10^5$ molar equivalent of HSA-PEG-GEM to have total Ad:polymer molar ratio fixed at $1×10^6$. All complexation procedure with DTSSP, single polymer, or polymer mixture was performed as described above under constant shaking (650 rpm) at room temperature.

Purpose of Example 16 was to determine whether drugs conjugated to surface of HSA-PEG can synergistically enhance the transduction efficiency of Ad when used in combination with HSA-PEG-NT. This approach was utilized to allow facile customization in the ratios between chemotherapeutic and targeting moiety conjugated to surface of Ad through HSA-PEG. As both PEGylation and conjugation of DTSSP crosslinker must occur through amine residues readily accessible on HSA surface, this approach was more practical than generating various variations of HSA-PEG containing both targeting moiety and drug on same polymer backbone.

As shown FIGS. 22A, 22B, 22C and 22D, when HSA-PEG-NT and HSA-PEG-PTX were conjugated to Ad surface at HSA-PEG-NT: HSA-PEG-PTX molar ratio of 5:1, the highest transduction efficiency was achieved in neurotensin receptor-positive cells (A549, PANC-1, Mia PaCa-2). This result likely suggests that small quantity of PTX is sufficient to enhance the transgene expression of Ad and higher concentration of targeting moiety is necessary to facilitate the internalization of both Ad and drug into neurotensin receptor overexpressing cancer cells.

REFERENCE

[1] D. Yadav, A. B. Lowenfels, The epidemiology of pancreatitis and pancreatic cancer, Gastroenterology, 144 (2013) 1252-1261.

[2] A. Jemal, R. Siegel, E. Ward, Y. Hao, J. Xu, M. J. Thun, Cancer statistics, 2009, CA Cancer J Clin, 59 (2009) 225-249.

[3] D. Laheru, B. Biedrzycki, E. M. Jaffee, Development of a cytokine-modified allogeneic whole cell pancreatic cancer vaccine, Methods Mol Biol, 980 (2013) 175-203.

[4] J. P. Neoptolemos, D. D. Stocken, H. Friess, C. Bassi, J. A. Dunn, H. Hickey, H. Beger, L. Fernandez-Cruz, C. Dervenis, F. Lacaine, M. Falconi, P. Pederzoli, A. Pap, D. Spooner, D. J. Kerr, M. W. Buchler, C. European Study Group for Pancreatic, A randomized trial of chemoradiotherapy and chemotherapy after resection of pancreatic cancer, The New England journal of medicine, 350 (2004) 1200-1210.

[5] D. G. Haller, Future directions in the treatment of pancreatic cancer, Seminars in oncology, 29 (2002) 31-39.

[6] D. P. Ryan, C. G. Willett, Management of locally advanced adenocarcinoma of the pancreas, Hematol Oncol Clin North Am, 16 (2002) 95-103.

[7] H. L. Kaufman, J. Di Vito, Jr., H. Horig, Immunotherapy for pancreatic cancer: current concepts, Hematol Oncol Clin North Am, 16 (2002) 159-197, viii.

[8] P. Phillips, Pancreatic stellate cells and fibrosis, in: P. J. Grippo, H. G. Munshi (Eds.) Pancreatic Cancer and Tumor Microenvironment, Trivandrum (India), 2012.

[9] Y. Shintani, M. A. Hollingsworth, M. J. Wheelock, K. R. Johnson, Collagen I promotes metastasis in pancreatic cancer by activating c-Jun NH(2)-terminal kinase 1 and up-regulating N-cadherin expression, Cancer research, 66 (2006) 11745-11753.

[10] M. Erkan, J. Kleeff, A. Gorbachevski, C. Reiser, T. Mitkus, I. Esposito, T. Giese, M. W. Buchler, N. A. Giese, H. Friess, Periostin creates a tumor-supportive microenvironment in the pancreas by sustaining fibrogenic stellate cell activity, Gastroenterology, 132 (2007) 1447-1464.

[11] F. Kreppel, S. Kochanek, Modification of adenovirus gene transfer vectors with synthetic polymers: a scientific review and technical guide, Mol Ther, 16 (2008) 16-29.

[12] I. K. Choi, Y. S. Lee, J. Y. Yoo, A. R. Yoon, H. Kim, D. S. Kim, D. G. Seidler, J. H. Kim, C. O. Yun, Effect of decorin on overcoming the extracellular matrix barrier for oncolytic virotherapy, Gene therapy, 17 (2010) 190-201.

[13] P. H. Kim, J. H. Sohn, J. W. Choi, Y. Jung, S. W. Kim, S Haam, C. O. Yun, Active targeting and safety profile of PEG-modified adenovirus conjugated with herceptin, Biomaterials, 32 (2011) 2314-2326.

[14] M. D. Wheeler, S. Yamashina, M. Froh, I. Rusyn, R. G. Thurman, Adenoviral gene delivery can inactivate Kupffer cells: role of oxidants in NF-κB activation and cytokine production, Journal of Leukocyte Biology, 69 (2001) 622-630.

[15] A. H. Baker, S. A. Nicklin, D. M. Shayakhmetov, FX and Host Defense Evasion Tactics by Adenovirus, Mol Ther, 21 (2013) 1109-1111.

[16] T. Nakamura, K. Sato, H. Hamada, Reduction of Natural Adenovirus Tropism to the Liver by both Ablation of Fiber-Coxsackievirus and Adenovirus Receptor Interaction and Use of Replaceable Short Fiber, J Virol, 77 (2003) 2512-2521.

[17] J. Kim, Y. Li, S. W. Kim, D. S. Lee, C.-O. Yun, Therapeutic efficacy of a systemically delivered oncolytic adenovirus—Biodegradable polymer complex, Biomaterials, 34 (2013) 4622-4631.

[18] C. O. Yun, Current advances in adenovirus nanocomplexes: more specificity and less immunogenicity, BMB Rep, 43 (2010) 781-788.

[19] J. W. Choi, J. S. Lee, S. W. Kim, C. O. Yun, Evolution of oncolytic adenovirus for cancer treatment, Adv Drug Deliv Rev, 64 (2012) 720-729.

[20] P. H. Kim, J Kim, T. I. Kim, H. Y. Nam, J. W. Yockman, M. Kim, S. W. Kim, C. O. Yun, Bioreducible polymer-conjugated oncolytic adenovirus for hepatoma-specific therapy via systemic administration, Biomaterials, 32 (2011) 9328-9342.

[21] D. Kasala, J. W. Choi, S. W. Kim, C. O. Yun, Utilizing adenovirus vectors for gene delivery in cancer, Expert Opin Drug Deliv, 11 (2014) 379-392.

[22] C. Delgado, G. E. Francis, D. Fisher, The uses and properties of PEG-linked proteins, Crit Rev Ther Drug Carrier Syst, 9 (1992) 249-304.

[23] H. Mok, D. J. Palmer, P. Ng, M. A. Barry, Evaluation of polyethylene glycol modification of first-generation and helper-dependent adenoviral vectors to reduce innate immune responses, Mol Ther, 11 (2005) 66-79.

[24] R. Alemany, K. Suzuki, D. T. Curiel, Blood clearance rates of adenovirus type 5 in mice, J Gen Virol, 81 (2000) 2605-2609.

[25] K. Doronin, E. V. Shashkova, S. M. May, S. E. Hofherr, M. A. Barry, Chemical modification with high molecular weight polyethylene glycol reduces transduction of hepatocytes and increases efficacy of intravenously delivered oncolytic adenovirus, Human gene therapy, 20 (2009) 975-988.

[26] C. R. O'Riordan, A. Lachapelle, C. Delgado, V. Parkes, S. C. Wadsworth, A. E. Smith, G. E. Francis, PEGylation of adenovirus with retention of infectivity and protection from neutralizing antibody in vitro and in vivo, Human gene therapy, 10 (1999) 1349-1358.

[27] J. Lanciotti, A. Song, J. Doukas, B. Sosnowski, G. Pierce, R. Gregory, S. Wadsworth, C. O'Riordan, Targeting adenoviral vectors using heterofunctional polyethylene glycol FGF2 conjugates, Mol Ther, 8 (2003) 99-107.

[28] Y. Eto, J. Q. Gao, F. Sekiguchi, S. Kurachi, K. Katayama, H. Mizuguchi, T. Hayakawa, Y. Tsutsumi, T. Mayumi, S. Nakagawa, Neutralizing antibody evasion ability of adenovirus vector induced by the bioconjugation of methoxypolyethylene glycol succinimidyl propionate (MPEG-SPA), Biol Pharm Bull, 27 (2004) 936-938.

[29] K. Ogawara, M. G. Rots, R. J. Kok, H. E. Moorlag, A. M. Van Loenen, D. K. Meijer, H. J. Haisma, G. Molema, A novel strategy to modify adenovirus tropism and enhance transgene delivery to activated vascular endothelial cells in vitro and in vivo, Human gene therapy, 15 (2004) 433-443.

[30] Y. Eto, J. Q. Gao, E Sekiguchi, S. Kurachi, K. Katayama, M. Maeda, K. Kawasaki, H. Mizuguchi, T. Hayakawa, Y. Tsutsumi, T. Mayumi, S. Nakagawa, PEGylated adenovirus vectors containing RGD peptides on the tip of PEG show high transduction efficiency and antibody evasion ability, J Gene Med, 7 (2005) 604-612.

[31] J. M. Kuldo, S. A. Asgeirsdottir, P. J. Zwiers, A. R. Bellu, M. G. Rots, J. A. Schalk, K. I. Ogawara, C. Trautwein, B. Banas, H. J. Haisma, G. Molema, J. A. Kamps, Targeted adenovirus mediated inhibition of NF-kappaB-dependent inflammatory gene expression in endothelial cells in vitro and in vivo, Journal of controlled release: official journal of the Controlled Release Society, 166 (2013) 57-65.

[32] J. G. Wang, N. N. Li, H. N. Li, L. Cui, P. Wang, Pancreatic cancer bears overexpression of neurotensin and neurotensin receptor subtype-1 and SR 48692 counteracts neurotensin induced cell proliferation in human pancreatic ductal carcinoma cell line PANC-1, Neuropeptides, 45 (2011) 151-156.

[33] J. C. Reubi, B. Waser, H. Friess, M. Buchler, J. Laissue, Neurotensin receptors: a new marker for human ductal pancreatic adenocarcinoma, Gut, 42 (1998) 546-550.

[34] S. Dupouy, N. Mourra, V. K. Doan, A. Gompel, M. Alifano, P. Forgez, The potential use of the neurotensin high affinity receptor 1 as a biomarker for cancer progression and as a component of personalized medicine in selective cancers, Biochimie, 93 (2011) 1369-1378.

[35] S. Shimizu, J. Tsukada, T. Sugimoto, N. Kikkawa, K. Sasaki, H. Chazono, T. Hanazawa, Y. Okamoto, N. Seki, Identification of a novel therapeutic target for head and neck squamous cell carcinomas: a role for the neurotensin-neurotensin receptor 1 oncogenic signaling pathway, International journal of cancer. Journal international du cancer, 123 (2008) 1816-1823.

[36] J. S. Lee, M. W. Hur, S. K. Lee, W. I. Choi, Y. G. Kwon, C. O. Yun, A novel sLRP6E1E2 inhibits canonical Wnt signaling, epithelial-to-mesenchymal transition, and induces mitochondria-dependent apoptosis in lung cancer, PloS one, 7 (2012) e36520.

[37] P. Astudillo, J. Larrain, Wnt signaling and cell-matrix adhesion, Current molecular medicine, 14 (2014) 209-220.

[38] J. Cui, W. Jiang, S. Wang, L. Wang, K. Xie, Role of Wnt/beta-catenin signaling in drug resistance of pancreatic cancer, Current pharmaceutical design, 18 (2012) 2464-2471.

[39] K. J. Kim E, Shin H Y, Lee H, Yang J M, Kin J, Sohn J H, Kim H, Yun co, AdmTERTD19, a Conditional Replication Competent Adenovirus Driven by the Human Telomerase Promoter, Selectively Replicates in and Elicits Cytopathic Effect in a Cancer Cell-Specific Manner, (2003).

[40] O. J. Kwon, P. H. Kim, S. Huyn, L. Wu, M. Kim, C. O. Yun, A hypoxia- and {alpha}-fetoprotein-dependent oncolytic adenovirus exhibits specific killing of hepatocellular carcinomas, Clin Cancer Res, 16 (2010) 6071-6082.

[41] Immunological data from cancer patients treated with Ad5 3-E2F-Δ24-GMCSF suggests utility for tumor immunotherapy, (2014).

[42] M. L. Read, T. Etrych, K. Ulbrich, L. W. Seymour, Characterisation of the binding interaction between poly (L-lysine) and DNA using the fluorescamine assay in the preparation of non-viral gene delivery vectors, FEBS letters, 461 (1999) 96-100.

[43] J. Kim, P H Kim, H. Y. Nam, J. S. Lee, C. O. Yun, S. W. Kim, Linearized oncolytic adenoviral plasmid DNA delivered by bioreducible polymers, Journal of controlled release: official journal of the Controlled Release Society, 158 (2012) 451-460.

[44] Y. Jung, H. J. Park, P. H. Kim, J. Lee, W. Hyung, J. Yang, H. Ko, J. H. Sohn, J. H. Kim, Y. M. Huh, C. O. Yun, S. Haam, Retargeting of adenoviral gene delivery via Herceptin-PEG-adenovirus conjugates to breast cancer cells, Journal of controlled release: official journal of the Controlled Release Society, 123 (2007) 164-171.

[45] M. Pasca di Magliano, A. V. Biankin, P. W. Heiser, D. A. Cano, P. J. Gutierrez, T. Deramaudt, D. Segara, A. C. Dawson, J. G. Kench, S. M. Henshall, R. L. Sutherland, A. Dlugosz, A. K. Rustgi, M. Hebrok, Common activation of canonical Wnt signaling in pancreatic adenocarcinoma, PloS one, 2 (2007) e1155.

[46] R. Alemany, D. T. Curiel, CAR-binding ablation does not change biodistribution and toxicity of adenoviral vectors, Gene therapy, 8 (2001) 1347-1353.

[47] W. E. Naugler, M. Karin, The wolf in sheep's clothing: the role of interleukin-6 in immunity, inflammation and cancer, Trends Mol Med, 14 (2008) 109-119.

[48] O. J. Kwon, E. Kang, J. W. Choi, S. W. Kim, C. O. Yun, Therapeutic targeting of chitosan-PEG-folate-complexed oncolytic adenovirus for active and systemic cancer gene therapy, Journal of controlled release: official journal of the Controlled Release Society, 169 (2013) 257-265.

[49] X. F. Fei, Q. B. Zhang, J. Dong, Y. Diao, Z. M. Wang, R. J. Li, Z. C. Wu, A. D. Wang, Q. Lan, S. M. Zhang, Q. Huang, Development of clinically relevant orthotopic xenograft mouse model of metastatic lung cancer and glioblastoma through surgical tumor tissues injection with trocar, J Exp Clin Cancer Res, 29 (2010) 84.

[50] I. Dmitriev, V. Krasnykh, C. R. Miller, M. Wang, E. Kashentseva, G. Mikheeva, N. Belousova, D. T. Curiel, An adenovirus vector with genetically modified fibers demonstrates expanded tropism via utilization of a coxsackievirus and adenovirus receptor-independent cell entry mechanism, Journal of virology, 72 (1998) 9706-9713.

[51] C. R. Miller, D. J. Buchsbaum, P. N. Reynolds, J. T. Douglas, G. Y. Gillespie, M. S. Mayo, D. Raben, D. T. Curiel, Differential susceptibility of primary and established human glioma cells to adenovirus infection: targeting via the epidermal growth factor receptor achieves fiber receptor-independent gene transfer, Cancer research, 58 (1998) 5738-5748.

[52] R. S. Everett, B. L. Hodges, E. Y. Ding, F. Xu, D. Serra, A. Amalfitano, Liver toxicities typically induced by first-generation adenoviral vectors can be reduced by use of E1, E2b-deleted adenoviral vectors, Human gene therapy, 14 (2003) 1715-1726.

[53] M. Johnson, S. Huyn, J. Burton, M. Sato, L. Wu, Differential biodistribution of adenoviral vector in vivo as monitored by bioluminescence imaging and quantitative polymerase chain reaction, Human gene therapy, 17 (2006) 1262-1269.

[54] J. N. Lozier, M. E. Metzger, R. E. Donahue, R. A. Morgan, Adenovirus-Mediated Expression of Human Coagulation Factor IX in the Rhesus Macaque Is Associated With Dose-Limiting Toxicity, Blood, 94 (1999) 3968-3975.

[55] D. A. Muruve, M. J. Barnes, I. E. Stillman, T. A. Libermann, Adenoviral gene therapy leads to rapid induction of multiple chemokines and acute neutrophil-dependent hepatic injury in vivo, Human gene therapy, 10 (1999) 965-976.

[56] C. O. Yun, Overcoming the extracellular matrix barrier to improve intratumoral spread and therapeutic potential of oncolytic virotherapy, Curr Opin Mol Ther, 10 (2008) 356-361.

[57] I. K. Choi, R. Strauss, M. Richter, C. O. Yun, A. Lieber, Strategies to increase drug penetration in solid tumors, Frontiers in oncology, 3 (2013) 193.

---

The invention claimed is:

1. A gene delivery system, comprising:
an adenovirus (Ad), polyethylene glycol (PEG) and a neurotensin receptor-specific binding peptide (NT), wherein the NT is conjugated with the PEG to form PEG-NT conjugate, and the PEG is conjugated to the surface of the Ad capsid with a crosslinker; and
wherein the Ad is conjugated with the PEG-NT conjugate in the ratio of 1 mol:$1\times10^4$-$1\times10^6$ mol.

2. The gene delivery system of claim 1, wherein the crosslinker is 3,3'-dithsiobis(sulfosuccinimidyl propionate) (DTSSP), and the Ad is conjugated with DTSSP at the ratio of 1 mol:$1\times10^5$ to $3\times10^5$ mol.

3. The gene delivery system of claim 1, wherein the NT consists of the amino acid sequence of SEQ ID NO: 1 or the amino acid sequence of SEQ ID NO: 2.

4. The gene delivery system of claim 1, wherein the Ad further comprises one or more target genes.

5. A complex for gene therapy comprising:
an adenovirus (Ad), polyethylene glycol (PEG), a neurotensin receptor-specific binding peptide (NT), and chemical therapeutic drugs,
wherein the chemical therapeutic drugs are conjugated with the PEG, the NT is conjugated with the PEG to form PEG-NT conjugate, and the PEG is conjugated to the surface of the Ad capsid with a crosslinker, and
wherein the Ad is conjugated with the PEG-NT conjugate in the ratio of 1 mol:$1\times10^4$-$1\times10^6$ mol.

6. A complex for gene therapy comprising:
an adenovirus (Ad), polyethylene glycol (PEG), and a neurotensin receptor-specific binding peptide (NT),
wherein the Ad comprises a therapeutic gene, and
wherein the NT is conjugated with the PEG to form PEG-NT conjugate, and the PEG is conjugated to the surface of the Ad capsid with a crosslinker, and
wherein the Ad is conjugated with the PEG-NT conjugate in the ratio of 1 mol:$1\times10^4$-$1\times10^6$ mol.

7. The complex of claim 6, wherein the therapeutic gene comprises the nucleotide sequence of a decorin gene and the nucleotide sequence of SEQ ID NO: 3 encoding a Wnt3a/β-catenin signaling inhibitory protein.

8. A method for preparing a gene delivery system or a complex for gene therapy, comprising:
reacting an adenovirus (Ad) with a crosslinker 3,3'-dithiobis(sulfosuccinimidyl propionate) (DTSSP) at the ratio of 1 mol:$1\times10^5$ to $3\times10^5$ mol to conjugate the crosslinker to the surface of the Ad capsid;
preparing a polyethylene glycol-neurotensin receptor-specific binding peptide (PEG-NT) conjugate by reacting the PEG and NT; and
preparing an Ad-PEG-NT conjugate by reacting the Ad and the PEG-NT conjugate, and wherein the Ad is conjugated with the PEG-NT conjugate in the ratio of 1 mol:$1\times10^4$-$1\times10^6$ mol.

\* \* \* \* \*

UNITED STATES PATENT AND TRADEMARK OFFICE
CERTIFICATE OF CORRECTION

PATENT NO. : 11,235,072 B2  
APPLICATION NO. : 15/952191  
DATED : February 1, 2022  
INVENTOR(S) : Yun et al.

Page 1 of 1

It is certified that error appears in the above-identified patent and that said Letters Patent is hereby corrected as shown below:

On the Title Page

Item (54) and in the Specification Column 1, Line 2, "IHERAPY" should be changed to --THERAPY--

Signed and Sealed this  
Twenty-sixth Day of July, 2022

Katherine Kelly Vidal  
*Director of the United States Patent and Trademark Office*